(12) United States Patent
Asano et al.

(10) Patent No.: US 11,203,565 B2
(45) Date of Patent: Dec. 21, 2021

(54) ESTER COMPOUND AND PIN1 INHIBITOR, INFLAMMATORY DISEASE THERAPEUTIC, AND COLON CANCER THERAPEUTIC IN WHICH SAID ESTER COMPOUND IS USED

(71) Applicants: Hiroshima University, Higaschihiroshima (JP); Tokyo University of Pharmacy & Life Sciences, Hachioji (JP); The University of Tokyo, Tokyo (JP)

(72) Inventors: Tomoichiro Asano, Hiroshima (JP); Yusuke Nakatsu, Hiroshima (JP); Hisanaka Ito, Hachioji (JP); Takayoshi Okabe, Tokyo (JP)

(73) Assignees: Hiroshima University, Hiroshima (JP); Tokyo University of Pharmacy & Life Sciences, Tokyo (JP); The University of Tokyo, Tokyo (JP)

( * ) Notice: Subject to any disclaimer, the term of this patent is extended or adjusted under 35 U.S.C. 154(b) by 29 days.

(21) Appl. No.: 16/464,034

(22) PCT Filed: Nov. 29, 2017

(86) PCT No.: PCT/JP2017/042804
§ 371 (c)(1),
(2) Date: May 24, 2019

(87) PCT Pub. No.: WO2018/101329
PCT Pub. Date: Jun. 7, 2018

(65) Prior Publication Data
US 2019/0382330 A1    Dec. 19, 2019

(30) Foreign Application Priority Data
Nov. 29, 2016   (JP) .............................. JP2016-231875

(51) Int. Cl.
| | |
|---|---|
| *C07C 65/30* | (2006.01) |
| *A61P 35/00* | (2006.01) |
| *A61P 1/16* | (2006.01) |
| *A61P 1/04* | (2006.01) |
| *A61K 9/00* | (2006.01) |
| *C07C 65/40* | (2006.01) |
| *C07C 62/36* | (2006.01) |
| *C07D 307/68* | (2006.01) |
| *C07D 209/86* | (2006.01) |
| *C07D 209/08* | (2006.01) |
| *C07C 229/56* | (2006.01) |
| *C07C 229/16* | (2006.01) |
| *C07C 59/74* | (2006.01) |
| *C07D 265/38* | (2006.01) |

(52) U.S. Cl.
CPC ............ *C07C 65/30* (2013.01); *A61K 9/0019* (2013.01); *A61K 9/0053* (2013.01); *A61P 1/04* (2018.01); *A61P 1/16* (2018.01); *A61P 35/00* (2018.01); *C07C 59/74* (2013.01); *C07C 62/36* (2013.01); *C07C 65/40* (2013.01); *C07C 229/16* (2013.01); *C07C 229/56* (2013.01); *C07D 209/08* (2013.01); *C07D 209/86* (2013.01); *C07D 265/38* (2013.01); *C07D 307/68* (2013.01)

(58) Field of Classification Search
None
See application file for complete search history.

(56) References Cited

FOREIGN PATENT DOCUMENTS

| | | |
|---|---|---|
| CA | 2517281 | 10/2004 |
| EP | 1603926 | 12/2005 |
| JP | 2006-523669 | 10/2006 |
| WO | WO 2004/087720 | 10/2004 |

OTHER PUBLICATIONS

Yu et al., Function of PIN1 in Cancer Development and Its Inhibitors as Cancer Therapeutics. Frontiers in Cell and Developmental Biology, 2020, 8, p. 1-12.*

(Continued)

*Primary Examiner* — Po-Chih Chen
(74) *Attorney, Agent, or Firm* — William C. Schrot; Jeffrey I. Auerbach; AuerbachSchrot LLC

(57) ABSTRACT

An object of the present invention is to develop a therapeutic agent for an inflammatory disease such as an inflammatory bowel disease or NASH, which therapeutic agent shows less side effects and high effectiveness. The present invention provides a compound represented by Formula (I) or a salt thereof; and a Pin1 inhibitor, a pharmaceutical composition, a therapeutic agent or a prophylactic agent for an inflammatory disease, and a therapeutic agent or a prophylactic agent for colon cancer, containing the compound.

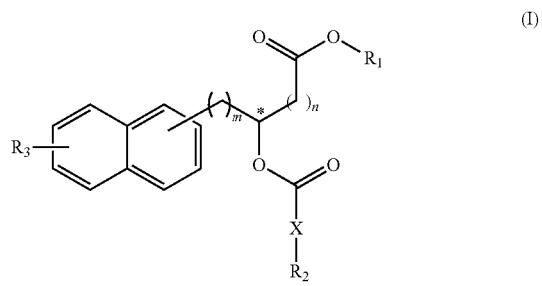

(I)

18 Claims, 8 Drawing Sheets
Specification includes a Sequence Listing.

(56) References Cited

OTHER PUBLICATIONS

Schafer, S., Kolkhof, P. Failure is an option: learning from unsuccessful proof-of-concept trials. Drug Discovery Today. Nov. 2008, 13, 913-916.*

Horig, H., Pullman, W. From bench to clinic and back: Perspective on the 1st IQPC Translational Research conference. Journal of Translational Medicine. Dec. 2004, 2, 44.*

Chemical Abstract Registry No. 95166-12-4, indexed in the Registry File on STN CAS Online Mar. 9, 1985.*

Grant & Hackh's Chemical Dictionary (5th Ed. 1987) at p. 148.*

Diaz-Alverez, A.E., et al. (2014) "*Access to Optically Pure beta-Hydroxy Esters via Non-Enzymatic Kinetic Resolution by a Planar-Chiral DMAP Catalyst,*" Molecules 19(9): 14273-14291.

International Search Report PCT/JP2017/042804 (WO 2018/101329) (dated 2018) (5 pages).

Potter, A.J., et al. (2010) "*Structure-guided Design of α-amino Acid-derived Pin1 Inhibitors,*" Bioorg. & Medicinal Chem. Lett. 20(2):586-590.

Tan, F., et al. (2016) "*Asymmetric Catalytic Insertion of α-Diazo Carbonyl Compounds into O—H Bonds of Carboxylic Acids,*" ACS Catalysis 6(10):6930-6934.

Written Opinion of the International Searching Authority PCT/JP2017/042804 (WO 2018/101329) (dated 2018) (5 pages).

Chan, A., et al. (2006) "*Hydroacylation of Activated Ketones Catalyzed by N-Heterocyclic Carbenes,*" J. Am. Chem. Soc. 128(14):4558-4559.

European Search Report EP 17875374.5 (dated Aug. 25, 2020) (8 pages).

Georgiev, A.G., et al. (1964) "*The production of β-hydroxy-β-naphthalpropionic esters by means of Reformatsky's reaction,*" Dokl, Akad. Nauk SSSR 154:132-135.

* cited by examiner (A)

(B)

(A)

Normal diet (B)

MCDD (C)

MCDD + H-31

SEQUENCE LISTING

```
<160> NUMBER OF SEQ ID NOS: 1

<210> SEQ ID NO 1
<211> LENGTH: 994
<212> TYPE: DNA
<213> ORGANISM: Homo sapiens
<220> FEATURE:
<221> NAME/KEY: misc_feature
<223> OTHER INFORMATION: Pin1 cDNA

<400> SEQUENCE: 1
tgctggccag cacctcgagg gaagatggcg gacgaggaga agctgccgcc cggctgggag      60
aagcgcatga gccgcagctc aggccgagtg tactacttca accacatcac taacgccagc     120
cagtgggagc ggcccagcgg caacagcagc agtggtggca aaaacgggca gggggagcct     180
gccagggtcc gctgctcgca cctgctggtg aagcacagcc agtcacggcg gccctcgtcc     240
tggcggcagg agaagatcac ccggaccaag gaggaggccc tggagctgat caacggctac     300
atccagaaga tcaagtcggg agaggaggac tttgagtctc tggcctcaca gttcagcgac     360
tgcagctcag ccaaggccag gggagacctg ggtgccttca gcagaggtca gatgcagaag     420
ccatttgaag acgcctcgtt tgcgctgcgg acgggggaga tgagcgggcc cgtgttcacg     480
gattccggca tccacatcat cctccgcact gagtgagggt ggggagccca ggcctggcct     540
cggggcaggg cagggcggct aggccggcca gctcccccctt gcccgccagc cagtggccga     600
accccccact ccctgccacc gtcacacagt atttattgtt cccacaatgg ctgggagggg     660
gcccttccag attgggggcc ctggggtccc cactccctgt ccatccccag ttggggctgc     720
gaccgccaga ttctcccctta aggaattgac ttcagcaggg gtgggaggct cccagaccca     780
gggcagtgtg gtgggagggg tgttccaaag agaaggcctg gtcagcagag ccgccccgtg     840 tcccccagg tgctggaggc agactcgagg gccgaattgt ttctagttag gccacgctcc     900
tctgttcagt cgcaaaggtg aacactcatg cggcagccat gggccctctg agcaactgtg     960
cagacccttt cacccccaat taaacccaga acca                                 994
```

ESTER COMPOUND AND PIN1 INHIBITOR, INFLAMMATORY DISEASE THERAPEUTIC, AND COLON CANCER THERAPEUTIC IN WHICH SAID ESTER COMPOUND IS USED

CROSS-REFERENCE TO RELATED APPLICATIONS

This application is a § 371 Application of PCT/JP2017/042804 (filed on Nov. 29, 2017; pending), which application claims priority to Japanese Patent Application 2016-231875 (filed on Nov. 29, 2016).

TECHNICAL FIELD

The present invention relates to a novel low molecular weight organic compound containing a naphthyl group and an ester bond, and to a Pin1 inhibitor, a pharmaceutical composition, a therapeutic agent or a prophylactic agent for an inflammatory disease such as an inflammatory bowel disease or non-alcoholic steatohepatitis (NASH), and a therapeutic agent or a prophylactic agent for colon cancer, using the compound.

BACKGROUND ART

Inflammatory bowel diseases are diseases that cause chronic inflammation or ulcers in mucosae of the large intestine and the small intestine, and representative examples of such diseases include ulcerative colitis and Crohn's disease. Ulcerative colitis is a disease in which ulcers are formed due to chronic inflammation in the large intestine, and Crohn's disease is a disease in which inflammatory lesions such as ulcers and swelling occur in various sites of the digestive tract. The causes of these diseases are unknown, and they are intractable diseases whose complete cure is difficult.

Development of these diseases often occurs in young persons mainly in their 20s, and there is a remarkable trend toward an increase in the number of patients with these diseases in Japan. Even after once achieving remission, these diseases often repeat recurrence, leading to requirement of total resection of the large intestine. Moreover, these diseases often lead to development of colon cancer after a long period.

For inflammatory bowel diseases, anti-inflammatory agents are applied to mild cases, and steroids or immunosuppressants are applied as the diseases become more severe. In recent years, anti-TNF-α antibodies are also used. However, the anti-inflammatory agents have only weak effects, and the steroids and the immunosuppressants have problems with their systemic side effects. The anti-TNF-α antibodies also have problems with side effects such as immune depression, and with weakened effects. Thus, development of novel therapeutic methods has been strongly demanded for inflammatory bowel diseases.

The present inventors previously discovered that Pin1, which is a cis-trans isomerase, binds to IRS-1, which plays a central role in insulin signaling, to enhance the signaling (Non-patent Document 1).

Pin1 is a peptidyl-prolyl cis-trans isomerase (PPIase), which catalyzes a conformational change in the cis/trans of proline in a protein. Pin1 specifically acts on proline positioned next to phosphorylated serine or threonine, to change the conformation of the proline. Thus, Pin1 is a molecule that links phosphorylation of a protein to a structural change of the protein, and thought to play an important role in intracellular signaling. Regarding Pin1, it has been reported that Pin1 knockout mice exhibit Alzheimer's disease-like symptoms (Non-patent Document 2), and that a Pin1 inhibitor suppresses growth of cancer cells (Non-patent Documents 3 and 4).

As compounds that inhibit Pin1, a phenylalaninol phosphate derivative, an indole or benzimidazole alanine derivative, a fredericamycin A compound, a phenylimidazole derivative, a naphthyl-substituted amino acid derivative, a glutamic acid or aspartic acid derivative, and the like have been reported (Patent Documents 1 to 4 and Non-patent Documents 3 to 6).

The present inventors previously discovered that, by oral administration of

Juglone, which is a compound known as a Pin1 inhibitor and having the following structure:

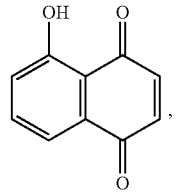

(R)-2-(5-(4-methoxyphenyl)-2-methylfuran-3-carboxamido)-3-(naphthalene-6-yl)propanoic acid (hereinafter referred to as C1), which is a compound similarly known as a Pin1 inhibitor and having the following structure:

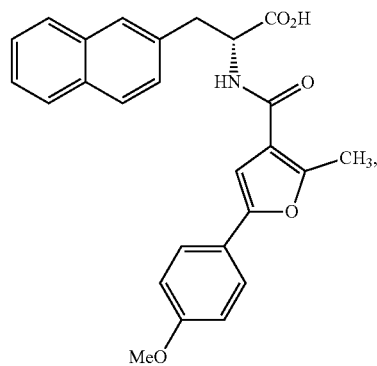

to mice having induced inflammation of the large intestine, development of the inflammation can be suppressed. However, for providing these Pin1 inhibitors as therapeutic agents for inflammatory bowel diseases, prevention of side effects of the Pin1 inhibitors on other organs needs to be achieved (Non-patent Document 7).

Non-patent Documents 8 and 9 describe that a compound as a derivative of 2-hydroxy-3-naphthylpropionic acid was synthesized by enantio-selective asymmetric synthesis, but do not describe at all that the compound has a Pin1 inhibitory action, or that the compound can be a therapeutic agent for an inflammatory bowel disease.

Similarly to inflammatory bowel diseases, non-alcoholic steatohepatitis (NASH) has increased in recent years as an inflammatory disease. Non-alcoholic fatty liver diseases (NAFLD) are diseases in which fat deposition similar to that in alcoholic fatty liver is found due to overeating or the like even without a history of alcohol consumption enough to cause hepatic disorder. These diseases include NASH, which is an advanced disease with serious pathological conditions accompanied by inflammation or fibrosis of liver tissue.

NASH has been found to be a disease that finally proceeds to liver cirrhosis or liver cancer in cases where the disease is left untreated. Therefore, NASH has been recognized as clinically important. However, no therapeutic method has been established for NASH, and dietary therapy is primarily carried out therefor. Regarding a pharmacotherapy, obeticholic acid (6-ethyl-chenodeoxycholic acid), which is a ligand of a famesoid X receptor (FXR), which is a bile acid receptor present in the nuclei of liver cells, has been found to be effective (Patent Document 5), and its clinical trial is being carried out at present.

Thus, development of therapeutic agents effective for inflammatory diseases such as inflammatory bowel diseases and NASH has been required in recent years.

PRIOR ART DOCUMENTS

Patent Documents

[Patent Document 1] WO 2004/087720
[Patent Document 2] WO 2006/040646
[Patent Document 3] WO 2005/007123
[Patent Document 4] WO 2002/060436
[Patent Document 5] WO 2005/089316

Non-Patent Documents

[Non-patent Document 1] Yusuke Nakatsu, Tomoichiro Asano, and 21 other authors. The Journal of Biological Chemistry (J. Biol. Chem.), published on Jun. 10, 2011 (online version: published on Mar. 17, 2011). Vol. 286, No. 23, pp. 20812 to 20822
[Non-patent Document 2] Yih-Cherng Liou and 11 other authors. Nature, published on Jul. 31, 2003. Vol. 424, pp. 556 to 561
[Non-patent Document 3] Andrew Potter and 16 other authors. Bioorganic & Medicinal Chemistry Letters (Bioorg. Med. Chem. Lett.), published on Nov. 15, 2010 (online version: published on Sep. 17, 2010). Vol. 20, No. 22, pp. 6483 to 6488
[Non-patent Document 4] Andrew Potter and 14 other authors. Bioorganic & Medicinal Chemistry Letters (Bioorg. Med. Chem. Lett.), published on Jan. 15, 2010 (online version: published on Nov. 22, 2009). Vol. 20, No. 2, pp. 586 to 590
[Non-patent Document 5] Liming Dong and 11 other authors. Bioorganic & Medicinal Chemistry Letters (Bioorg. Med. Chem. Lett.), published on Apr. 1, 2010 (online version: published on Feb. 14, 2010). Vol. 20, No. 7, pp. 2210 to 2214
[Non-patent Document 6] Hidehiko Nakagawa and 6 other authors. Bioorganic & Medicinal Chemistry Letters (Bioorg. Med. Chem. Lett.), published on Dec. 1, 2015 (online version: published on Oct. 22, 2015). Vol. 25, pp. 5619 to 5624
[Non-patent Document 7] Tomoichiro Asano. "Novel Therapy of Inflammatory Bowel Diseases Using Pin1 Inhibitor". Document distributed in the DSANJ Biz Meeting Categorized by Target Diseases (Digestive Diseases Field), hosted by the Osaka Chamber of Commerce and Industry, published on Jan. 30, 2015
[Non-patent Document 8] Yan Liu and 6 other authors. Journal of the American Chemical Society (J. Am. Chem. Soc.), published online on Oct. 17, 2006. vol. 128, pp. 14212 to 14213
[Non-patent Document 9] Mark J. Burk and 2 other authors. Journal of the American Chemical Society (J. Am. Chem. Soc.), published online on Apr. 28, 1998. vol. 120, pp. 4345 to 4353

SUMMARY OF THE INVENTION

Problems to be Solved by the Invention

In view of the conventional circumstances described above, an object of the present invention is to develop a therapeutic agent for an inflammatory disease such as an inflammatory bowel disease or NASH, which therapeutic agent shows less side effects and high effectiveness.

Means for Solving the Problems

In order to solve the above problem, the present inventors intensively studied to develop a group of novel compounds by synthesizing a large number of derivatives of naphthyl-alkanoic acids containing an ester bond. The present inventors discovered that these novel compounds can be provided as useful therapeutic agents or prophylactic agents for inflammatory bowel diseases since they have an inhibitory activity on the function of Pin1, and since they contain an ester bond, which allows easy degradation of the compounds after acting in the intestine. The present inventors further discovered that these novel compounds also have a therapeutic effect on NASH, can be used as therapeutic agents for a wide range of inflammatory diseases, and can also be used as therapeutic agents or prophylactic agents for colon cancer, thereby completing the present invention.

More specifically, the present invention provides the following first invention related to a novel compound or a salt thereof, the following second invention related to a Pin1 inhibitor, the following third invention related to a pharmaceutical composition, the following fourth invention related to a therapeutic agent or a prophylactic agent for an inflammatory disease accompanied by fibrosis, and the following fifth invention related to a therapeutic agent or a prophylactic agent for colon cancer.

The first invention provides a compound represented by the following Formula (I):

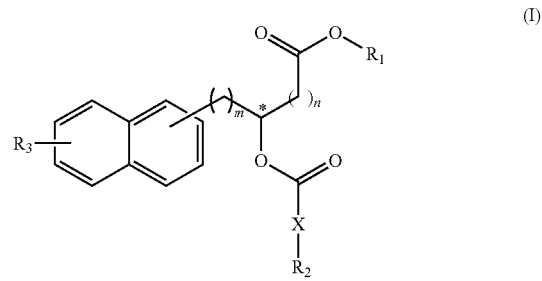

(wherein
m represents an integer of 0 to 3, and n represents an integer of 0 to 2, with the proviso that 1≤m+n≤3;
$R_1$ represents a hydrogen atom, a hydrocarbon group optionally having a substituent(s), a heterocyclic group optionally having a substituent(s), or an amino group optionally having a substituent(s);
$R_2$ represents a polycyclic aryl group optionally having a substituent(s), a heterocyclic group optionally having a substituent(s), an aryloxy group optionally having a substituent(s), a phenyl group having a substituent(s), an aralkyl group having a substituent(s), or a group represented by the following Formula (II):

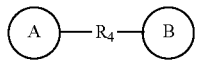

(II)

(wherein Ring A and Ring B each represent a monocyclic or polycyclic aryl group or heterocyclic group optionally having a substituent(s); $R_4$ represents a single bond, a $C_{1-3}$ alkylene group optionally having a substituent(s), a $C_{2-3}$ alkenylene group optionally having a substituent(s), or a divalent oxy group; and the Ring A, Ring B, or $R_4$ moiety is linked to X);

$R_3$ represents 0 to 7 substituent(s) linked to the naphthyl group, each of which substituent(s) is the same or different and has 1 to 10 atoms; and X represents a single bond, a $C_{1-6}$ alkylene group optionally having a substituent(s), a $C_{2-6}$ alkenylene group optionally having a substituent(s), an —$R_5$—NH— group, an —NH—$R_5$— group (wherein $R_5$ represents a $C_{1-5}$ alkylene group optionally having a substituent(s), or a $C_{2-5}$ alkenylene group optionally having a substituent(s)), or a secondary or tertiary amino group)
or a salt thereof.

In the compound or the salt thereof of the first invention, $R_1$ is preferably a hydrogen atom.

In any compound or salt thereof described above, $R_2$ preferably represents a polycyclic aryl group optionally having a substituent(s), a polycyclic heterocyclic group optionally having a substituent(s), a polycyclic aryloxy group optionally having a substituent(s), or a group represented by the following Formula (II):

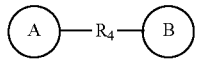

(II)

(wherein Ring A and Ring B each represent a monocyclic or polycyclic aryl group optionally having a substituent(s); $R_4$ represents a $C_{1-3}$ alkylene group optionally having a substituent(s), a $C_{2-3}$ alkenylene group optionally having a substituent(s), or a divalent oxy group; and the Ring A, Ring B, or $R_4$ moiety is linked to X).

In this case, $R_2$ more preferably represents a polycyclic aryl group optionally having a substituent(s), a heterocyclic group containing two or more benzene rings and optionally having a substituent(s), or a polycyclic aryloxy group optionally having a substituent(s).

In any compound or salt thereof described above, the configuration at the asymmetric carbon atom indicated by the symbol "*" is preferably the R configuration.

The second invention provides a Pin1 inhibitor comprising any compound described above or a salt thereof.

The third invention provides a pharmaceutical composition comprising: any compound described above or a pharmaceutically acceptable salt thereof; and a pharmaceutically acceptable carrier.

The fourth invention provides a therapeutic agent or a prophylactic agent for an inflammatory disease accompanied by fibrosis, comprising any compound described above or a pharmaceutically acceptable salt thereof as an effective component.

In the therapeutic agent or the prophylactic agent of the fourth invention, the agent is preferably applied to an inflammatory bowel disease, non-alcoholic steatohepatitis, or pulmonary fibrosis, more preferably applied to an inflammatory bowel disease.

The inflammatory bowel disease herein is, for example, Crohn's disease or ulcerative colitis.

The fourth invention also provides any compound described above or a pharmaceutically acceptable salt thereof for use as a therapeutic agent or a prophylactic agent for an inflammatory disease accompanied by fibrosis.

The fourth invention also provides use of any compound described above or a pharmaceutically acceptable salt thereof for the manufacture of a medicament for the treatment or prevention of an inflammatory disease accompanied by fibrosis.

The fourth invention also provides a method of treatment or prevention of an inflammatory disease accompanied by fibrosis, comprising administering any compound described above to a patient.

The fifth invention provides a therapeutic agent or a prophylactic agent for colon cancer, comprising any compound described above or a pharmaceutically acceptable salt thereof as an effective component.

The fifth invention also provides any compound described above or a pharmaceutically acceptable salt thereof for use as a therapeutic agent or a prophylactic agent for colon cancer.

The fifth invention also provides use of any compound described above or a pharmaceutically acceptable salt thereof for the manufacture of a medicament for the treatment or prevention of colon cancer.

The fifth invention also provides a method of treatment or prevention of colon cancer, comprising administering any compound described above to a patient.

Effect of the Invention

The novel compound or the salt thereof of the first invention can be a compound having an inhibitory activity on the function of Pin1, or a precursor thereof, or a compound that suppresses inflammation of a tissue, or a prodrug thereof. Therefore, the compound or the salt thereof can be used for development of a Pin1 inhibitor, or development of a pharmaceutical for an inflammatory disease or the like.

The Pin1 inhibitor of the second invention has an inhibitory activity on the function of Pin1, or can be changed to a compound having such an activity.

The pharmaceutical composition of the third invention can treat or prevent a disease based on inhibition of the function of Pin1 as an action mechanism.

The therapeutic agent or the prophylactic agent for an inflammatory disease accompanied by fibrosis of the fourth invention can ameliorate or prevent symptoms of an inflammatory disease such as an inflammatory bowel disease or non-alcoholic steatohepatitis (NASH). The therapeutic agent or the prophylactic agent for an inflammatory disease accompanied by fibrosis of the fourth invention contains as an effective component a compound which contains an ester bond and which is hence easily degradable. Therefore, the agent can be easily degraded after oral administration or the like and acting in the digestive tract, so that its blood level is less likely to increase.

The therapeutic agent or the prophylactic agent for colon cancer of the fifth invention can treat or prevent colon cancer by ameliorating inflammation of intestinal tissue and suppressing growth of the cancer. The therapeutic agent or the prophylactic agent for colon cancer of the fifth invention contains as an effective component a compound which has an ester bond and which is hence easily degradable. Therefore, the agent can be easily degraded after oral administration or the like and acting in the digestive tract, so that its blood level is less likely to increase.

BRIEF DESCRIPTION OF THE DRAWINGS

FIG. 4(A) shows a graph showing the result of body weight measurement of each mouse in terms of the ratio (percentage) to the body weight before beginning of administration. FIG. 4(B) shows photographs showing the result of staining of a section of the large intestine of each mouse. In FIGS. 4(A) and (B), "normal" indicates a case where water was administered, and "DSS" indicates cases where DSS-containing water was administered. "non" indicates a case where no compound was administered, and "5-ASA", "H-31", and "H-179" indicate cases where the respective compounds were administered.

FIG. 5(A) shows a graph showing the body weight change in mice subjected to oral administration. FIG. 5(B) shows a graph showing the body weight change in mice subjected to intraperitoneal administration. In FIGS. 5(A) and (B), "normal" indicates a case where water was administered, and "DSS" indicates cases where DSS-containing water was administered. "non" indicates a case where no compound was administered, and "H-31" indicates a case where the compound synthesized in Example 2-7 was administered.

FIG. 6(A) shows a graph showing results of body weight measurement of mice. FIG. 6(B) shows a graph showing results of colon length measurement of mice. FIG. 6(C) shows photographs showing results of staining of a section of the large intestine of each mouse. In FIGS. 6(A) and (B), "300" and "150" indicate cases where "5-ASA" (5-aminosalicylic acid) was administered at doses of "300 mg/kg/day" and "150 mg/kg/day", respectively.

FIG. 7(A) shows results of detection of changes in the Pin1 protein expression level over time in a mouse to which DSS was administered, but to which no compound was administered. FIG. 7(B) shows results of measurement of the Pin1 protein expression level in the intestinal tract after 7 days of administration under each administration condition.

FIG. 8(A) shows a graph showing results of measurement of the blood AST (GOT) level (IU/ml), wherein the bars show, from left to right, measurement results on the blood AST (GOT) levels in control mice, NASH mice fed with MCDD, and NASH mice fed with MCDD to which H-31 was intraperitoneally administered, respectively. FIG. 8(B) shows a graph showing results of measurement of the blood ALT (GPT) level (IU/ml), wherein the bars show, from left to right, measurement results on the blood ALT (GPT) levels in control mice, NASH mice, and NASH mice to which H-31 was intraperitoneally administered, respectively.

FIG. 9(A) shows a photograph showing a result of observation of liver tissue of a control mouse. FIG. 9(B) shows a photograph showing a result of observation of liver tissue of a NASH mouse fed with MCDD. FIG. 9(C) shows a photograph showing a result of observation of liver tissue of a NASH mouse fed with MCDD to which H-31 was intraperitoneally administered.

MODE FOR CARRYING OUT THE INVENTION

Figure 1:
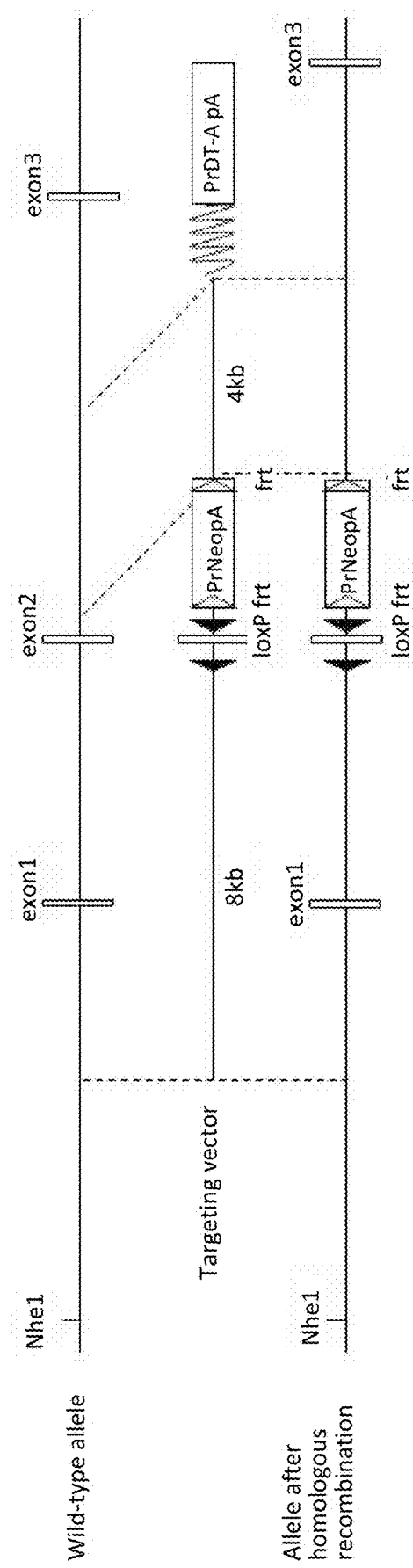
FIG. 1 shows a diagram schematically showing the Pin1 locus, a targeting vector used for preparation of Pin1 knockout mice, and the locus after homologous recombination.

1. Compound or Salt Thereof
1-1. Structure of Compound
The compound of the present invention has a chemical structure represented by the following Formula (I).

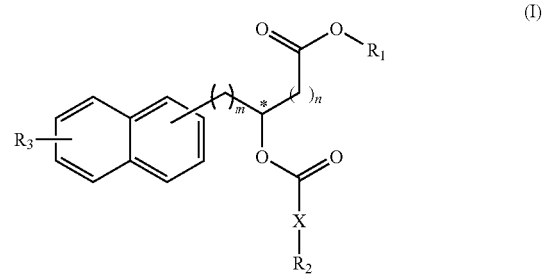

In Formula (I), m represents an integer of 0 to 3, and n represents an integer of 0 to 2, with the proviso that m and n are integers satisfying the following relationship: 1≤m+ n≤3. That is, the combination (m, n) includes the following eight kinds of combinations: (0,1), (0,2), (1,0), (1,1), (1,2), (2,0), (2,1), and (3,0).

The compound of the present invention is composed of a naphthyl moiety and a chain-like moiety linked thereto. The compound may have structures in which the chain-like moiety is linked to an arbitrary portion in the naphthyl group. The structures can be classified into structures in which the chain-like moiety is linked to the 1-position of the naphthyl group, and structures in which the chain-like moiety is linked to the 2-position of the naphthyl group.

In cases where the chain-like moiety is linked to the 2-position of the naphthyl group, the compound of the present invention can have the eight kinds of chemical structures represented by the following Formulae (III) to (X) based on the eight kinds of combinations of (m, n).

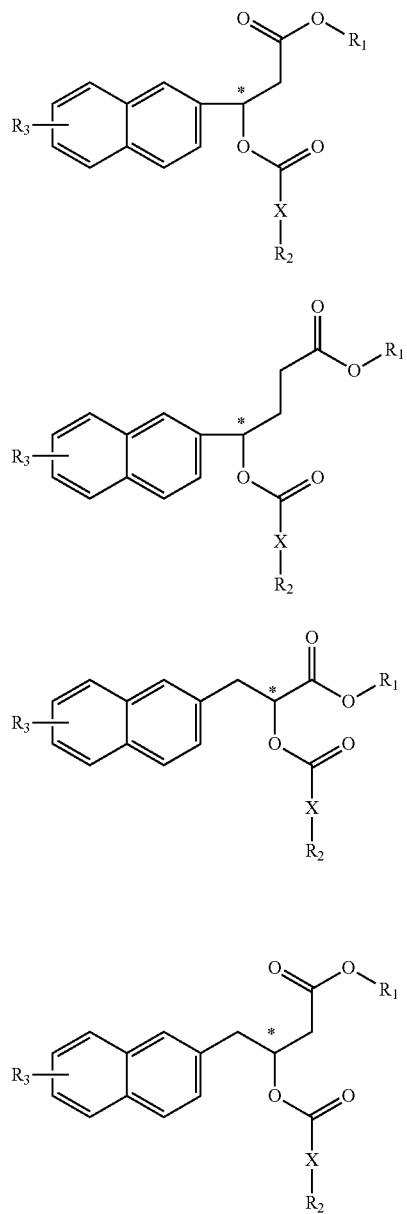

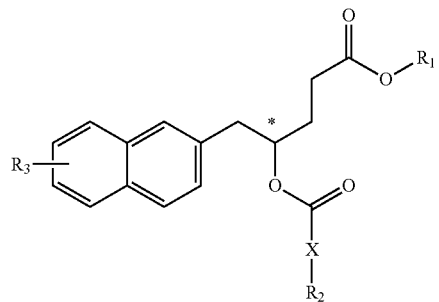

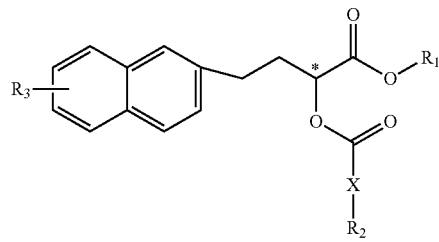

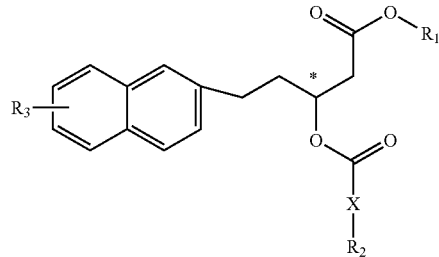

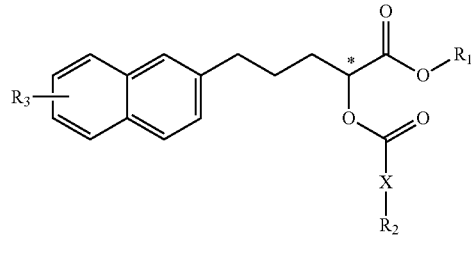

Formula (III) represents the formula for the case where m=0 and n=1 in Formula (I).

Formula (IV) represents the formula for the case where m=0 and n=2 in Formula (I).

Formula (V) represents the formula for the case where m=1 and n=0 in Formula (I).

Formula (I).

Formula (VII) represents the formula for the case where m=1 and n=2 in Formula (I).

Formula (VIII) represents the formula for the case where m=2 and n=0 in Formula (I).

Formula (IX) represents the formula for the case where m=2 and n=1 in Formula (I).

Formula (X) represents the formula for the case where m=3 and n=0 in Formula (I).

In cases where the chain-like moiety is linked to the 1-position of the naphthyl group, the compound of the present invention can similarly have the eight kinds of chemical structures represented by the following Formulae (XII) to (XIX) based on the eight kinds of combinations of (m, n).

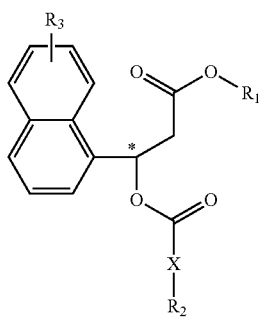

(XII)

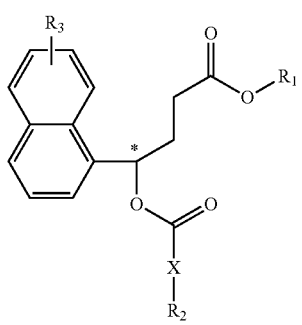

(XIII)

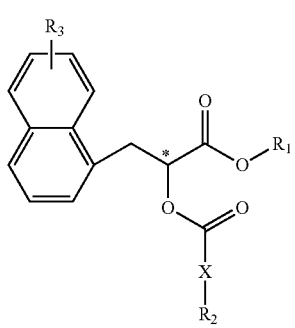

(XIV)

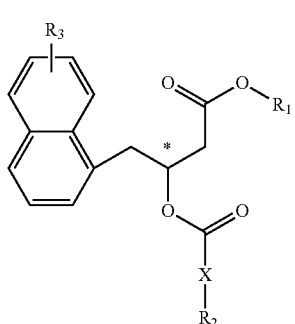

(XV)

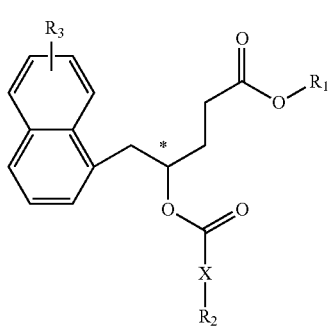

(XVI)

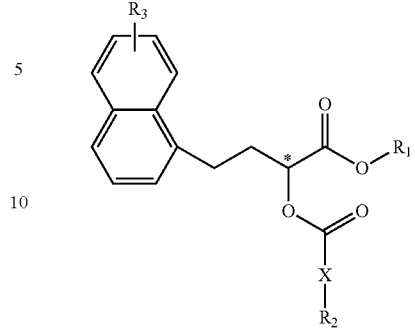

(XVII)

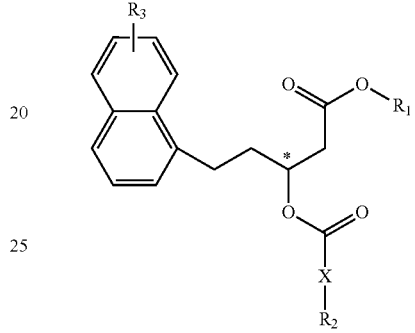

(XIII)

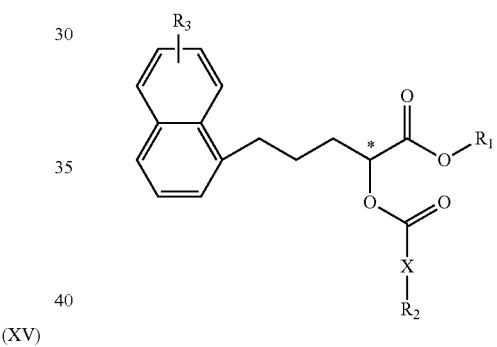

(XIX)

In Formula (I), which represents the compound of the present invention, $R_1$ represents a hydrogen atom, a hydrocarbon group optionally having a substituent(s), a heterocyclic group optionally having a substituent(s), or an amino group optionally having a substituent(s).

The compound of the present invention has an inhibitory activity on the function of Pin1 in cases where $R_1$ is a hydrogen atom and constitutes a carboxyl group. Thus, $R_1$ preferably represents a hydrogen atom.

However, in cases where $R_1$ represents a hydrocarbon group optionally having a substituent(s), a heterocyclic group optionally having a substituent(s), or an amino group optionally having a substituent(s), the compound represented by Formula (I) has an ester bond formed at the $R_1$ moiety, so that a carboxyl group can be formed as a result of hydrolysis. Thus, even in cases where $R_1$ is a hydrocarbon group optionally having a substituent(s), a heterocyclic group optionally having a substituent(s), or an amino group optionally having a substituent(s), the compound of the present invention can be used as a prodrug.

In Formula (I), which represents the compound of the present invention, $R_2$ represents a polycyclic aryl group optionally having a substituent(s), a heterocyclic group optionally having a substituent(s), an aryloxy group optionally having a substituent(s), a phenyl group having a substituent(s), an aralkyl group having a substituent(s), or a group represented by the following Formula (II):

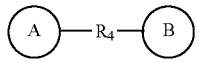
(II)

(wherein Ring A and Ring B each represent a monocyclic or polycyclic aryl group or heterocyclic group optionally having a substituent(s); $R_4$ represents a single bond, a $C_{1-3}$ alkylene group optionally having a substituent(s), a $C_{2-3}$ alkenylene group optionally having a substituent(s), or a divalent oxy group; and the Ring A, Ring B, or $R_4$ moiety is linked to X).

In the compound of the present invention, the naphthyl moiety, the carboxyl moiety, and the $R_2$ moiety are thought to be involved in the inhibitory activity on the function of Pin1. The $R_2$ moiety can have a wide variety of chemical structures containing an aromatic ring or a heterocycle.

In the compound of the present invention, $R_2$ is linked through an ester bond. Therefore, in the body or the like, $R_2$ can be eliminated by hydrolysis of the ester bond, causing the compound to change into a compound having no inhibitory activity on the function of Pin1.

In the Formula (II), Ring A and Ring B are groups linked to each other through $R_4$. Here, $R_4$ may be a single bond. That is, in the group represented by Formula (II), Ring A and Ring B may be directly linked to each other as shown in the following Formula (XXI).

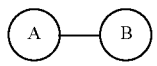
(XXI)

$R_4$ may also be a divalent oxy group. In this case, the group represented by Formula (II) can be represented by the following Formula (XXII).

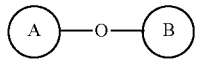
(XXII)

In cases where $R_2$ is a group represented by Formula (II), it is linked to X by linking of the Ring A, Ring B, or $R_4$ moiety to X.

Three structures of the compound of the present invention in cases where $R_2$ is a group represented by Formula (II) are shown by the following Formulae (XXIII) to (XXV).

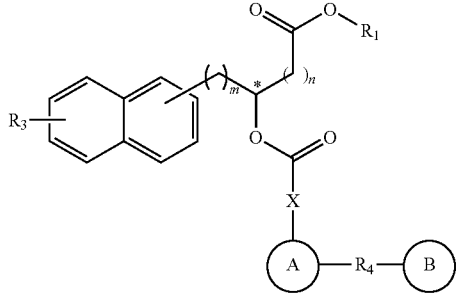
(XXIII)

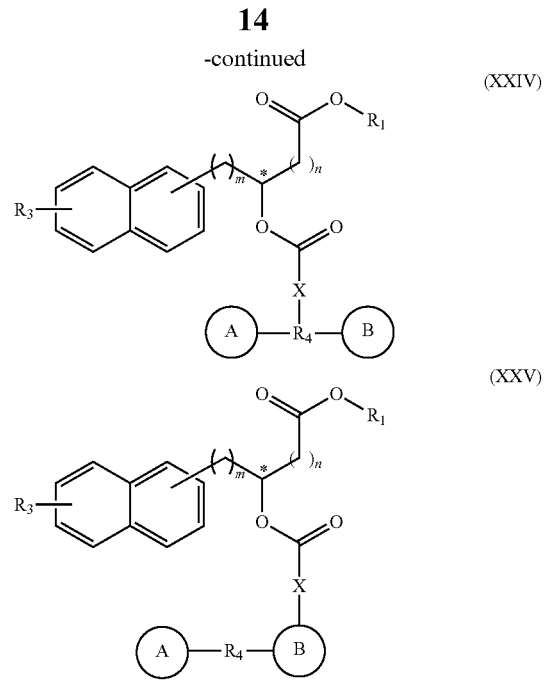
(XXIV)

(XXV)

In Formula (I), which represents the compound of the present invention, $R_3$ represents 0 to 7 substituent(s) linked to the naphthyl group, each of which substituent(s) is the same or different and has 1 to 10 atoms. $R_3$ may be arranged at any of the 1- to 8-positions of the naphthyl group, although $R_3$ cannot be arranged at the position where the chain-like moiety of the compound of the present invention is linked to the naphthyl group. $R_3$ does not need to be arranged on the naphthyl group, and the naphthyl group may be one having no substituent other than the chain-like moiety. In cases where $R_3$ is arranged on the naphthyl group, it may be arranged as 1 to 7 substituents. These substituents may be different from each other, or all or part of the substituents may be the same substituents.

In Formula (I), which represents the compound of the present invention, X represents a single bond, a $C_{1-6}$ alkylene group optionally having a substituent(s), a $C_{2-6}$ alkenylene group optionally having a substituent(s), an —$R_5$—NH— group, an —NH—$R_5$— group (wherein $R_5$ represents a $C_{1-5}$ alkylene group optionally having a substituent(s), or a $C_{2-5}$ alkenylene group optionally having a substituent(s)), or a secondary or tertiary amino group.

X may also be a single bond. In this case, Formula (I) can be represented by the following Formula (XXVI).

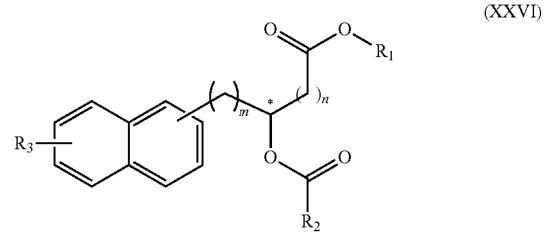
(XXVI)

Since the compound of the present invention has an asymmetric carbon atom at the position indicated by "*", the compound has optical isomers. In the compound of the present invention, the configuration at the asymmetric carbon atom indicated by the symbol "*" may be the R configuration or the S configuration, or the racemic configuration or a configuration in which one of these shows higher abundance. From the viewpoint of simplicity of synthesis and the like, the configuration is preferably the R configuration.

In the present invention, the R configuration and the S configuration are represented according to the Cahn-Ingold-Prelog priority rule.

In the present invention, examples of the "hydrocarbon group" as used for $R_1$ in Formula (I) and the like include, but are not limited to, aliphatic hydrocarbon groups, monocyclic saturated hydrocarbon groups, and aromatic hydrocarbon groups. The hydrocarbon group preferably has 1 to 16 carbon atoms. Specific examples of the hydrocarbon group include, but are not limited to, alkyl, alkenyl, alkynyl, cycloalkyl, aryl, and aralkyl.

Examples of the "alkyl" include alkyl groups such as methyl, ethyl, propyl, isopropyl, butyl, isobutyl, sec-butyl, tert-butyl, pentyl, and hexyl. Examples of the "alkenyl" include alkenyl groups such as vinyl, 1-propenyl, allyl, isopropenyl, butenyl, and isobutenyl. Examples of the "alkynyl" include ethynyl, propargyl, and 1-propynyl. Examples of the "cycloalkyl" include cyclopropyl, cyclobutyl, cyclopentyl, and cyclohexyl. Examples of the "aryl" include phenyl, indenyl, naphthyl, fluorenyl, anthryl, biphenylenyl, phenanthrenyl, as-indacenyl, s-indacenyl, acenaphthylenyl, phenalenyl, fluoranthenyl, pyrenyl, naphthacenyl, and hexacenyl. Examples of the "aralkyl" include benzyl, styryl, and phenethyl.

In the present invention, examples of the "heterocyclic group" as used for $R_1$ and $R_2$ in Formula (I), Ring A and Ring B in Formula (II), and the like include, but are not limited to, 5- to 14-membered monocyclic to pentacyclic heterocyclic groups each containing, in addition to a carbon atom(s), one to four heteroatoms that is/are one or two kinds of atoms each selected from a nitrogen atom, an oxygen atom, and a sulfur atom. Specific examples of the heterocyclic group include, but are not limited to, five-membered cyclic groups each containing, in addition to a carbon atom(s), one to four heteroatoms each selected from an oxygen atom, a sulfur atom, and a nitrogen atom, such as 2- or 3-thienyl, 2- or 3-furyl, 1-, 2-, or 3-pyrrolyl, 1-, 2- or 3-pyrrolidinyl, 2-, 4- or 5-oxazolyl, 3-, 4- or 5-isoxazolyl, 2-, 4- or 5-thiazolyl, 3-, 4- or 5-isothiazolyl, 3-, 4- or 5-pyrazolyl, 2-, 3- or 4-pyrazolidinyl, 2-, 4- or 5-imidazolyl, 1,2,3-triazolyl, 1,2,4-triazolyl, and 1H- or 2H-tetrazolyl. Specific examples of the heterocyclic group also include, but are not limited to, six-membered cyclic groups each containing, in addition to a carbon atom(s), one to four heteroatoms each selected from an oxygen atom, a sulfur atom, and a nitrogen atom, such as 2-, 3-, or 4-pyridyl, N-oxide-2-, 3-, or 4-pyridyl, 2-, 4-, or 5-pyrimidinyl, N-oxide-2-, 4-, or 5-pyrimidinyl, thiomorpholinyl, morpholinyl, piperidino, 2-, 3-, or 4-piperidyl, thiopyranyl, 1,4-oxazinyl, 1,4-thiazinyl, 1,3-thiazinyl, piperazinyl, triazinyl, 3-, or 4-pyridazinyl, pyrazinyl, N-oxide-3-, and 4-pyridazinyl. Specific examples of the heterocyclic group also include, but are not limited to, bicyclic to tetracyclic fused ring groups each containing, in addition to a carbon atom(s), one to four heteroatoms each selected from an oxygen atom, a sulfur atom, and a nitrogen atom, such as indolyl, benzofuryl, benzothiazolyl, benzoxazolyl, xanthenyl, benzimidazolyl, quinolyl, isoquinolyl, phthalazinyl, quinazolinyl, quinoxalinyl, indolizinyl, quinolizinyl, 1,8-naphthyridinyl, dibenzofuranyl, carbazolyl, acridinyl, phenanthridinyl, perimidinyl, phenazinyl, chromanyl, phenothiazinyl, phenoxazinyl, and 7H-pyrazino[2,3-c]carbazolyl.

In the present invention, the "amino group optionally having a substituent(s)" as used for $R_1$ in Formula (I) may be a primary amino group, secondary amino group, or tertiary amino group. The secondary amino group may be an amino group having one substituent. Examples of the secondary amino group include, but are not limited to, alkylamino, arylamino, and alkoxycarbonylamino. The tertiary amino group may be an amino group having two substituents that are the same or different. Examples of the tertiary amino group include, but are not limited to, dialkylamino and diarylamino.

In the present invention, examples of the "aryl" as used for $R_2$ in Formula (I), Ring A and Ring B in Formula (II), and the like include, but are not limited to, phenyl, indenyl, naphthyl, fluorenyl, anthryl, biphenylenyl, phenanthrenyl, as-indacenyl, s-indacenyl, acenaphthylenyl, phenalenyl, fluoranthenyl, pyrenyl, naphthacenyl, and hexacenyl.

Examples of the "polycyclic aryl" as used for $R_2$ in Formula (I) and the like include the above-described aryl groups excluding phenyl. In the present invention, a bicyclic to tetracyclic aryl group is preferably used as the "polycyclic aryl".

In the present invention, the "aryloxy" as used for $R_2$ in Formula (I) and the like is a group in which —O— is linked to the above-described aryl group. Examples of the "aryloxy" include, but are not limited to, phenyloxy and naphthyloxy.

In the present invention, the "aralkyl" as used for $R_2$ in Formula (I) and the like is a group in which an alkyl group is linked to the above-described aryl group. Examples of the "aralkyl" include, but are not limited to, phenylmethyl and 2-phenylethyl.

In the present invention, examples of the "alkylene" as used for $R_4$, $R_5$, X, and the like include, but are not limited to, linear or branched alkylene groups such as methylene, ethylene, ethylidene, propylene, trimethylene, isopropylidene, pentamethylene, and hexamethylene.

Among these, examples of the $C_{1-3}$ alkylene include, but are not limited to, methylene, ethylidene, propylene, trimethylene, and isopropylidene.

In the present invention, examples of the "alkenylene" as used for $R_4$, $R_5$, X, and the like include, but are not limited to, $C_{2-6}$ linear or branched alkenylene groups each having 1 to 3 double bonds, such as vinylene, 1-propenylene, 1-methyl-1-propenylene, 2-methyl-1-propenylene, 2-butenylene, 2-pentenylene, 1,3-butadienylene, 3-dimethyl-1-propenylene, and 1,4-hexadienylene.

Among these, examples of the $C_{2-3}$ alkenylene include, but are not limited to, vinylene, 1-propenylene, and 2-propenylene.

In the present invention, regarding the "secondary or tertiary amino group" as used for X and the like, —NH may be used as the secondary amino group, and —$NR_6$— may be used as the tertiary amino group. Here, $R_6$ represents a substituent.

The "substituent" as used in the present invention is a halogen atom (for example, fluorine, chlorine, bromine, or iodine), alkyl group (for example, a $C_{1-6}$ alkyl group such as methyl, ethyl, propyl, isopropyl, butyl, isobutyl, sec-butyl, tert-butyl, pentyl, or hexyl), cycloalkyl group (for example, a $C_{3-6}$ cycloalkyl group such as cyclopropyl, cyclobutyl, cyclopentyl, or cyclohexyl), alkynyl group (for example, a $C_{2-6}$ alkynyl group such as ethynyl, 1-propynyl, or propargyl), alkenyl group (for example, a $C_{2-6}$ alkenyl group such as vinyl, allyl, isopropenyl, butenyl, or isobutenyl), aralkyl group (for example, a $C_{7-11}$ aralkyl group such as benzyl, α-methylbenzyl, or phenethyl), aryl group (for example, a $C_{6-10}$ aryl group such as phenyl or naphthyl, preferably phenyl), alkoxy group (for example, a $C_{1-6}$ alkoxy group such as methoxy, ethoxy, propoxy, isopropoxy, butoxy, isobutoxy, sec-butoxy, or tert-butoxy), aryloxy group (for example, a $C_{6-10}$ aryloxy group such as phenoxy), alkanoyl group (for example, formyl, or a $C_{1-6}$ alkyl-carbonyl group such as acetyl, propionyl, butyryl, or isobutyryl), arylcarbonyl group (for example, a $C_{6-10}$ arylcarbonyl group such as benzoyl or naphthoyl), alkanoyloxy group (for example, formyloxy, or a $C_{1-6}$ alkyl-carbonyloxy group such as acetyloxy, propionyloxy, butyryloxy, or isobutyryloxy), arylcarbonyloxy group (for example, a $C_{6-10}$ arylcarbonyloxy group such as benzoyloxy or naphthoyloxy), carboxyl group, alkoxycarbonyl group (for example, a $C_{1-6}$ alkoxycarbonyl group such as methoxycarbonyl, ethoxycarbonyl, propoxycarbonyl, isopropoxycarbonyl, butoxycarbonyl, isobutoxycarbonyl, or tert-butoxycarbonyl), aralkyloxycarbonyl group (for example, a $C_{7-11}$ aralkyloxycarbonyl group such as benzyloxycarbonyl), carbamoyl group, halogenoalkyl group (for example, a mono-, di-, or tri-halogeno-$C_{1-4}$ alkyl group such as chloromethyl, dichloromethyl, trifluoromethyl, or 2,2,2-trifluoroethyl), oxo group, amidino group, imino group, amino group, alkylamino group (for example, a mono-$C_{1-4}$ alkylamino group such as methylamino, ethylamino, propylamino, isopropylamino, or butylamino), dialkylamino group (for example, a di-$C_{1-4}$ alkylamino group such as dimethylamino, diethylamino, dipropylamino, diisopropylamino, dibutylamino, or methylethylamino), alkoxycarbonylamino group (for example, a $C_{1-6}$ alkoxycarbonylamino group such as methoxycarbonylamino, isopropoxycarbonylamino, or tert-butoxycarbonylamino), cyclic amino group (a three- to six-membered cyclic amino group that may contain, in addition to a carbon atom(s) and one nitrogen atom, one to three heteroatoms each selected from an oxygen atom, a sulfur atom, and a nitrogen atom, for example, aziridinyl, azetidinyl, pyrrolidinyl, pyrrolinyl, pyrrolyl, imidazolyl, pyrazolyl, imidazolidinyl, piperidyl, morpholinyl, dihydropyridyl, pyridyl, N-methylpiperazinyl, or N-ethylpiperazinyl), alkylenedioxy group (for example, a $C_{1-3}$ alkylenedioxy group such as methylenedioxy or ethylenedioxy), hydroxy group, cyano group, mercapto group, sulfo group, sulfino group, phosphono group, sulfamoyl group, monoalkylsulfamoyl group (for example, a mono-$C_{1-6}$ alkylsulfamoyl group such as N-methylsulfamoyl, N-ethylsulfamoyl, N-propylsulfamoyl, N-isopropylsulfamoyl, or N-butylsulfamoyl), dialkylsulfamoyl group (for example, a di-$C_{1-6}$ alkylsulfamoyl group such as N,N-dimethylsulfamoyl, N,N-diethylsulfamoyl, N,N-dipropylsulfamoyl, or N,N-dibutylsulfamoyl), alkylthio group (for example, a $C_{1-6}$ alkylthio group such as methylthio, ethylthio, propylthio, isopropylthio, butylthio, sec-butylthio, or tert-butylthio), arylthio group (for example, a $C_{6-10}$ arylthio group such as phenylthio or naphthylthio), alkylsulfinyl group (for example, a $C_{1-6}$ alkylsulfinyl group such as methylsulfinyl, ethylsulfinyl, propylsulfinyl, or butylsulfinyl), alkylsulfonyl group (for example, a $C_{1-6}$ alkylsulfonyl group such as methylsulfonyl, ethylsulfonyl, propylsulfonyl, or butylsulfonyl), or arylsulfonyl group (for example, a $C_{6-10}$ arylsulfonyl group such as phenylsulfonyl or naphthylsulfonyl).

In the present invention, the "substituent having 1 to 10 atoms" as used for $R_3$ is a substituent having 1 to 10 atoms among the above-described substituents, and examples of the substituent include, but are not limited to, halogen atoms, methyl, ethyl, vinyl, methoxy, ethoxy, acetyl, carboxyl, methoxycarbonyl, chloromethyl, amino, methylamino, hydroxy, sulfo, and methylthio.

In the present invention, the term "optionally having a substituent" means that the above-described substituent is contained or not contained. In cases where the substituent is contained, two or more substituents may be contained, and these may be the same or different substituents. In the present invention, in cases where the compound of the present invention "optionally has a substituent(s)", the number of the substituent(s) is preferably 0 to 3.

The compound of the present invention has "a . . . group optionally having a substituent(s)" as $R_1$, $R_2$, or X, and $R_3$ represents 0 to 7 substituent(s) linked to the naphthyl group. In cases where these "substituents" are contained, $R_1$ or X preferably has a "substituent". The compound of the present invention more preferably contains none of these "substituents".

1-2. Salt of Compound

The salt of the compound of the present invention may be, for example, a salt with an inorganic base, a salt with an organic base, a salt with an inorganic acid, a salt with an organic acid, or a salt with an acidic or basic amino acid. In cases where the compound of the present invention represented by Formula (I) has an acidic functional group, the compound may be prepared into a salt with an inorganic base, an organic base, or a basic amino acid. In cases where the compound of the present invention represented by Formula (I) has a basic functional group, the compound may be prepared into a salt with an inorganic acid, an organic acid, or an acidic amino acid.

Examples of the salt with an inorganic base include, but are not limited to, sodium salts, potassium salts, and ammonium salts. Examples of the salt with an organic base include, but are not limited to, salts with trimethylamine, ethanolamine, cyclohexylamine, or the like. Examples of the salt with an inorganic acid include, but are not limited to, salts with hydrochloric acid, phosphoric acid, or the like. Examples of the salt with an organic acid include, but are not limited to, salts with acetic acid, phthalic acid, fumaric acid, oxalic acid, or the like. Examples of the salt with an acidic amino acid include, but are not limited to, salts with aspartic acid, glutamic acid, or the like. Examples of the salt with a basic amino acid include salts with arginine or lysine.

1-3. Method of Production of Compound

The compound of the present invention can be synthesize by, for example, the scheme represented by the following reaction formula using a derivative of an amino acid containing a naphthyl group as a material, although the scheme is not limited thereto.

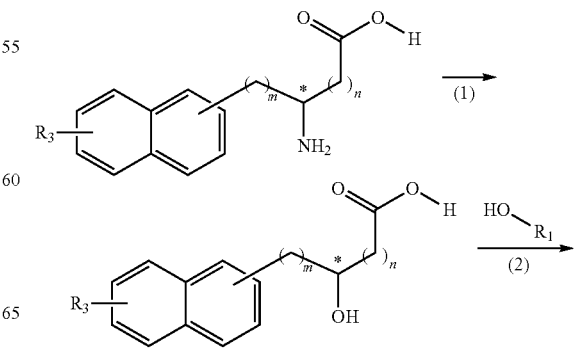

-continued

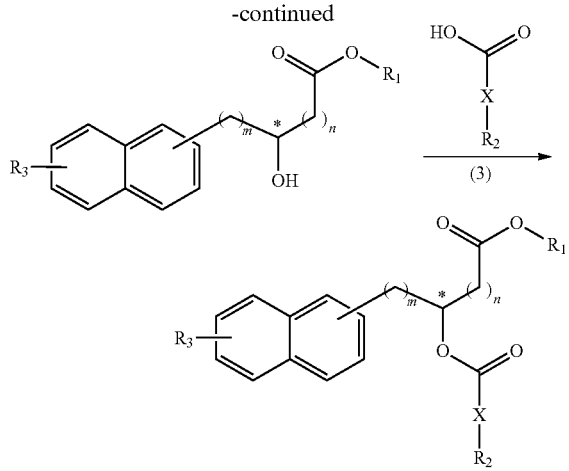

In the above scheme, the reaction (1) is a reaction using an amino acid derivative containing a naphthyl group as a material, wherein the amino group is substituted by a hydroxyl group by a substitution reaction. The reaction (2) is a reaction in which an alcohol having $R_1$ is reacted with the carboxylic acid of a hydroxycarboxylic acid derivative to allow dehydration condensation, to link $R_1$ to the hydroxycarboxylic acid derivative through an ester bond. The reaction (3) is a reaction in which a carboxylic acid having $R_2$ and X is reacted with the hydroxyl group generated by the reaction (1) to allow dehydration condensation, to link X and $R_2$ through an ester bond.

In the above scheme, in cases where a compound having H as $R_1$ is to be synthesized, the compound having H as $R_1$ can be obtained by eliminating $R_1$ by hydrolysis or the like after carrying out the reactions (1) to (3). Alternatively, the compound having H as $R_1$ can be obtained by directly subjecting the hydroxycarboxylic acid derivative to dehydration condensation with the carboxylic acid having $R_2$ and X without carrying out the reaction (2).

2. Pin1 Inhibitor

Pin1 is a peptidyl-prolyl cis-trans isomerase (PPIase), which catalyzes a conformational change in the cis/trans of proline in a protein. Pin1 is an enzyme that specifically acts on proline positioned next to phosphorylated serine or threonine, to change the conformation of the proline.

The Pin1 inhibitor of the present invention is a compound that inhibits the function of Pin1. The Pin1 inhibitor may be a compound represented by Formula (I) described above in 1., or a salt thereof.

In the present invention, "inhibition of the function of Pin1" means inhibition of the isomerase activity of Pin1, and/or inhibition of an activity of Pin1 with which Pin1 binds to or interacts with another protein such as IRS-1.

The Pin1 inhibitor of the present invention has an inhibitory activity on the function of Pin1 in cases where $R_1$ in Formula (I) is a hydrogen atom and constitutes a carboxyl group. Thus, $R_1$ preferably represents a hydrogen atom.

However, in cases where $R_1$ represents a hydrocarbon group optionally having a substituent(s), a heterocyclic group optionally having a substituent(s), or an amino group optionally having a substituent(s), the compound represented by Formula (I) has an ester bond formed at the $R_1$ moiety, so that a carboxyl group can be formed as a result of hydrolysis. Thus, even in cases where $R_1$ is a hydrocarbon group optionally having a substituent(s), a heterocyclic group optionally having a substituent(s), or an amino group optionally having a substituent(s), the compound can be used as a prodrug of a Pin1 inhibitor.

In the Pin1 inhibitor of the present invention, the naphthyl moiety, the carboxyl moiety, and the $R_2$ moiety are thought to be especially involved in the inhibitory activity on the function of Pin1. The $R_2$ moiety can have a wide variety of chemical structures containing an aromatic ring or a heterocycle.

However, since a stronger inhibitory activity on the function of Pin1 can be produced in cases where the $R_2$ moiety has two or more rings or a fused ring, $R_2$ is preferably a polycyclic aryl group optionally having a substituent(s), a polycyclic heterocyclic group optionally having a substituent(s), a polycyclic aryloxy group optionally having a substituent(s), or a group represented by the following Formula (II).

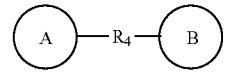

(II)

(In the formula, Ring A and Ring B each represent a monocyclic or polycyclic aryl group optionally having a substituent(s); $R_4$ represents a single bond, a $C_{1-3}$ alkylene group optionally having a substituent(s), a $C_{2-3}$ alkenylene group optionally having a substituent(s), or a divalent oxy group; and the Ring A, Ring B, or $R_4$ moiety is linked to X.)

Specific examples of the group represented by Formula (II) include, but are not limited to, the following groups.

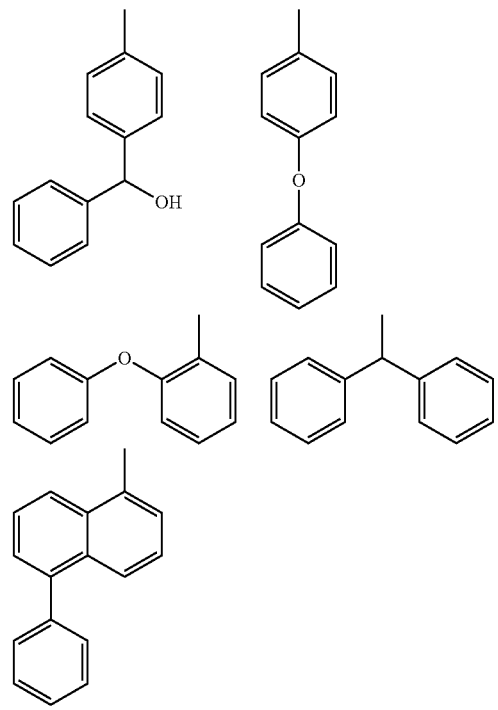

In the Pin1 inhibitor of the present invention, $R_2$ more preferably represents a polycyclic aryl group optionally having a substituent(s), a heterocyclic group containing two or more benzene rings and optionally having a substituent(s), or a polycyclic aryloxy group optionally having a substituent(s).

In this case, the Pin1 inhibitor of the present invention produces a stronger inhibitory activity on the function of Pin1.

R₂ more preferably represents a polycyclic aryl group, a heterocyclic group containing two or more benzene rings, or a polycyclic aryloxy group.

Here, the "polycyclic aryl group optionally having a substituent(s)" is as described above in 1., and specific examples of the group include, but are not limited to, the following groups.

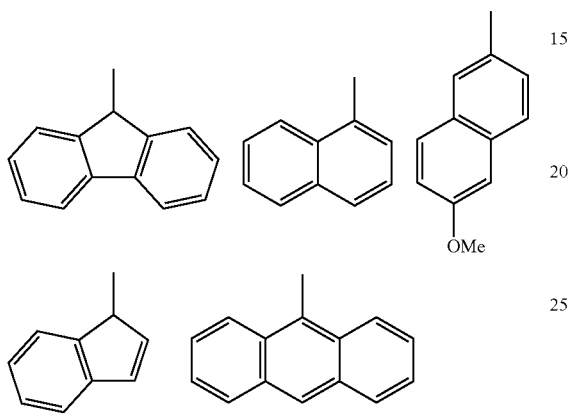

Specific examples of the "polycyclic aryloxy group optionally having a substituent(s)" include, but are not limited to, the following groups.

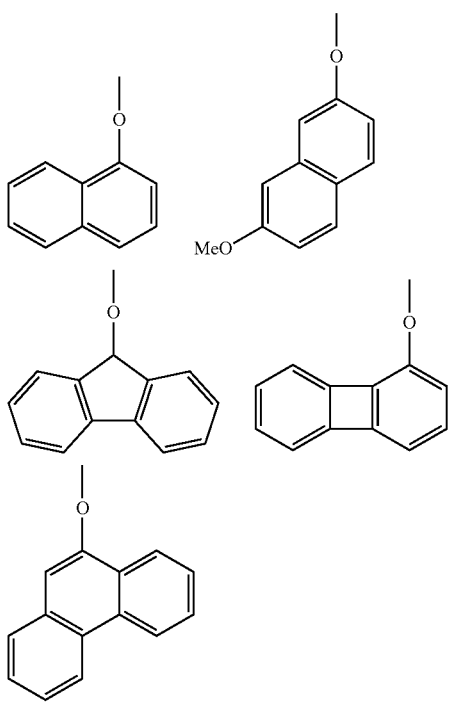

Specific examples of the "heterocyclic group containing two or more benzene rings and optionally having a substituent(s)" include, but are not limited to, the following groups.

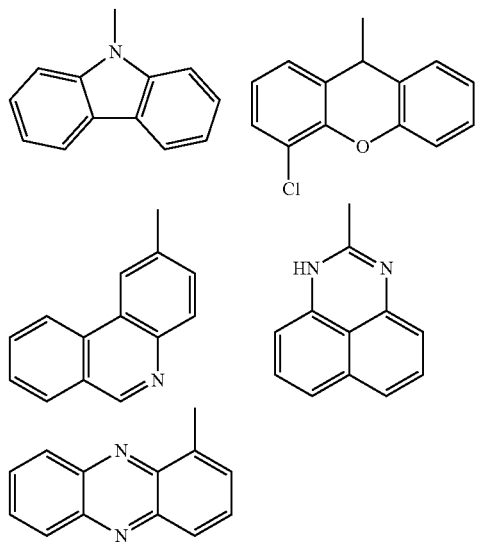

The inhibitory activity of the Pin1 inhibitor of the present invention on the function of Pin1 can be measured, for example, using as an index phosphorylation of AMPK (AMP-activated protein kinase) (see Yusuke Nakatsu et al., Journal of Biological Chemistry, 2015, Vol. 290, No. 40, pp. 24255-24266), although the measurement method is not limited thereto. Alternatively, the inhibitory activity of the Pin1 inhibitor of the present invention on the function of Pin1 can be measured by detecting the isomerase activity of Pin1 using a peptide as a substrate, based on a change in the absorbance (see Hailong Zhao et al., Bioorganic & Medicinal Chemistry, 2016, Vol. 24, pp. 5911-5920). Alternatively, the inhibitory activity of the Pin1 inhibitor of the present invention on the function of Pin1 can be measured by detecting binding to Pin1, which binding competes with that of a substrate peptide (see Shuo Wei et al., Nature Medicine, Vol. 21, No. 5, pp. 457-466, online methods).

3. Pharmaceutical Composition

The pharmaceutical composition of the present invention is a composition containing a compound represented by Formula (I) or a pharmaceutically acceptable salt thereof, and a pharmaceutically acceptable carrier.

The structure of the compound represented by Formula (I) is as described above in 1-1. In cases where the compound has an acidic functional group therein, examples of the pharmaceutically acceptable salt include, but are not limited to, sodium salts, potassium salts, and ammonium salts. In cases where the compound has a basic functional group therein, examples of the pharmaceutically acceptable salt include, but are not limited to, salts with hydrochloric acid, phosphoric acid, acetic acid, phthalic acid, fumaric acid, oxalic acid, or the like.

The pharmaceutical composition of the present invention can be obtained by mixing the compound represented by Formula (I)) or the pharmaceutically acceptable salt thereof with the pharmaceutically acceptable carrier. Examples of the pharmaceutical composition include, but are not limited to, tablets, granules, capsules, powders, solutions, injection solutions, suppositories, patches, eye drops, and inhalants.

As the pharmaceutically acceptable carrier to be used for the pharmaceutical composition of the present invention, various inorganic or organic carrier substances may be used. In cases where the pharmaceutical composition is prepared as a solid formulation such as a tablet or a granule, an excipient, lubricant, binder, disintegrator, and/or the like may be used. In cases where the pharmaceutical composition is prepared as a liquid formulation such as a solution or an injection solution, a solvent, solubilizer, suspending agent, buffer, and/or the like may be used.

In addition, if necessary, additives such as antioxidants, antiseptics, and coloring agents may be used.

Although their examples are not limited, examples of the excipient include lactose, D-mannitol, and starch. Examples of the lubricant include magnesium stearate and talc. Examples of the binder include crystalline cellulose and gelatin. Examples of the disintegrator include carboxymethylcellulose.

Examples of the solvent include distilled water, alcohol, and propylene glycol. Examples of the solubilizer include polyethylene glycol and ethanol. Examples of the suspending agent include stearyltriethanolamine and sodium lauryl sulfate. Examples of the buffer include phosphoric acid salts and acetic acid salts.

The pharmaceutical composition of the present invention can treat or prevent various diseases based on inhibition of the function of Pin1 as an action mechanism.

The compound represented by Formula (I) used for the pharmaceutical composition of the present invention has an inhibitory activity on the function of Pin1 in cases where $R_1$ is a hydrogen atom and constitutes a carboxyl group. Thus, $R_1$ preferably represents a hydrogen atom.

However, in cases where $R_1$ represents a hydrocarbon group optionally having a substituent(s), a heterocyclic group optionally having a substituent(s), or an amino group optionally having a substituent(s), the compound represented by Formula (I) has an ester bond formed at the $R_1$ moiety, so that a carboxyl group can be formed as a result of hydrolysis. Thus, even in cases where $R_1$ is a hydrocarbon group optionally having a substituent(s), a heterocyclic group optionally having a substituent(s), or an amino group optionally having a substituent(s), the compound can be used as a prodrug.

4. Therapeutic Agent/Prophylactic Agent for Inflammatory Disease Accompanied by Fibrosis The therapeutic agent or the prophylactic agent for an inflammatory disease accompanied by fibrosis of the present invention contains a compound represented by Formula (I) or a pharmaceutically acceptable salt thereof as an effective component.

The structure of the compound represented by Formula (I) is as described above in 1-1. The pharmaceutically acceptable salt thereof is as described above in 3.

In the present invention, the inflammatory disease accompanied by fibrosis is a disease that causes fibrosis due to continuous inflammation of a tissue, and includes inflammatory bowel diseases, non-alcoholic steatohepatitis, and pulmonary fibrosis.

In the present invention, "inflammatory bowel diseases" is a general term for diseases that cause chronic inflammation or ulcers in the mucosa of the large intestine or the small intestine. Representative examples of inflammatory bowel diseases include ulcerative colitis and Crohn's disease. Ulcerative colitis is a disease in which ulcers are formed due to chronic inflammation of the large intestine, and Crohn's disease is a disease in which inflammatory lesions such as ulcers and swelling occur in any sites of the digestive tract. An operation is required in cases of occurrence of stenosis due to fibrosis of the intestinal tract caused by an inflammatory bowel disease.

In the present invention, "non-alcoholic steatohepatitis" means a disease also called NASH (Non-Alcoholic Steato-Hepatitis), which is a serious case of a non-alcoholic fatty liver disease, in which fat deposition similar to that in alcoholic hepatitis is found even without a history of alcohol consumption enough to cause hepatic disorder. Non-alcoholic steatohepatitis is known to cause liver cirrhosis, in which death of hepatocytes occurs followed by replacement with fibrous tissue.

In the present invention, "pulmonary fibrosis" is a disease in which chronic inflammation occurs in lung tissue, causing fibrosis and hardening of the inflammatory tissue, by which inflation and expansion/contraction of the lung are prevented.

The therapeutic agent or the prophylactic agent for an inflammatory bowel disease of the present invention may be mixed with a pharmaceutically acceptable carrier as described above in 3., to be prepared into various formulations.

In cases of use as a therapeutic agent or a prophylactic agent for an inflammatory bowel disease, from the viewpoint of allowing the agent to act on the intestine directly, the agent is preferably prepared as a tablet, granule, capsule, powder, solution, or suppository, although the formulation of the agent is not limited thereto.

In cases of use as a therapeutic agent or a prophylactic agent for non-alcoholic steatohepatitis, the agent may be orally administered as a tablet, granule, capsule, powder, solution, or the like, although the formulation of the agent is not limited thereto. From the viewpoint of allowing the agent to act on the liver directly for reduction of side effects, the agent may be prepared as an injection solution, and may be directly administered into the liver through a tube or the like.

In cases of use as a therapeutic agent or a prophylactic agent for pulmonary fibrosis, from the viewpoint of allowing the agent to act on the lung directly, the agent is preferably prepared as an inhalant or the like, although the formulation of the agent is not limited thereto.

Since the therapeutic agent or the prophylactic agent for an inflammatory disease accompanied by fibrosis of the present invention contains a compound represented by Formula (I) or a pharmaceutically acceptable salt thereof as an effective component, the agent can ameliorate or prevent symptoms of an inflammatory bowel disease such as an inflammatory bowel disease or non-alcoholic steatohepatitis, as demonstrated in the later-mentioned Examples 4 to 8. Such a pharmacological effect is thought to be based on an action mechanism in which the compound represented by Formula (I) or the pharmaceutically acceptable salt thereof inhibits the function of Pin1. Since Pin1 is involved in various kinds of signaling in the cell, side effects are also produced. However, $R_2$ in the compound represented by Formula (I) is linked through an ester bond, and the ester bond is easily degraded after oral administration and acting of the compound in the digestive tract, so that the blood level of the compound is less likely to increase. By the elimination of $R_2$, the inhibitory activity on the function of Pin1 disappears, so that the side effects can be reduced. In particular, in cases where the compound is used as a therapeutic agent or a prophylactic agent for an inflammatory bowel disease, the compound can be effectively used by oral administration while suppressing the side effects.

The compound represented by Formula (I) contained as an effective component in the therapeutic agent or the prophylactic agent for an inflammatory disease accompanied by fibrosis of the present invention has an inhibitory activity on the function of Pin1 in cases where $R_1$ is a hydrogen atom and constitutes a carboxyl group. Thus, $R_1$ is preferably a hydrogen atom.

However, in cases where $R_1$ represents a hydrocarbon group optionally having a substituent(s), a heterocyclic group optionally having a substituent(s), or an amino group optionally having a substituent(s), the compound represented by Formula (I) has an ester bond formed at the $R_1$ moiety, so that a carboxyl group can be formed as a result of hydrolysis. Thus, even in cases where $R_1$ is a hydrocarbon group optionally having a substituent(s), a heterocyclic group optionally having a substituent(s), or an amino group optionally having a substituent(s), the compound can be a prodrug to be used for treatment or prevention of an inflammatory disease accompanied by fibrosis.

The compound represented by Formula (I) contained as an effective component in the therapeutic agent or the prophylactic agent for an inflammatory disease accompanied by fibrosis of the present invention can have a wide variety of chemical structures especially in the $R_2$ moiety. Thus, the chemical structure of the therapeutic agent or the prophylactic agent for an inflammatory disease accompanied by fibrosis of the present invention can be modified such that the agent can have appropriate absorbability, distribution characteristics, degradability, excretion properties, and the like.

The therapeutic agent or the prophylactic agent for an inflammatory disease accompanied by fibrosis of the present invention can be administered, as a therapeutic agent or a prophylactic agent, not only to patients diagnosed with an inflammatory disease such as an inflammatory bowel disease, non-alcoholic steatohepatitis, or pulmonary fibrosis, but also to patients with a suspected inflammatory disease, and patients with a risk of development of an inflammatory disease.

The therapeutic agent or the prophylactic agent for an inflammatory disease accompanied by fibrosis of the present invention may be administered preferably at 0.01 to 100 mg, more preferably at 0.1 to 10 mg, in terms of the effective component per day per kg body weight of the patient.

5. Therapeutic Agent or Prophylactic Agent for Colon Cancer

The therapeutic agent or the prophylactic agent for colon cancer of the present invention contains a compound represented by Formula (I) or a pharmaceutically acceptable salt thereof as an effective component.

The structure of the compound represented by Formula (I) is as described above in 1-1. The pharmaceutically acceptable salt thereof is as described above in 3.

The therapeutic agent or the prophylactic agent for colon cancer of the present invention may be mixed with a pharmaceutically acceptable carrier as described above in 3., to be prepared into various formulations. From the viewpoint of allowing the agent to act on the intestine directly, the agent is preferably prepared as a tablet, granule, capsule, powder, solution, or suppository.

The therapeutic agent or the prophylactic agent for colon cancer of the present invention can treat or prevent colon cancer by ameliorating inflammation of intestinal tissue. It is known that inflammation of intestinal tissue for a long period often leads to development of colon cancer. Therefore, the agent is especially useful as a prophylactic agent. The agent is also useful as a therapeutic agent for colon cancer since it is effective for ameliorating inflammation of intestinal tissue, and moreover, as demonstrated in the later-mentioned Example 9, it is effective for suppressing growth of cancer.

The prophylactic agent for colon cancer of the present invention may be administered to a patient with a risk of development of colon cancer. Here, examples of the patient with a risk of development of colon cancer include, but are not limited to, patients with familial polyposis coli, Lynch syndrome, MUTYH-associated polyposis coli, Peutz-Jeghers syndrome, juvenile polyposis, Cowden disease, Crohn's disease, ulcerative colitis, or Cronkhite-Canada syndrome.

The therapeutic agent or the prophylactic agent for colon cancer of the present invention may be administered preferably at 0.01 to 100 mg, more preferably at 0.1 to 10 mg, in terms of the effective component per day per kg body weight of the patient.

The therapeutic agent or the prophylactic agent for colon cancer of the present invention contains a compound represented by Formula (I) or a pharmaceutically acceptable salt thereof as an effective component, and one of its action mechanisms is based on inhibition of the function of Pin1. Here, since Pin1 is involved in various kinds of signaling in the cell, the prophylactic agent or the therapeutic agent of the present invention containing a Pin1 inhibitor is thought to have side effects. However, $R_2$ in the compound represented by Formula (I) is linked through an ester bond, and the ester bond is easily degraded after oral administration and acting of the compound in the digestive tract, so that the blood level of the compound is less likely to increase. By the elimination of $R_2$, the inhibitory activity on the function of Pin1 disappears, so that side effects in tissues other than the digestive tract can be reduced.

The compound represented by Formula (I) contained as an effective component in the therapeutic agent or the prophylactic agent for colon cancer of the present invention has an inhibitory activity on the function of Pin1 in cases where $R_1$ is a hydrogen atom and constitutes a carboxyl group. Thus, $R_1$ is preferably a hydrogen atom.

However, in cases where $R_1$ represents a hydrocarbon group optionally having a substituent(s), a heterocyclic group optionally having a substituent(s), or an amino group optionally having a substituent(s), the compound represented by Formula (I) has an ester bond formed at the $R_1$ moiety, so that a carboxyl group can be formed as a result of hydrolysis. Thus, even in cases where $R_1$ is a hydrocarbon group optionally having a substituent(s), a heterocyclic group optionally having a substituent(s), or an amino group optionally having a substituent(s), the compound can be a prodrug to be used for treatment or prevention of colon cancer.

The compound represented by Formula (I) contained as an effective component in the therapeutic agent or the prophylactic agent for colon cancer of the present invention can have a wide variety of chemical structures especially in the $R_2$ moiety. Thus, the chemical structure of the therapeutic agent or the prophylactic agent for colon cancer of the present invention can be modified such that the agent can have appropriate absorbability, distribution characteristics, degradability, excretion properties, and the like.

6. Therapeutic Agent/Prophylactic Agent for Inflammatory Disease or Colon Cancer Containing Pin1 Inhibitor as Effective Component The present invention provides a therapeutic agent or a prophylactic agent for an inflammatory disease or colon cancer containing a Pin1-specific inhibitor.

Here, as the Pin1-specific inhibitor, an organic compound that specifically acts on Pin1, an antibody or an aptamer that specifically binds to Pin1, or a siRNA that suppresses expression of Pin1 may be used.

As the organic compound that specifically acts on Pin1, not only the compound represented by Formula (I), but also the compounds described in Patent Documents 1 to 4 and Non-patent Documents 3 to 6 may be used.

The antibody that specifically binds to Pin1 can be obtained by, for example, an ordinary method for preparation of a monoclonal antibody or a polyclonal antibody. In a typical method of preparing a monoclonal antibody, an antigen is prepared and mixed with an adjuvant, followed by a plurality of times of inoculation of the resulting mixture to an animal such as a mouse, rat, or rabbit, and then collection of the spleen or lymph nodes of the animal. Lymphocytes are collected from the spleen or the lymph nodes, and the collected lymphocytes are fused with myeloma cells to obtain hybridomas. These hybridomas are screened for a hybridoma producing an antibody having the specificity of interest, and the selected hybridoma line is cloned. By purifying culture supernatant of the cloned hybridoma, the monoclonal antibody of interest can be obtained.

The aptamer that specifically binds to Pin1 can be obtained by, for example, screening by the SELEX (Systematic Evolution of Ligands by EXponential enrichment) method. In the SELEX method, a nucleic acid library containing random sequence regions inserted between primer-binding sequences is provided. Each nucleic acid contained in the library forms a three-dimensional structure, and can be a nucleic acid having a binding capacity to a particular substance. By subjecting a solution of this initial library to chromatography using a column to which a target substance is immobilized, a fraction having a binding capacity to the target substance can be obtained. The obtained fraction is amplified by PCR, and then subjected again to the chromatography. By repeating this process, an aptamer can be obtained as a nucleic acid that strongly binds to the target substance.

A siRNA (small interfering RNA) that suppresses expression of Pin1 can be obtained by synthesizing a 20- to 30-base double-stranded RNA based on the gene sequence of Pin1. The 3' portion of each RNA chain preferably has a two-base-protruding structure. The siRNA is incorporated into a protein complex called RISC (RNA-induced silencing complex). The RISC uses the siRNA as a guide for finding the target, and binds to the target RNA to degrade the target RNA. This is called RNAi (RNA interference), and enables suppression of expression of the gene of interest. The siRNA can be introduced into the cell using a drug delivery system, or can be expressed in the cell using a vector.

The gene sequence of Pin1 for designing the siRNA that suppresses expression of Pin1 is shown in the later-described SEQUENCE LISTING The present invention is described below in detail by way of Examples. However, the present invention is not limited thereto.

Example 1

(DSS-Induced Ulcerative Colitis Using Pin1-Knockout Mice)

Pin1 knockout mice (Pin1 KO mice) were prepared using the Cre-loxP system. A sequence containing exon 2 of the Pin1 gene was sandwiched between loxP sequences, and the resulting sequence and the Neo gene were sandwiched between 5'- and 3'-sequences of the Pin1 gene. The diphtheria toxin A subunit (DTA) gene was bound to the 3'-end of the resulting sequence to prepare a targeting vector (FIG. 1). The targeting vector was introduced into ES cells (TT2 cells) by electroporation, and screening was carried out for positive clones by PCR and Southern blotting. Chimeric mice were prepared using a positive clone, and the chimeric mice were crossed with C57BL/6J mice, to obtain Pin1 flox mice. By crossing the Pin1 flox mice with CAG-Cre mice, Pin1 KO mice were obtained.

Female wild-type mice (C57BL/6 mice) and Pin1 KO mice of 10 weeks old were subjected to administration of 3% DSS (dextran sulfate sodium)-containing water or water (control) by allowing the mice to drink it for 7 days. On Day 7 after the beginning of the administration, the large intestine was removed from each mouse, and subjected to histological study.

Figure 2:
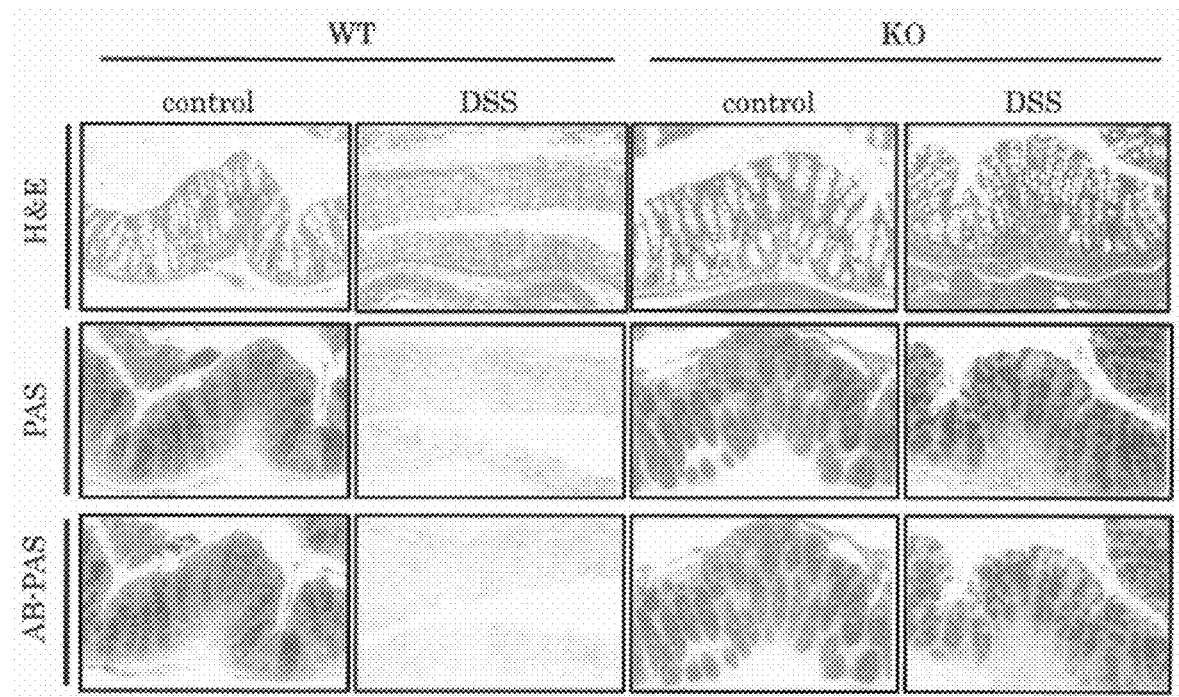
FIG. 2 shows photographs presented instead of a drawing showing results of histological study of the large intestines of wild-type mice (WT) and Pin1 knockout mice (KO). Micrographs for wild-type mice and knockout mice to which control (water) or DSS (dextran sulfate sodium) was administered, which micrographs were taken after H&E staining (hematoxylin-eosin staining) (top row), PAS staining (middle row), or AB-PAS staining (bottom row), are shown.

The results are shown in FIG. 2. FIG. 2 shows micrographs for wild-type mice (WT) and knockout mice (KO) to which control (water) or DSS (dextran sulfate sodium) was administered, which micrographs were taken after H&E staining (hematoxylin-eosin staining) (top row), PAS staining (middle row), or AB-PAS staining (bottom row). In the wild-type mice, administration of DSS caused colitis, and the tissue of the large intestine was found to be damaged. In contrast, in the Pin1 KO mice, development of colitis due to the administration of DSS was suppressed. Further, in the Pin1 KO mice, a tissue-protecting effect could be observed. For example, tissue damage in the large intestine was suppressed, and goblet cells were maintained (FIG. 2).

It was thus shown that resistance to development of ulcerative colitis can be acquired by inhibition of the function of Pin1.

Example 2

(Example 2-1) Synthesis of Intermediate

An intermediate for synthesis of the compound of the present invention was synthesized.

First, D-naphthylalanine was used as a starting substance, and a reaction to substitute the amino group with a hydroxy group was carried out.

To a suspension of D-naphthylalanine (10.3 g, 47.9 mmol) in water (40 mL), 1 M sulfuric acid (60 mL) and acetone (160 mL) were added at room temperature, and the resulting mixture was cooled to −5° C., followed by slowly adding a solution of sodium nitrite (9.9 g, 144 mmol) in water (40 mL) thereto. The resulting mixture was stirred at −5° C. for 30 minutes, and then further stirred at room temperature for 16 hours. After removing acetone under reduced pressure, the mixture was extracted with ethyl acetate. The organic layer was washed with saturated brine, and then dried over anhydrous magnesium sulfate, followed by filtration, and concentration under reduced pressure, to obtain the compound represented by the following structural formula (H-18). This compound was used for the subsequent step without purification.

(H-18)

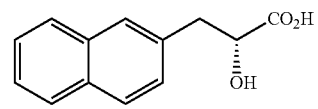 [SMILES: O=C(O)[C@H](O)Cc1ccc2ccccc2c1]

A solution of a crude product of H-18, benzylalcohol (5.18 g, 4.9 mL, 47.9 mmol), and p-toluenesulfonic acid monohydrate (912 mg, 4.8 mmol) in benzene (150 mL) was refluxed, and stirred for 8 hours while performing azeotropic dehydration. After cooling the mixture to room temperature, a saturated sodium hydrogen carbonate solution was added thereto, followed by extraction with ethyl acetate. The organic layer was washed with saturated brine, and then dried over anhydrous magnesium sulfate, followed by filtration, and concentration under reduced pressure. The resulting residue was purified by silica gel column chromatography (hexane:ethyl acetate, 4:1), to obtain the compound represented by the following structural formula (H-26) as white crystals (11.7 g, 38.3 mmol, 80%). The crystals were dissolved in ether, and then left to stand to allow precipitation of crystals, followed by filtration and washing of the crystals with a mixed solvent of hexane:ether (4:1).

Regarding H-26, the NMR measurement spectrum and the result of mass spectrometry by HR-ESI-MS were as follows.

$^1$H NMR (400 MHz, CDCl$_3$) δ 3.16 (1H, dd, J=13.7, 6.4 Hz), 3.30 (1H, dd, J=13.7, 4.6 Hz), 4.59 (1H, dd, J=6.4, 4.6 Hz), 5.16 (1H, d, J=12.3 Hz), 5.21 (1H, d, J=12.3 Hz), 7.26-7.39 (6H, m), 7.42-7.49 (2H, m), 7.62 (1H, s), 7.71-7.76 (2H, m), 7.78-7.83 (1H, m); $^{13}$C NMR (100 MHz, CDCl$_3$) δ 40.6, 67.4, 71.3, 125.5, 126.0, 126.9, 127.6, 127.7, 128.0, 128.2, 128.5, 128.6, 132.4, 133.4, 133.7, 134.9, 173.9; HRESIMS calcd for C$_{20}$H$_{18}$O$_3$Na [M+Na]$^+$ 329.1154, found 329.1151.

The chemical structure of H-26 found was as follows.
(H-26)

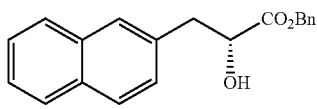 [SMILES: O=C(OCc1ccccc1)[C@H](O)Cc1ccc2ccccc2c1]

(Example 2-2) Synthesis of H-13

To a solution of H-26 (100 mg, 0.327 mmol), 4-benzoylbenzoic acid (89 mg, 0.392 mmol), and 4-dimethylaminopyridine (4.0 mg, 0.033 mmol) in dichloromethane (3 mL), 1-ethyl-3-(3-dimethylaminopropyl)carbodiimide hydrochloride (82 mg, 0.425 mmol) was added at room temperature, and the resulting mixture was stirred at the same temperature for 16 hours. Water was added to the mixture, and extraction was carried out with ethyl acetate. The organic layer was washed with saturated brine, and then dried over anhydrous magnesium sulfate, followed by filtration, and concentration under reduced pressure. The resulting residue was purified by silica gel column chromatography (hexane:ethyl acetate, 5:1), to obtain H-13 as white crystals (141 mg, 0.274 mmol, 84%).

Regarding H-13, the NMR measurement spectrum and the result of mass spectrometry by HR-ESI-MS were as follows.

$^1$H NMR (400 MHz, CDCl$_3$) δ 3.47 (1H, dd, J=14.6, 7.8 Hz), 3.52 (1H, dd, J=14.6, 5.4 Hz), 5.18 (1H, d, J=12.3 Hz), 5.23 (1H, d, J=12.3 Hz), 5.66 (1H, dd, J=7.8, 5.4 Hz), 7.22-7.35 (5H, m), 7.41 (1H, dd, J=8.3, 1.4 Hz), 7.43-7.54 (4H, m), 7.62 (1H, t, J=7.3 Hz), 7.72 (1H, s), 7.73-7.87 (7H, m), 8.14 (2H, d, J=8.3 Hz); $^{13}$C NMR (100 MHz, CDCl$_3$) δ 37.5, 67.3, 73.7, 125.8, 126.2, 127.4, 127.57, 127.61, 128.1, 128.21, 128.24, 128.4, 128.5, 129.69, 129.71, 130.1, 132.3, 132.5, 132.9, 133.0, 133.4, 135.0, 136.8, 141.6, 165.1, 169.2, 195.9; HRESIMS calcd for C$_{34}$H$_{26}$O$_5$Na [M+Na]$^+$ 537.1678, found 537.1681.

The chemical structure of H-13 found was as follows.
(H-13)

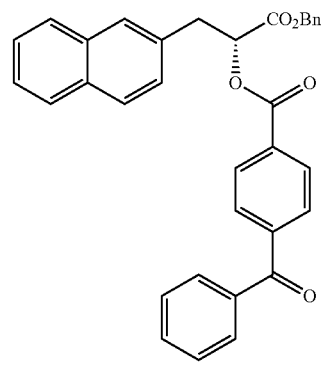 [SMILES: O=C(O[C@H](Cc1ccc2ccccc2c1)C(=O)OCc1ccccc1)c1ccc(C(=O)c2ccccc2)cc1]

(Example 2-3) Synthesis of H-23

To a mixed solution of H-13 (114 mg, 0.222 mmol) in THF (2 mL) and ethanol (2 mL), Pd/C ethylenediamine complex (100 mg) was added, and the resulting mixture was stirred under hydrogen atmosphere at room temperature for 16 hours. The reaction mixture was filtered using Celite, and the residue was washed with ethyl acetate, followed by concentration of the solution under reduced pressure, to obtain H-23 as yellow crystals (90 mg, 0.454 mmol, 95%).

Regarding H-23, the NMR measurement spectrum and the result of mass spectrometry by HR-ESI-MS were as follows.

$^1$H NMR (400 MHz, CDCl$_3$) δ 3.33-3.55 (2H, m), 5.51 (1H, bs), 5.80 (1H, s), 7.22-7.50 (9H, m), 7.71-7.82 (5H, m), 7.92 (2H, d, J=7.7 Hz); $^{13}$C NMR (100 MHz, CDCl$_3$) δ 37.4, 73.3, 75.8, 125.7, 126.1, 126.4, 126.6, 127.4, 127.6, 127.9, 128.08, 128.11, 128.16, 128.3, 128.4, 128.6, 129.69, 129.73, 130.0, 130.1, 132.4, 133.4, 142.9, 149.3, 165.8, 174.4; HRESIMS calcd for C$_{27}$H$_{22}$O$_5$Na [M+Na]$^+$ 449.1365, found 449.1367.

The chemical structure of H-23 found was as follows.
(H-23)

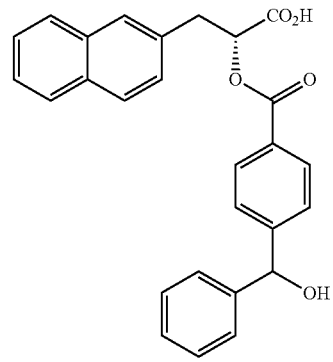 [SMILES: O=C(O[C@H](Cc1ccc2ccccc2c1)C(=O)O)c1ccc(C(O)c2ccccc2)cc1]

(Example 2-4) Synthesis of H-21

To a solution of H-26 (150 mg, 0.49 mmol), naphthalene-2-carboxylic acid (101 mg, 0.588 mmol), and 4-dimethylaminopyridine (6.0 mg, 0.049 mmol) in dichloromethane (5 mL), 1-ethyl-3-(3-dimethylaminopropyl)carbodiimide hydrochloride (122 mg, 0.64 mmol) was added at room temperature, and the resulting mixture was stirred at the same temperature for 8 hours. Water was added to the mixture, and extraction was carried out with ethyl acetate. The organic layer was washed with saturated brine, and then dried over anhydrous magnesium sulfate, followed by filtration, and concentration under reduced pressure. The resulting residue was purified by silica gel column chromatography (hexane:ethyl acetate, 6:1), to obtain H-21 as white crystals (217 mg, 0.472 mmol, 96%).

Regarding H-21, the NMR measurement spectrum and the result of mass spectrometry by HR-ESI-MS were as follows.

$^1$H NMR (400 MHz, CDCl$_3$) δ 3.48-3.58 (2H, m), 5.19 (1H, d, J=12.3 Hz), 5.24 (1H, d, J=12.3 Hz), 5.70 (1H, t, J=6.0 Hz), 7.22-7.35 (4H, m), 7.43-7.65 (5H, m), 7.75-8.08 (9H, m), 8.61 (1H, s); $^{13}$C NMR (100 MHz, CDCl$_3$) δ 37.6, 67.1, 73.5, 125.1, 125.3, 125.7, 126.1, 126.6, 127.1, 127.47, 127.57, 127.61, 127.69, 127.9, 128.2, 128.3, 128.4, 128.5, 128.8, 129.2, 129.4, 129.6, 131.5, 132.3, 132.5, 132.7, 133.2, 133.4, 135.1, 135.7, 166.0, 169.5; HRESIMS calcd for C$_{31}$H$_{24}$O$_4$Na [M+Na]$^+$ 483.1572, found 483.1573.

The chemical structure of H-21 found was as follows.
(H-21)

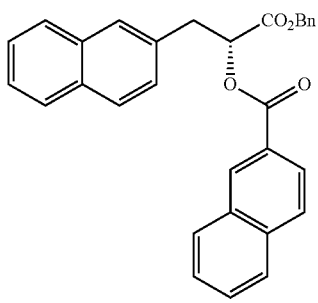 [SMILES: O=C(O[C@H](Cc1ccc2ccccc2c1)C(=O)OCc1ccccc1)c1ccc2ccccc2c1]

(Example 2-5) Synthesis of H-30

To a solution of H-21 (197 mg, 0.478 mmol) in THF (6 mL), 5% Pd/C (100 mg) was added, and the resulting mixture was stirred under hydrogen atmosphere at room temperature for 16 hours.

The reaction mixture was filtered using Celite, and the residue was washed with ethyl acetate, followed by concentration of the solution under reduced pressure, to obtain H-30 as white crystals (150 mg, 0.405 mmol, 95%).

Regarding H-30, the NMR measurement spectrum and the result of mass spectrometry by HR-ESI-MS were as follows.

$^1$H NMR (400 MHz, CDCl$_3$) δ 3.51 (1H, dd, J=14.2, 8.3 Hz), 3.57 (1H, dd, J=14.2, 4.6 Hz), 5.66 (1H, dd, J=8.3, 4.6 Hz), 7.42-7.63 (5H, m), 7.78-7.92 (7H, m), 8.02 (1H, dd, J=8.3, 1.8 Hz), 8.57 (1H, s); $^{13}$C NMR (100 MHz, CDCl$_3$) δ 37.5, 73.1, 125.1, 125.8, 126.2, 126.3, 126.7, 127.4, 127.61, 127.65, 127.73, 128.2, 128.5, 129.4, 131.6, 132.3, 132.5, 133.3, 133.5, 135.7, 166.1, 174.8; HRESIMS calcd for C$_{24}$H$_{18}$O$_4$Na [M+Na]$^+$ 393.1103, found 393.1104.

The chemical structure of H-30 found was as follows.
(H-30)

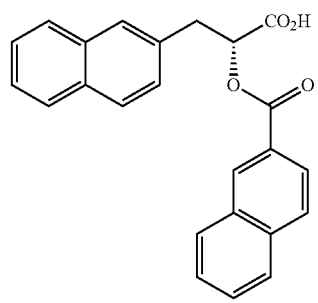 [SMILES: O=C(O[C@H](Cc1ccc2ccccc2c1)C(=O)O)c1ccc2ccccc2c1]

(Example 2-6) Synthesis of H-22

To a solution of H-26 (150 mg, 0.49 mmol), fluorene-9-carboxylic acid (124 mg, 0.588 mmol), and 4-dimethylaminopyridine (6.0 mg, 0.049 mmol) in dichloromethane (5 mL), 1-ethyl-3-(3-dimethylaminopropyl)carbodiimide hydrochloride (122 mg, 0.64 mmol) was added at room temperature, and the resulting mixture was stirred at the same temperature for 8 hours. Water was added to the mixture, and extraction was carried out with ethyl acetate. The organic layer was washed with saturated brine, and then dried over anhydrous magnesium sulfate, followed by filtration, and concentration under reduced pressure. The resulting residue was purified by silica gel column chromatography (hexane:ethyl acetate, 6:1), to obtain H-22 as pale yellow crystals (191 mg, 0.384 mmol, 78%).

Regarding H-22, the NMR measurement spectrum and the result of mass spectrometry by HR-ESI-MS were as follows.

$^1$H NMR (400 MHz, CDCl$_3$) δ 3.26 (1H, dd, J=14.2, 8.7 Hz), 3.45 (1H, dd, J=14.2, 4.1 Hz), 4.85 (1H, s), 5.12 (1H, d, J=12.3 Hz), 5.19 (1H, d, J=12.3 Hz), 5.44 (1H, dd, J=8.7, 4.1 Hz), 7.02 (1H, td, J=7.3, 0.9 Hz), 7.12-7.21 (5H, m), 7.26-7.40 (5H, m), 7.43-7.53 (3H, m), 7.55 (1H, s), 7.66-7.73 (4H, m), 7.80-7.85 (1H, m); $^{13}$C NMR (100 MHz, CDCl$_3$) δ 37.3, 53.0, 67.2, 73.6, 119.86, 119.88, 125.5, 125.6, 125.7, 126.0, 127.2, 127.3, 127.6, 127.7, 128.0, 128.12, 128.16, 128.19, 128.3, 128.4, 128.5, 133.1, 133.3, 135.0, 140.0, 140.1, 141.3, 141.4, 169.1, 170.5; HRESIMS calcd for C$_{34}$H$_{26}$O$_4$Na [M+Na]$^+$ 521.1729, found 521.1732.

The chemical structure of H-22 found was as follows.
(H-22)

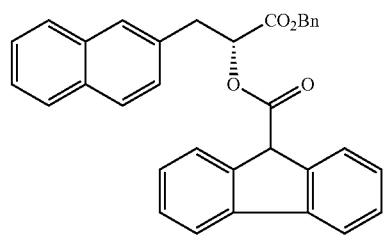 [SMILES: O=C(O[C@H](Cc1ccc2ccccc2c1)C(=O)OCc1ccccc1)C1c2ccccc2-c2ccccc21]

(Example 2-7) Synthesis of H-31

To a solution of H-22 (188 mg, 0.377 mmol) in THF (6 mL), 5% Pd/C (100 mg) was added, and the resulting mixture was stirred under hydrogen atmosphere at room temperature for 16 hours. The reaction mixture was filtered using Celite, and the residue was washed with ethyl acetate, followed by concentration of the solution under reduced pressure, to obtain H-31 as white gel (140 mg, 0.343 mmol, 91%) (>99% ee, AD-H column, hexane:isopropanol, 5:1).

Regarding H-31, the specific rotation, the IR spectrum, the NMR measurement spectrum, and the result of mass spectrometry by HR-ESI-MS were as follows.

$[\alpha]_D^{25}$=−63.6 (c 0.38, CHCl$_3$); IR (KBr) 3449, 1760, 1719 cm$^{-1}$; $^1$H NMR (400 MHz, CDCl$_3$) δ 3.26 (1H, dd, J=14.1, 9.6 Hz), 3.42 (1H, dd, J=14.1, 3.6 Hz), 4.86 (1H, s), 5.41 (1H, dd, J=9.6, 3.7 Hz), 6.92 (1H, t, J=6.9 Hz), 7.16 (1H, d, J=7.3 Hz), 7.18-7.24 (2H, m), 7.32 (1H, t, J=7.8 Hz), 7.38 (1H, t, J=7.7 Hz), 7.46-7.52 (3H, m), 7.59 (1H, s), 7.68-7.76 (4H, m), 7.80-7.86 (1H, m); $^{13}$C NMR (100 MHz, CDCl$_3$) δ 37.1, 53.0, 73.2, 119.9, 125.5, 125.6, 125.8, 126.1, 127.1, 127.3, 127.6, 127.7, 128.1, 128.2, 128.3, 132.5, 133.0, 133.3, 139.9, 140.0, 141.3, 141.4, 170.6, 174.8; HRESIMS calcd for $C_{27}H_{20}O_4Na$ [M+Na]$^+$ 431.1259, found 431.1264.

The optical purity of H-31 was determined using a chiral column (AD-H, hexane:IPA, 5:1). As a result, the product was optically almost pure (>98% ee).

The chemical structure of H-31 found was as follows.
(H-31)

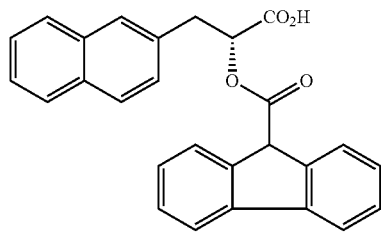 [SMILES: O=C(O[C@H](Cc1ccc2ccccc2c1)C(=O)O)C1c2ccccc2-c2ccccc21]

(Example 2-8) Synthesis of H-141

Using L-naphthylalanine as a starting substance, synthesis was carried out by four steps from the L-naphthylalanine similarly to the synthesis of H-31. The resulting spectrum data were the same as those of H-31. (94% ee, AD-H column, hexane:isopropanol, 5:1). The specific rotation was $[\alpha]_D^{25}$=+53.7 (c 0.56, CHCl$_3$). The chemical structure of H-141 found was as follows. In H-31, which was synthesized in Example 4, the configuration at the asymmetric carbon was the R configuration. In contrast, in H-141, which was synthesized in the present Example, the configuration at the asymmetric carbon was the S configuration.

(H-141)

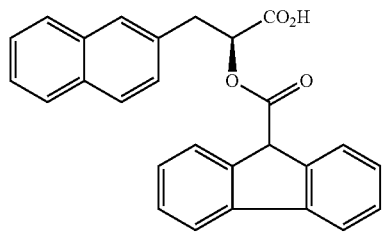 [SMILES: O=C(O[C@@H](Cc1ccc2ccccc2c1)C(=O)O)C1c2ccccc2-c2ccccc21]

(Example 2-9) Synthesis of H-28

To a solution of H-26 (200 mg, 0.654 mmol), 2-methyl-5-(4-methoxyphenyl)furan-3-carboxylic acid (182 mg, 0.785 mmol), and 4-dimethylaminopyridine (8.0 mg, 0.065 mmol) in dichloromethane (5 mL), 1-ethyl-3-(3-dimethylaminopropyl)carbodiimide hydrochloride (163 mg, 0.85 mmol) was added at room temperature, and the resulting mixture was stirred at the same temperature for 24 hours. Water was added to the mixture, and extraction was carried out with ethyl acetate. The organic layer was washed with saturated brine, and then dried over anhydrous magnesium sulfate, followed by filtration, and concentration under reduced pressure. The resulting residue was purified by silica gel column chromatography (hexane:ethyl acetate, 6:1), to obtain H-28 as a colorless oily substance (282 mg, 0.543 mmol, 83%).

Regarding H-28, the NMR measurement spectrum and the result of mass spectrometry by HR-ESI-MS were as follows.

$^1$H NMR (400 MHz, CDCl$_3$) δ 2.55 (3H, s), 3.42 (1H, dd, J=14.2, 7.7 Hz), 3.47 (1H, dd, J=14.2, 5.5 Hz), 3.84 (3H, s), 5.17 (1H, d, J=12.3 Hz), 5.23 (1H, d, J=12.3 Hz), 5.57-5.63 (1H, m), 6.74 (1H, s), 6.93 (2H, d, J=8.6 Hz), 7.21-7.35 (5H, m), 7.39 (1H, d, J=8.7 Hz), 7.43-7.51 (2H, m), 7.55 (2H, d, J=8.6 Hz), 7.71 (1H, s), 7.74-7.85 (3H, m); $^{13}$C NMR (100 MHz, CDCl$_3$) δ 13.9, 37.6, 55.3, 67.1, 72.7, 103.7, 114.1, 114.2, 122.9, 125.1, 125.3, 125.7, 126.1, 127.4, 127.53, 127.61, 128.11, 128.15, 128.19, 128.3, 128.5, 132.4, 133.2, 133.4, 135.1, 151.9, 158.8, 159.3, 163.2, 169.6; HRESIMS calcd for $C_{33}H_{28}O_6Na$ [M+Na]$^+$ 543.1784, found 543.1781.

The chemical structure of H-28 found was as follows.
(H-28)

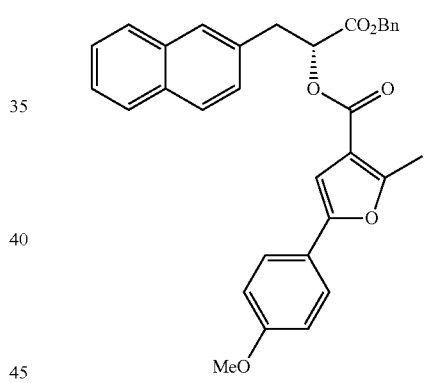

(Example 2-10) Synthesis of H-32

To a solution of H-28 (230 mg, 0.442 mmol) in THF (6 mL), 5% Pd/C (100 mg) was added, and the resulting mixture was stirred under hydrogen atmosphere at room temperature for 16 hours. The reaction mixture was filtered using Celite, and the residue was washed with ethyl acetate, followed by concentration of the solution under reduced pressure, to obtain H-32 as yellow crystals (175 mg, 0.407 mmol, 92%).

Regarding H-32, the NMR measurement spectrum and the result of mass spectrometry by HR-ESI-MS were as follows.

$^1$H NMR (400 MHz, CDCl$_3$) δ 2.54 (3H, s), 3.42 (1H, dd, J=14.2, 8.7 Hz), 3.51 (1H, dd, J=14.2, 4.1 Hz), 3.83 (3H, s), 5.53-5.59 (1H, m), 6.71 (1H, s), 6.91 (2H, d, J=8.6 Hz), 7.37-7.50 (3H, m), 7.53 (2H, d, J=8.6 Hz), 7.75-7.85 (4H, m); $^{13}$C NMR (100 MHz, CDCl$_3$) δ 13.9, 37.4, 55.3, 72.3, 103.6, 114.1, 122.9, 125.2, 125.8, 126.2, 127.3, 127.56, 127.65, 128.17, 128.22, 132.5, 133.3, 133.4, 152.0, 159.1, 159.3, 163.3, 175.0; HRESIMS calcd for C$_{26}$H$_{22}$O$_6$Na [M+Na]$^+$ 453.1314, found 453.1315.
(H-32)

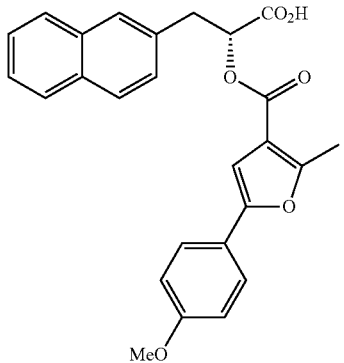 [SMILES: COc1ccc(-c2cc(C(=O)O[C@H](Cc3ccc4ccccc4c3)C(=O)O)c(C)o2)cc1]

(Example 2-11) Synthesis of H-29

To a solution of H-26 (200 mg, 0.654 mmol), 4-phenylbenzoic acid (155 mg, 0.785 mmol), and 4-dimethylaminopyridine (8.0 mg, 0.065 mmol) in dichloromethane (5 mL), 1-ethyl-3-(3-dimethylaminopropyl)carbodiimide hydrochloride (163 mg, 0.85 mmol) was added at room temperature, and the resulting mixture was stirred at the same temperature for 24 hours. Water was added to the mixture, and extraction was carried out with ethyl acetate. The organic layer was washed with saturated brine, and then dried over anhydrous magnesium sulfate, followed by filtration, and concentration under reduced pressure. The resulting residue was purified by silica gel column chromatography (hexane:ethyl acetate, 6:1), to obtain H-29 as white crystals (273 mg, 0.562 mmol, 86%).

Regarding H-29, the NMR measurement spectrum and the result of mass spectrometry by HR-ESI-MS were as follows.

$^1$H NMR (400 MHz, CDCl$_3$) δ 3.44-3.54 (2H, m), 5.18 (1H, d, J=12.3 Hz), 5.22 (1H, d, J=12.3 Hz), 5.65 (1H, dd, J=7.3, 5.5 Hz), 7.21-7.33 (4H, m), 7.38-7.54 (7H, m), 7.60-7.69 (4H, m), 7.72-7.84 (4H, m), 8.12 (2H, d, J=8.7 Hz); $^{13}$C NMR (100 MHz, CDCl$_3$) δ 37.6, 67.1, 73.4, 125.7, 126.1, 127.1, 127.26, 127.33, 127.5, 127.6, 128.16, 128.20, 128.32, 128.49, 128.9, 129.0, 130.3, 131.1, 132.5, 133.3, 133.4, 135.1, 139.5, 139.9, 146.1, 147.3, 165.8, 169.5; HRESIMS calcd for C$_{33}$H$_{26}$O$_4$Na [M+Na]$^+$ 509.1729, found 509.1721.

The chemical structure of H-29 found was as follows.
(H-29)

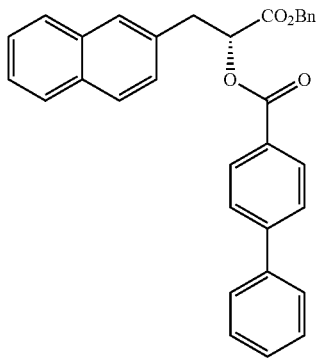 [SMILES: O=C(O[C@H](Cc1ccc2ccccc2c1)C(=O)OCc1ccccc1)c1ccc(-c2ccccc2)cc1]

(Example 2-12) Synthesis of H-33

To a solution of H-29 (250 mg, 0.514 mmol) in THF (6 mL), 5% Pd/C (100 mg) was added, and the resulting mixture was stirred under hydrogen atmosphere at room temperature for 16 hours. The reaction mixture was filtered using Celite, and the residue was washed with ethyl acetate, followed by concentration of the solution under reduced pressure, to obtain H-33 as yellow crystals (185 mg, 0.467 mmol, 91%).

Regarding H-33, the NMR measurement spectrum and the result of mass spectrometry by HR-ESI-MS were as follows.

$^1$H NMR (400 MHz, CDCl$_3$) δ 3.48 (1H, dd, J=14.2, 8.2 Hz), 3.55 (1H, dd, J=14.2, 4.5 Hz), 5.62 (1H, dd, J=8.2, 4.5 Hz), 7.37-7.50 (6H, m), 7.57-7.66 (4H, m), 7.78-7.84 (4H, m), 8.08 (2H, d, J=8.7 Hz); $^{13}$C NMR (100 MHz, CDCl$_3$) δ 37.4, 73.0, 125.8, 126.2, 127.1, 127.3, 127.4, 127.6, 127.8, 128.16, 128.20, 128.25, 128.9, 130.3, 132.5, 133.3, 133.4, 139.9, 146.2, 165.8, 174.8; HRESIMS calcd for C$_{26}$H$_{20}$O$_4$Na [M+Na]$^+$ 419.1259, found 419.1263.

The chemical structure of H-33 found was as follows.
(H-33)

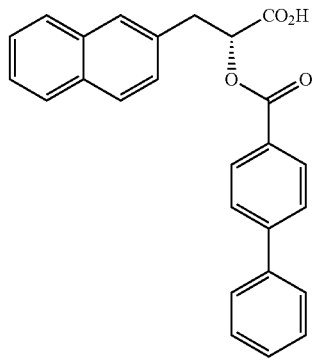 [SMILES: O=C(O[C@H](Cc1ccc2ccccc2c1)C(=O)O)c1ccc(-c2ccccc2)cc1]

(Example 2-13) Synthesis of H-92

To a solution of H-26 (200 mg, 0.654 mmol), fluorene-9-acetic acid (176 mg, 0.785 mmol), and 4-dimethylaminopyridine (8.0 mg, 0.065 mmol) in dichloromethane (5 mL), 1-ethyl-3-(3-dimethylaminopropyl)carbodiimide hydrochloride (163 mg, 0.85 mmol) was added at room temperature, and the resulting mixture was stirred at the same temperature for 48 hours. Water was added to the mixture, and extraction was carried out with ethyl acetate. The organic layer was washed with saturated brine, and then dried over anhydrous magnesium sulfate, followed by filtration, and concentration under reduced pressure. The resulting residue was purified by silica gel column chromatography (hexane:ethyl acetate, 3:1), to obtain H-92 as a colorless oily substance (240 mg, 0.469 mmol, 72%).

Regarding H-92, the NMR measurement spectrum and the result of mass spectrometry by HR-ESI-MS were as follows.

$^1$H NMR (400 MHz, CDCl$_3$) δ 2.80 (1H, dd, J=16.5, 6.8 Hz), 2.88 (1H, dd, J=16.5, 6.8 Hz), 3.31 (1H, dd, J=14.2, 8.7 Hz), 3.41 (1H, dd, J=14.2, 4.5 Hz), 4.39 (1H, t, J=6.8 Hz), 5.23 (2H, s), 5.55 (1H, dd, J=8.7, 4.5 Hz), 7.11 (1H, t, J=7.3 Hz), 7.16 (1H, t, J=7.3 Hz), 7.25-7.41 (10H, m), 7.44-7.50 (2H, m), 7.65 (1H, s), 7.70-7.78 (4H, m), 7.79-7.85 (1H, m); $^{13}$C NMR (100 MHz, CDCl$_3$) δ 37.5, 38.2, 43.2, 67.2, 73.4, 119.7, 120.0, 124.3, 125.7, 126.1, 127.10, 127.14, 127.4, 127.6, 128.0, 128.2, 128.3, 128.4, 128.5, 132.5, 133.1, 133.4, 135.0, 140.59, 140.63, 145.9, 146.0, 169.4, 171.9; HRESIMS calcd for $C_{35}H_{28}O_4Na$ $[M+Na]^+$ 535.1885, found 535.1885.

The chemical structure of H-92 found was as follows.
(H-92)

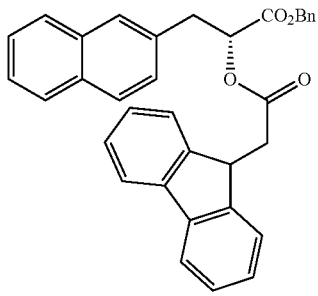 [SMILES: O=C(CC1c2ccccc2-c2ccccc21)O[C@H](Cc1ccc2ccccc2c1)C(=O)OCc1ccccc1]

(Example 2-14) Synthesis of H-106

To a solution of H-92 (220 mg, 0.430 mmol) in THF (6 mL), 5% Pd/C (100 mg) was added, and the resulting mixture was stirred under hydrogen atmosphere at room temperature for 16 hours. The reaction mixture was filtered using Celite, and the residue was washed with ethyl acetate, followed by concentration of the solution under reduced pressure, to obtain H-106 as a brown oily substance (173 mg, 0.41 mmol, 95%).

Regarding H-106, the NMR measurement spectrum and the result of mass spectrometry by HR-ESI-MS were as follows.

$^1$H NMR (400 MHz, CDCl$_3$) δ 2.79 (1H, dd, J=16.5, 6.9 Hz), 2.86 (1H, dd, J=16.5, 6.8 Hz), 3.29 (1H, dd, J=14.6, 9.1 Hz), 3.45 (1H, dd, J=14.6, 3.7 Hz), 4.36 (1H, t, J=6.8 Hz), 5.52 (1H, dd, J=9.1, 3.7 Hz), 7.08 (1H, t, J=7.3 Hz), 7.13 (1H, t, J=7.3 Hz), 7.28-7.38 (5H, m), 7.43-7.49 (2H, m), 7.67-7.84 (6H, m); $^{13}$C NMR (100 MHz, CDCl$_3$) δ 37.3, 38.1, 43.1, 73.0, 119.8, 124.25, 124.35, 125.8, 126.2, 127.11, 127.14, 127.3, 127.4, 127.6, 128.0, 128.3, 132.5, 133.2, 133.4, 140.6, 140.7, 145.8, 145.9, 172.0, 174.5; HRESIMS calcd for $C_{28}H_{22}O_4Na$ $[M+Na]^+$ 445.1416, found 445.1413.

The chemical structure of H-106 found was as follows.
(H-106)

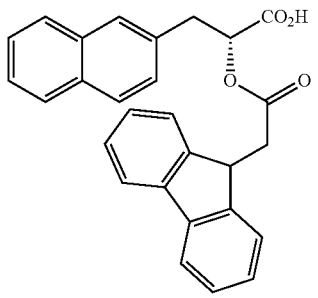 [SMILES: O=C(CC1c2ccccc2-c2ccccc21)O[C@H](Cc1ccc2ccccc2c1)C(=O)O]

(Example 2-15) Synthesis of H-112

To a solution of H-26 (200 mg, 0.654 mmol), p-phenoxybenzoic acid (168 mg, 0.785 mmol), and 4-dimethylaminopyridine (8.0 mg, 0.065 mmol) in dichloromethane (5 mL), 1-ethyl-3-(3-dimethylaminopropyl)carbodiimide hydrochloride (163 mg, 0.85 mmol) was added at room temperature, and the resulting mixture was stirred at the same temperature for 24 hours. Water was added to the mixture, and extraction was carried out with ethyl acetate. The organic layer was washed with saturated brine, and then dried over anhydrous magnesium sulfate, followed by filtration, and concentration under reduced pressure. The resulting residue was purified by silica gel column chromatography (hexane:ethyl acetate, 6:1), to obtain H-112 as a colorless oily substance (328 mg, 0.654 mmol, 100%).

Regarding H-112, the NMR measurement spectrum and the result of mass spectrometry by HR-ESI-MS were as follows.

$^1$H NMR (400 MHz, CDCl$_3$) δ 3.40-3.52 (2H, m), 5.17 (1H, d, J=12.4 Hz), 5.21 (1H, d, J=12.4 Hz), 5.58-5.64 (1H, m), 6.98 (2H, dd, J=8.7, 1.8 Hz), 7.03-7.09 (2H, m), 7.11 (1H, d, J=8.7, Hz), 7.18-7.32 (5H, m), 7.37-7.50 (5H, m), 7.71 (1H, s), 7.73-7.84 (3H, m), 8.01 (2H, dd, J=9.1, 2.3 Hz); HRESIMS calcd for $C_{33}H_{26}O_5Na$ $[M+Na]^+$ 525.1678, found 525.1685.

The chemical structure of H-112 found was as follows.
(H-112)

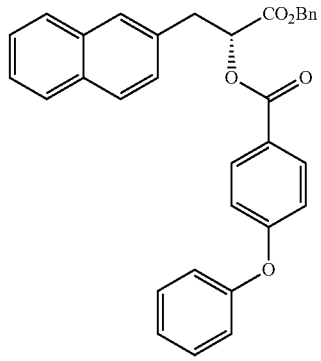 [SMILES: O=C(O[C@H](Cc1ccc2ccccc2c1)C(=O)OCc1ccccc1)c1ccc(Oc2ccccc2)cc1]

(Example 2-16) Synthesis of H-123

To a solution of H-112 (328 mg, 0.654 mmol) in THF (8 mL), 5% Pd/C (100 mg) was added, and the resulting mixture was stirred under hydrogen atmosphere at room temperature for 20 hours. The reaction mixture was filtered using Celite, and the residue was washed with ethyl acetate, followed by concentration of the solution under reduced pressure, to obtain H-123 as a colorless oily substance (257 mg, 0.624 mmol, 95%).

Regarding H-123, the NMR measurement spectrum and the result of mass analysis by HR-ESI-MS were as follows.

$^1$H NMR (400 MHz, CDCl$_3$) δ 3.39-3.54 (2H, m), 5.55 (1H, dd, J=8.7, 4.6 Hz), 6.95 (2H, d, J=9.2 Hz), 7.04 (2H, d, J=8.7 Hz), 7.19 (1H, t, J=7.8 Hz), 7.35-7.48 (5H, m), 7.74-7.84 (4H, m), 7.97 (2H, d, J=8.7 Hz); $^{13}$C NMR (100 MHz, CDCl$_3$) δ 37.4, 73.0, 117.3, 120.1, 123.3, 124.5, 125.7, 126.1, 127.4, 127.6, 128.1, 128.2, 130.0, 132.0, 132.5, 133.36, 133.41, 155.4, 162.2, 165.4, 174.8; HRESIMS calcd for $C_{26}H_{20}O_5Na$ $[M+Na]^+$ 435.1208, found 435.1214.

The chemical structure of H-123 found was as follows.
(H-123)

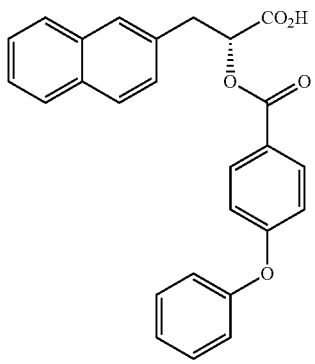 [SMILES: O=C(O[C@H](Cc1ccc2ccccc2c1)C(=O)O)c1ccc(Oc2ccccc2)cc1]

(Example 2-17) Synthesis of H-117

To a solution of H-26 (200 mg, 0.654 mmol), m-phenoxybenzoic acid (168 mg, 0.785 mmol), and 4-dimethylaminopyridine (8.0 mg, 0.065 mmol) in dichloromethane (5 mL), 1-ethyl-3-(3-dimethylaminopropyl)carbodiimide hydrochloride (163 mg, 0.85 mmol) was added at room temperature, and the resulting mixture was stirred at the same temperature for 24 hours. Water was added to the mixture, and extraction was carried out with ethyl acetate. The organic layer was washed with saturated brine, and then dried over anhydrous magnesium sulfate, followed by filtration, and concentration under reduced pressure. The resulting residue was purified by silica gel column chromatography (hexane:ethyl acetate, 6:1), to obtain H-117 as a colorless oily substance (273 mg, 0.544 mmol, 84%).

Regarding H-117, the NMR measurement spectrum and the result of mass spectrometry by HR-ESI-MS were as follows.

$^1$H NMR (400 MHz, CDCl$_3$) δ 3.40 (1H, dd, J=14.2, 7.8 Hz), 3.45 (1H, dd, J=14.2, 5.1 Hz), 5.14 (1H, d, J=12.3 Hz), 5.19 (1H, d, J=12.3 Hz), 5.55 (1H, dd, J=7.8, 5.1 Hz), 7.02 (2H, dd, J=8.7, 0.9 Hz), 7.13-7.47 (13H, m), 7.65-7.82 (6H, m); $^{13}$C NMR (100 MHz, CDCl$_3$) δ 37.6, 67.2, 73.6, 119.1, 119.7, 123.77, 123.78, 124.6, 125.7, 126.0, 127.5, 127.6, 128.11, 128.16, 128.2, 128.4, 128.5, 129.8, 129.9, 131.0, 132.5, 133.2, 133.4, 135.1, 156.6, 157.4, 165.3, 169.3; HRESIMS calcd for C$_{33}$H$_{26}$O$_5$Na [M+Na]$^+$ 525.1678, found 525.1682.

The chemical structure of H-117 found was as follows.
(H-117)

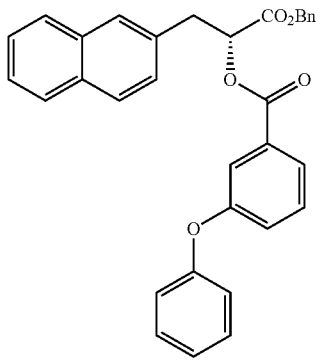 [SMILES: O=C(O[C@H](Cc1ccc2ccccc2c1)C(=O)OCc1ccccc1)c1cccc(Oc2ccccc2)c1]

(Example 2-18) Synthesis of H-130

To a solution of H-117 (240 mg, 0.478 mmol) in THF (6 mL), 5% Pd/C (100 mg) was added, and the resulting mixture was stirred under hydrogen atmosphere at room temperature for 20 hours. The reaction mixture was filtered using Celite, and the residue was washed with ethyl acetate, followed by concentration of the solution under reduced pressure, to obtain H-130 as a colorless oily substance (187 mg, 0.454 mmol, 95%).

Regarding H-130, the NMR measurement spectrum and the result of mass spectrometry by HR-ESI-MS were as follows.

$^1$H NMR (400 MHz, CDCl$_3$) δ 3.39 (1H, dd, J=14.2, 8.7 Hz), 3.48 (1H, dd, J=14.2, 4.1 Hz), 5.52 (1H, dd, J=8.7, 4.1 Hz), 7.01 (2H, d, J=7.7 Hz), 7.16 (1H, t, J=7.3 Hz), 7.19 (1H, dd, J=8.3, 2.7 Hz), 7.33-7.40 (4H, m), 7.42-7.47 (2H, m), 7.65 (1H, bs), 7.72-7.82 (5H, m); $^{13}$C NMR (100 MHz, CDCl$_3$) δ 37.4, 73.3, 119.1, 119.7, 123.7, 123.8, 124.5, 125.8, 126.1, 127.4, 127.62, 127.64, 128.1, 128.2, 129.8, 129.9, 130.7, 132.5, 133.2, 133.4, 156.5, 157.5, 165.3, 174.8; HRESIMS calcd for C$_{26}$H$_{20}$O$_5$Na [M+Na]$^+$ 435.1208, found 435.1205.

The chemical structure of H-130 found was as follows.
(H-130)

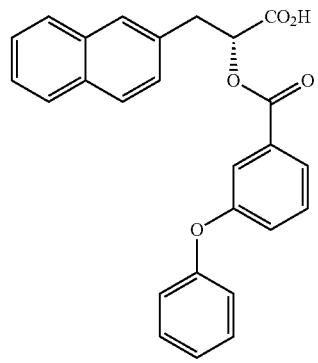 [SMILES: O=C(O[C@H](Cc1ccc2ccccc2c1)C(=O)O)c1cccc(Oc2ccccc2)c1]

(Example 2-19) Synthesis of H-118

To a solution of H-26 (200 mg, 0.654 mmol), o-phenoxybenzoic acid (168 mg, 0.785 mmol), and 4-dimethylaminopyridine (8.0 mg, 0.065 mmol) in dichloromethane (5 mL), 1-ethyl-3-(3-dimethylaminopropyl)carbodiimide hydrochloride (163 mg, 0.85 mmol) was added at room temperature, and the resulting mixture was stirred at the same temperature for 48 hours. Water was added to the mixture, and extraction was carried out with ethyl acetate. The organic layer was washed with saturated brine, and then dried over anhydrous magnesium sulfate, followed by filtration, and concentration under reduced pressure. The resulting residue was purified by silica gel column chromatography (hexane:ethyl acetate, 6:1), to obtain H-118 as a colorless oily substance (273 mg, 0.544 mmol, 84%).

Regarding H-118, the NMR measurement spectrum and the result of mass spectrometry by HR-ESI-MS were as follows.

$^1$H NMR (400 MHz, CDCl$_3$) δ 3.30 (1H, dd, J=14.2, 7.8 Hz), 3.37 (1H, dd, J=14.2, 5.0 Hz), 5.10 (1H, d, J=12.4 Hz), 5.14 (1H, d, J=12.4 Hz), 5.56 (1H, dd, J=7.8, 5.0 Hz), 6.90-6.96 (3H, m), 7.07-7.20 (3H, m), 7.22-7.35 (6H, m), 7.41-7.46 (3H, m), 7.61 (1H, bs), 7.63-7.68 (2H, m), 7.75-

7.79 (1H, m), 7.90 (1H, dd, J=7.8, 1.8 Hz); $^{13}$C NMR (100 MHz, CDCl$_3$) δ 37.5, 67.1, 73.6, 118.8, 120.1, 121.8, 123.1, 123.4, 125.6, 125.9, 127.51, 127.52, 127.6, 128.0, 128.1, 128.2, 128.3, 128.4, 129.7, 132.2, 132.4, 133.31, 133.35, 133.9, 135.1, 156.9, 157.1, 164.9, 169.4; HRESIMS calcd for C$_{33}$H$_{26}$O$_5$Na [M+Na]$^+$ 525.1678, found 525.1683.

The chemical structure of H-118 found was as follows.
(H-118)

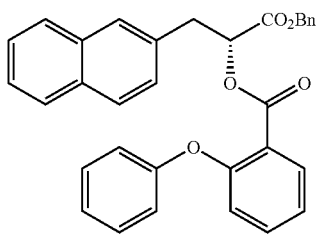 [SMILES: O=C(O[C@H](Cc1ccc2ccccc2c1)C(=O)OCc1ccccc1)c1ccccc1Oc1ccccc1]

(Example 2-20) Synthesis of H-132

To a solution of H-118 (242 mg, 0.482 mmol) in THF (6 mL), 5% Pd/C (100 mg) was added, and the resulting mixture was stirred under hydrogen atmosphere at room temperature for 20 hours. The reaction mixture was filtered using Celite, and the residue was washed with ethyl acetate, followed by concentration of the solution under reduced pressure, to obtain H-132 as a colorless oily substance (196 mg, 0.476 mmol, 99%).

Regarding H-132, the NMR measurement spectrum and the result of mass spectrometry by HR-ESI-MS were as follows.

$^1$H NMR (400 MHz, CDCl$_3$) δ 3.31 (1H, dd, J=14.2, 8.7 Hz), 3.37 (1H, dd, J=14.2, 4.1 Hz), 5.56 (1H, dd, J=8.7, 4.1 Hz), 6.88-6.94 (3H, m), 7.09 (1H, t, J=7.3 Hz), 7.12 (1H, t, J=7.3 Hz), 7.25-7.31 (2H, m), 7.36 (1H, dd, J=8.7, 1.8 Hz), 7.40-7.46 (3H, m), 7.64-7.72 (3H, m), 7.75-7.80 (1H, m), 7.90 (1H, dd, J=7.8, 1.9 Hz); $^{13}$C NMR (100 MHz, CDCl$_3$) δ 37.3, 73.2, 118.9, 120.0, 121.4, 123.1, 123.6, 125.6, 126.0, 127.5, 127.6, 127.7, 128.1, 129.8, 132.3, 132.4, 133.3, 133.4, 133.9, 134.1, 156.8, 157.0, 164.8, 174.1; HRESIMS calcd for C$_{26}$H$_{20}$O$_5$Na [M+Na]+435.1208, found 435.1202.

The chemical structure of H-132 found was as follows.
(H-132)

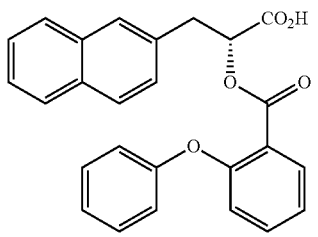 [SMILES: O=C(O[C@H](Cc1ccc2ccccc2c1)C(=O)O)c1ccccc1Oc1ccccc1]

(Example 2-21) Synthesis of H-119

To a solution of H-26 (200 mg, 0.654 mmol), diphenylacetic acid (167 mg, 0.785 mmol), and 4-dimethylaminopyridine (8.0 mg, 0.065 mmol) in dichloromethane (5 mL), 1-ethyl-3-(3-dimethylaminopropyl)carbodiimide hydrochloride (163 mg, 0.85 mmol) was added at room temperature, and the resulting mixture was stirred at the same temperature for 24 hours. Water was added to the mixture, and extraction was carried out with ethyl acetate. The organic layer was washed with saturated brine, and then dried over anhydrous magnesium sulfate, followed by filtration, and concentration under reduced pressure. The resulting residue was purified by silica gel column chromatography (hexane:ethyl acetate, 6:1), to obtain H-119 as white crystals (303 mg, 0.606 mmol, 94%). Regarding H-119, the NMR measurement spectrum and the result of mass spectrometry by HR-ESI-MS were as follows.

$^1$H NMR (400 MHz, CDCl$_3$) δ 3.23 (1H, dd, J=14.2, 8.7 Hz), 3.37 (1H, dd, J=14.2, 4.1 Hz), 5.05 (1H, s), 5.11 (1H, d, J=12.4 Hz), 5.15 (1H, d, J=12.4 Hz), 5.47 (1H, dd, J=8.7, 4.1 Hz), 7.08-7.22 (13H, m), 7.25-7.33 (3H, m), 7.44-7.50 (3H, m), 7.62-7.67 (2H, m), 7.77-7.82 (1H, m); $^{13}$C NMR (100 MHz, CDCl$_3$) δ 37.3, 56.8, 67.2, 73.5, 125.7, 126.0, 127.1, 127.2, 127.3, 127.6, 127.7, 128.06, 128.1, 128.3, 128.37, 128.41, 128.52, 128.56, 128.7, 132.4, 133.1, 133.3, 135.0, 137.96, 138.00, 169.2, 171.8; HRESIMS calcd for C$_{34}$H$_{28}$O$_4$Na [M+Na]$^+$ 523.1885, found 523.1880. The chemical structure of H-119 found was as follows.

(H-119)

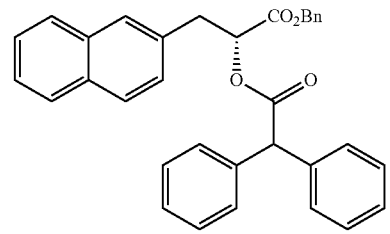

(Example 2-22) Synthesis of H-134

To a solution of H-119 (264 mg, 0.528 mmol) in THF (6 mL), 5% Pd/C (100 mg) was added, and the resulting mixture was stirred under hydrogen atmosphere at room temperature for 20 hours. The reaction mixture was filtered using Celite, and the residue was washed with ethyl acetate, followed by concentration of the solution under reduced pressure, to obtain H-134 as white crystals (210 mg, 0.512 mmol, 97%).

Regarding H-134, the NMR measurement spectrum and the result of mass spectrometry by HR-ESI-MS were as follows.

$^1$H NMR (400 MHz, CDCl$_3$) δ 3.26 (1H, dd, J=14.5, 8.5 Hz), 3.42 (1H, bd, J=14.2 Hz), 5.11 (1H, s), 5.47 (1H, bs), 7.10-7.26 (11H, m), 7.45-7.58 (3H, m), 7.67-7.74 (2H, m), 7.82-7.87 (1H, m); $^{13}$C NMR (100 MHz, CDCl$_3$) δ 37.2, 56.7, 73.1, 125.7, 126.0, 127.15, 127.19, 127.6, 127.7, 128.06, 128.1, 128.41, 128.49, 128.66, 128.73, 132.4, 133.0, 133.3, 137.9, 171.9, 175.1; HRESIMS calcd for C$_{27}$H$_{22}$O$_4$Na [M+Na]$^-$ 433.1416, found 433.1412.

The chemical structure of H-134 found was as follows.
(H-134)

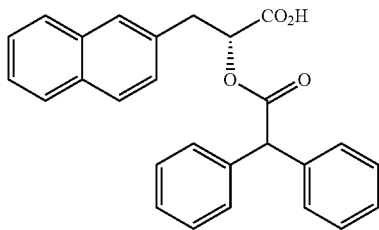 [SMILES: O=C(O[C@H](Cc1ccc2ccccc2c1)C(=O)O)C(c1ccccc1)c1ccccc1]

(Example 2-23) Synthesis of H-137

To a solution of H-26 (200 mg, 0.654 mmol), 2-naphthaleneacetic acid (146 mg, 0.785 mmol), and 4-dimethylaminopyridine (8.0 mg, 0.065 mmol) in dichloromethane (5 mL), 1-ethyl-3-(3-dimethylaminopropyl)carbodiimide hydrochloride (163 mg, 0.85 mmol) was added at room temperature, and the resulting mixture was stirred at the same temperature for 24 hours. Water was added to the mixture, and extraction was carried out with ethyl acetate. The organic layer was washed with saturated brine, and then dried over anhydrous magnesium sulfate, followed by filtration, and concentration under reduced pressure. The resulting residue was purified by silica gel column chromatography (hexane:ethyl acetate, 6:1), to obtain H-137 as white crystals (265 mg, 0.559 mmol, 86%).

Regarding H-137, the NMR measurement spectrum and the result of mass spectrometry by HR-ESI-MS were as follows.

$^1$H NMR (400 MHz, CDCl$_3$) δ 3.27 (1H, dd, J=14.2, 8.2 Hz), 3.36 (1H, dd, J=14.2, 4.6 Hz), 3.84 (2H, s), 5.13 (1H, d, J=12.4 Hz), 5.17 (1H, d, J=12.4 Hz), 5.43 (1H, dd, J=8.2, 4.6 Hz), 7.15-7.34 (7H, m), 7.42-7.52 (4H, m), 7.53-7.72 (6H, m), 7.75-7.84 (2H, m); $^{13}$C NMR (100 MHz, CDCl$_3$) δ 37.3, 41.1, 67.1, 73.3, 125.6, 125.8, 125.97, 126.03, 127.27, 127.32, 127.54, 127.59, 127.7, 127.97, 128.01, 128.03, 128.09, 128.2, 128.3, 128.5, 130.8, 132.36, 132.41, 133.1, 133.27, 133.34, 135.0, 169.3, 170.8; HRESIMS calcd for C$_{32}$H$_{26}$O$_4$Na [M+Na]$^+$ 497.1729, found 497.1732. The chemical structure of H-137 found was as follows.
(H-137)

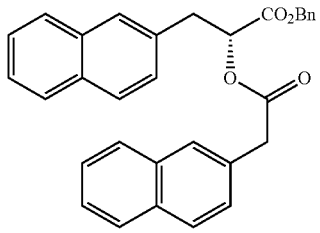 [SMILES: O=C(Cc1ccc2ccccc2c1)O[C@H](Cc1ccc2ccccc2c1)C(=O)OCc1ccccc1]

(Example 2-24) Synthesis of H-149

To a solution of H-137 (245 mg, 0.517 mmol) in THF (6 mL), 5% Pd/C (100 mg) was added, and the resulting mixture was stirred under hydrogen atmosphere at room temperature for 18 hours. The reaction mixture was filtered using Celite, and the residue was washed with ethyl acetate, followed by concentration of the solution under reduced pressure, to obtain H-149 as white crystals (190 mg, 0.495 mmol, 96%).

Regarding H-149, the NMR measurement spectrum and the result of mass spectrometry by HR-ESI-MS were as follows.

$^1$H NMR (400 MHz, CDCl$_3$) δ 3.25 (1H, dd, J=14.2, 9.2 Hz), 3.38 (1H, dd, J=14.2, 4.1 Hz), 3.81 (2H, s), 5.38 (1H, dd, J=9.2, 4.1 Hz), 7.16-7.24 (2H, m), 7.39-7.49 (4H, m), 7.54-7.68 (6H, m), 7.74-7.80 (2H, m); $^{13}$C NMR (100 MHz, CDCl$_3$) δ 37.2, 41.0, 72.9, 125.7, 125.8, 126.1, 127.2, 127.6, 127.7, 128.03, 128.08, 128.1, 130.6, 132.40, 132.43, 133.0, 133.29, 133.35, 170.9, 174.9; HRESIMS calcd for C$_{25}$H$_{20}$O$_4$Na [M+Na]$^+$ 407.1259, found 407.1256.

The chemical structure of H-149 found was as follows.
(H-149)

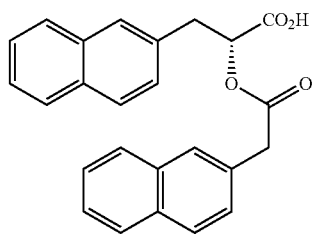 [SMILES: O=C(Cc1ccc2ccccc2c1)O[C@H](Cc1ccc2ccccc2c1)C(=O)O]

(Example 2-25) Synthesis of H-139

To a solution of H-26 (200 mg, 0.654 mmol), 1-naphthaleneacetic acid (146 mg, 0.785 mmol), and 4-dimethylaminopyridine (8.0 mg, 0.065 mmol) in dichloromethane (5 mL), 1-ethyl-3-(3-dimethylaminopropyl)carbodiimide hydrochloride (163 mg, 0.85 mmol) was added at room temperature, and the resulting mixture was stirred at the same temperature for 24 hours. Water was added to the mixture, and extraction was carried out with ethyl acetate. The organic layer was washed with saturated brine, and then dried over anhydrous magnesium sulfate, followed by filtration, and concentration under reduced pressure. The resulting residue was purified by silica gel column chromatography (hexane:ethyl acetate, 6:1), to obtain H-139 as a colorless oily substance (266 mg, 0.559 mmol, 86%).

Regarding H-139, the NMR measurement spectrum and the result of mass spectrometry by HR-ESI-MS were as follows.

$^1$H NMR (400 MHz, CDCl$_3$) δ 3.21 (1H, dd, J=14.2, 8.7 Hz), 3.31 (1H, dd, J=14.2, 4.1 Hz), 4.10 (2H, s), 5.12 (2H, s), 5.40 (1H, dd, J=8.7, 4.1 Hz), 7.10 (1H, dd, J=8.3, 1.8 Hz), 7.16-7.21 (2H, m), 7.23-7.35 (6H, m), 7.42 (1H, ddd, J=8.2, 6.9, 0.9 Hz), 7.45-7.51 (3H, m), 7.61 (1H, d, J=8.2 Hz), 7.65-7.70 (1H, m), 7.74-7.84 (4H, m); $^{13}$C NMR (100 MHz, CDCl$_3$) δ 37.3, 38.6, 67.1, 73.2, 123.6, 125.3, 125.7, 126.0, 126.2, 127.3, 127.6, 127.7, 127.96, 128.02, 128.09, 128.2, 128.3, 128.5, 128.6, 129.8, 131.9, 132.4, 133.1, 133.3, 133.7, 135.0, 169.3, 170.8; HRESIMS calcd for C$_{32}$H$_{26}$O$_4$Na [M+Na]$^+$ 497.1729, found 497.1728.

The chemical structure of H-139 found was as follows.
(H-139)

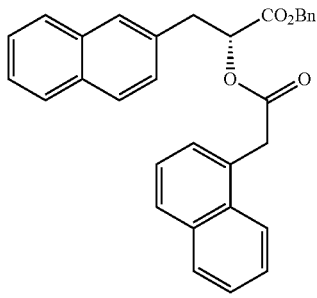 [SMILES: O=C(Cc1cccc2ccccc12)O[C@H](Cc1ccc2ccccc2c1)C(=O)OCc1ccccc1]

(Example 2-26) Synthesis of H-151

To a solution of H-139 (240 mg, 0.506 mmol) in THF (6 mL), 5% Pd/C (100 mg) was added, and the resulting mixture was stirred under hydrogen atmosphere at room temperature for 18 hours. The reaction mixture was filtered using Celite, and the residue was washed with ethyl acetate, followed by concentration of the solution under reduced pressure, to obtain H-151 as white crystals (192 mg, 0.50 mmol, 99%).

Regarding H-151, the NMR measurement spectrum and the result of mass spectrometry by HR-ESI-MS were as follows.

$^1$H NMR (400 MHz, CDCl$_3$) δ 3.21 (1H, dd, J=14.2, 9.6 Hz), 3.34 (1H, dd, J=14.2, 3.6 Hz), 4.09 (2H, s), 5.38 (1H, dd, J=9.6, 3.6 Hz), 7.12 (1H, d, J=8.6 Hz), 7.22-7.34 (3H, m), 7.40 (1H, t, J=7.8 Hz), 7.44-7.50 (2H, m), 7.54 (1H, s), 7.63 (1H, d, J=8.7 Hz), 7.68-7.84 (5H, m); $^{13}$C NMR (100 MHz, CDCl$_3$) δ 37.2, 38.6, 72.8, 123.6, 125.3, 125.7, 126.0, 126.3, 127.2, 127.6, 127.7, 127.95, 128.04, 128.1, 129.7, 131.9, 132.4, 133.1, 133.3, 133.7, 171.0, 174.8; HRESIMS calcd for C$_{25}$H$_{20}$O$_4$Na [M+Na]$^+$ 407.1259, found 407.1258.

The chemical structure of H-151 found was as follows.
(H-151)

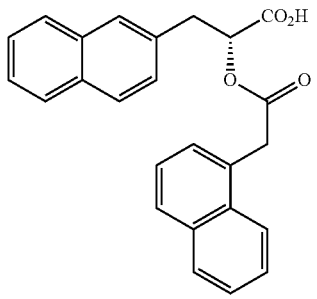 [SMILES: O=C(Cc1cccc2ccccc12)O[C@H](Cc1ccc2ccccc2c1)C(=O)O]

(Example 2-27) Synthesis of H-147

To a solution of H-26 (200 mg, 0.654 mmol) in THF (2 mL), sodium hydride (60%, 31 mg, 0.785 mmol) was added at room temperature, and the resulting mixture was stirred at the same temperature for 15 minutes. To the mixture, a solution of 10H-phenoxazine-10-carbonyl chloride (192 mg, 0.785 mmol) in THF (2 mL) was added at room temperature, and the resulting mixture was stirred at the same temperature for 3 hours, and then at 50° C. for 24 hours. Saturated aqueous ammonium chloride solution was added to the reaction mixture, and extraction was carried out with ethyl acetate. The organic layer was washed with saturated brine, and then dried over anhydrous magnesium sulfate, followed by filtration, and concentration under reduced pressure. The resulting residue was purified by silica gel column chromatography (hexane:ethyl acetate, 6:1), to obtain H-147 as an oily substance (240 mg, 0.466 mmol, 71%).

Regarding H-147, the NMR measurement spectrum and the result of mass spectrometry by HR-ESI-MS were as follows.

$^1$H NMR (400 MHz, CDCl$_3$) δ 3.30 (1H, dd, J=14.2, 7.4 Hz), 3.35 (1H, dd, J=14.2, 5.0 Hz), 5.17 (1H, d, J=12.4 Hz), 5.26 (1H, d, J=12.4 Hz), 5.52 (1H, dd, J=7.4, 5.0 Hz), 6.92-6.98 (2H, m), 7.03-7.07 (2H, m), 7.10-7.19 (3H, m), 7.22-7.33 (5H, m), 7.42-7.51 (5H, m), 7.62-7.77 (2H, m), 7.79-7.84 (1H, m); $^{13}$C NMR (100 MHz, CDCl$_3$) δ 37.4, 67.3, 70.7, 116.6, 123.3, 125.0, 125.8, 126.0, 126.4, 127.4, 127.6, 127.7, 128.06, 128.09, 128.3, 128.4, 128.6, 132.5, 132.9, 133.3, 150.3, 152.3, 169.5; HRESIMS calcd for C$_{33}$H$_{25}$NO$_5$Na [M+Na]$^+$ 538.1630, found 538.1633. The chemical structure of H-147 found was as follows.
(H-147)

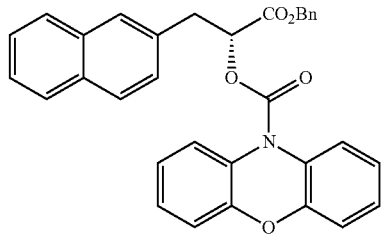

(Example 2-28) Synthesis of H-157

To a solution of H-147 (240 mg, 0.506 mmol) in THF (6 mL), 5% Pd/C (100 mg) was added, and the resulting mixture was stirred under hydrogen atmosphere at room temperature for 18 hours. The reaction mixture was filtered using Celite, and the residue was washed with ethyl acetate, followed by concentration of the solution under reduced pressure, to obtain H-157 as an amorphous substance (180 mg, 0.424 mmol, 99%).

Regarding H-157, the NMR measurement spectrum and the result of mass spectrometry by HR-ESI-MS were as follows.

$^1$H NMR (400 MHz, CDCl$_3$) δ 3.30 (1H, dd, J=14.2, 8.7 Hz), 3.40 (1H, dd, J=14.2, 4.1 Hz), 5.46 (1H, dd, J=8.7, 4.1 Hz), 6.97 (2H, td, J=8.3, 1.4 Hz), 7.04 (2H, dd, J=8.3, 1.4 Hz), 7.13 (2H, ddd, J=8.7, 7.4, 1.4 Hz), 7.24 (2H, dd, J=8.3, 1.8 Hz), 7.40-7.49 (3H, m), 7.55 (1H, s), 7.66-7.71 (1H, m), 7.73 (1H, d, J=8.3 Hz), 7.78-7.84 (1H, m); $^{13}$C NMR (100 MHz, CDCl$_3$) δ 37.2, 74.7, 116.6, 123.3, 125.0, 125.8, 126.0, 126.5, 127.2, 127.6, 127.7, 127.9, 128.2, 128.4, 132.5, 132.8, 133.3, 150.3, 152.4, 175.2; HRESIMS calcd for C$_{26}$H$_{19}$NO$_5$Na [M+Na]$^+$ 448.1161, found 448.1160.

The chemical structure of H-157 found was as follows.
(H-157)

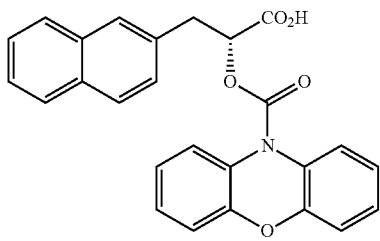 [SMILES: O=C(O)[C@@H](Cc1ccc2ccccc2c1)OC(=O)N1c2ccccc2Oc2ccccc21]

(Example 2-29) Synthesis of H-148

To a solution of H-26 (200 mg, 0.654 mmol) in THF (2 mL), sodium hydride (60%, 31 mg, 0.785 mmol) was added at room temperature, and the resulting mixture was stirred at the same temperature for 15 minutes. To the mixture, a solution of 9H-carbazole-9-carbonyl chloride (180 mg, 0.785 mmol) in THF (2 mL) was added at room temperature, and the resulting mixture was stirred at the same temperature for 3 hours, and then at 50° C. for 18 hours. Saturated aqueous ammonium chloride solution was added to the reaction mixture, and extraction was carried out with ethyl acetate. The organic layer was washed with saturated brine, and then dried over anhydrous magnesium sulfate, followed by filtration, and concentration under reduced pressure. The resulting residue was purified by silica gel column chromatography (hexane:ethyl acetate, 6:1), to obtain H-148 as yellow crystals (245 mg, 0.491 mmol, 75%).

Regarding H-148, the NMR measurement spectrum and the result of mass spectrometry by HR-ESI-MS were as follows.

$^1$H NMR (400 MHz, CDCl$_3$) δ 3.59 (1H, dd, J=14.2, 5.5 Hz), 3.35 (1H, dd, J=14.2, 6.9 Hz), 5.21 (1H, d, J=12.4 Hz), 5.25 (1H, d, J=12.4 Hz), 5.91 (1H, dd, J=6.9, 5.5 Hz), 7.18-7.50 (11H, m), 7.69-7.78 (3H, m), 7.79-7.84 (1H, m), 7.91-7.86 (2H, m), 8.06-8.12 (2H, m), 8.16 (1H, d, J=7.8 Hz); HRESIMS calcd for C$_{33}$H$_{25}$NO$_4$Na [M+Na]$^+$ 522.1681, found 522.1680.

The chemical structure of H-148 found was as follows.
(H-148)

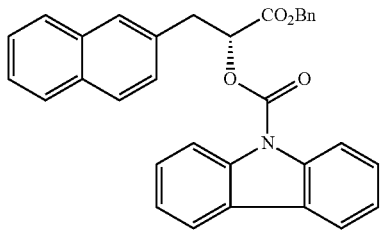

(Example 2-30) Synthesis of H-175

To a solution of H-148 (200 mg, 0.401 mmol) in THF (6 mL), 5% Pd/C (100 mg) was added, and the resulting mixture was stirred under hydrogen atmosphere at room temperature for 18 hours. The reaction mixture was filtered using Celite, and the residue was washed with ethyl acetate, followed by concentration of the solution under reduced pressure, to obtain H-175 as white crystals (151 mg, 0.369 mmol, 92%).

Regarding H-175, the NMR measurement spectrum and the result of mass spectrometry by HR-ESI-MS were as follows.

$^1$H NMR (400 MHz, CDCl$_3$) δ 3.62-3.67 (2H, m), 5.87 (1H, dd, J=6.9, 5.5 Hz), 7.24-7.35 (4H, m), 7.40-7.50 (3H, m), 7.75-7.85 (5H, m), 7.91-7.55 (2H, m), 8.14 (1H, d, J=7.8 Hz); $^{13}$C NMR (100 MHz, CDCl$_3$) δ 37.4, 74.7, 116.5, 119.6, 123.6, 126.0, 126.1, 126.3, 127.0, 127.2, 127.65, 127.69, 128.5, 128.6, 132.59, 132.63, 133.5, 138.0, 151.5, 174.6; HRESIMS calcd for C$_{26}$H$_{19}$NO$_4$Na [M+Na]$^+$ 432.1212, found 432.1212.

The chemical structure of H-175 found was as follows.
(H-175)

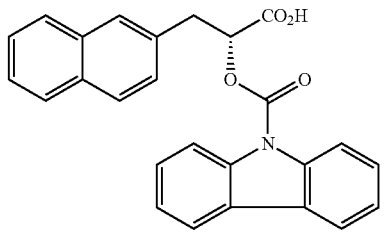 [SMILES: O=C(O)[C@@H](Cc1ccc2ccccc2c1)OC(=O)n1c2ccccc2c2ccccc21]

(Example 2-31) Synthesis of H-167

To a solution of H-26 (200 mg, 0.654 mmol), phenoxyacetic acid (129 mg, 0.85 mmol), and 4-dimethylaminopyridine (8.0 mg, 0.065 mmol) in dichloromethane (5 mL), 1-ethyl-3-(3-dimethylaminopropyl)carbodiimide hydrochloride (163 mg, 0.85 mmol) was added at room temperature, and the resulting mixture was stirred at the same temperature for 2 days. Water was added to the mixture, and extraction was carried out with ethyl acetate. The organic layer was washed with saturated brine, and then dried over anhydrous magnesium sulfate, followed by filtration, and concentration under reduced pressure. The resulting residue was purified by silica gel column chromatography (hexane:ethyl acetate, 6:1), to obtain H-167 as a colorless oily substance (265 mg, 0.602 mmol, 92%).

Regarding H-167, the NMR measurement spectrum and the result of mass spectrometry by HR-ESI-MS were as follows.

$^1$H NMR (400 MHz, CDCl$_3$) δ 3.31 (1H, dd, J=14.2, 8.7 Hz), 3.41 (1H, dd, J=14.2, 4.6 Hz), 4.61 (1H, d, J=16.4 Hz), 4.69 (1H, d, J=16.4 Hz), 5.17 (2H, s), 5.54 (1H, dd, J=8.7, 4.6 Hz), 6.76-6.81 (2H, m), 6.93 (1H, t, J=7.3 Hz), 7.12-7.18 (2H, m), 7.21-7.34 (6H, m), 7.45-7.51 (2H, m), 7.62 (1H, s), 7.71-7.77 (2H, m), 7.79-7.85 (1H, m); $^{13}$C NMR (100 MHz, CDCl$_3$) δ 37.3, 64.9, 67.4, 73.3, 114.5, 121.7, 125.8, 126.2, 127.3, 127.64, 127.65, 128.1, 128.2, 128.3, 128.5, 128.6, 129.5, 132.5, 132.8, 133.4, 134.9, 157.6, 168.5, 168.8; HRESIMS calcd for C$_{28}$H$_{24}$O$_5$Na [M+Na]$^+$ 463.1521, found 463.1516.

The chemical structure of H-167 found was as follows.
(H-167)

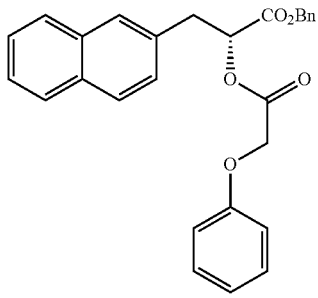 [SMILES: O=C(COc1ccccc1)O[C@H](Cc1ccc2ccccc2c1)C(=O)OCc1ccccc1]

(Example 2-32) Synthesis of H-176

To a solution of H-167 (215 mg, 0.489 mmol) in THF (6 mL), 5% Pd/C (100 mg) was added, and the resulting mixture was stirred under hydrogen atmosphere at room temperature for 8 hours. The reaction mixture was filtered using Celite, and the residue was washed with ethyl acetate, followed by concentration of the solution under reduced pressure, to obtain H-176 as white crystals (169 mg, 0.484 mmol, 99%).

Regarding H-176, the NMR measurement spectrum and the result of mass spectrometry by HR-ESI-MS were as follows.

$^1$H NMR (400 MHz, CDCl$_3$) δ 3.31 (1H, dd, J=14.2, 9.6 Hz), 3.46 (1H, bd, J=14.2 Hz), 4.60 (1H, d, J=16.4 Hz), 4.69 (1H, d, J=16.4 Hz), 5.53 (1H, bd, J=9.6 Hz), 6.78 (2H, d, J=7.7 Hz), 6.93 (1H, t, J=7.4 Hz), 7.15 (2H, t, J=7.4 Hz), 7.34 (1H, d, J=7.8 Hz), 7.44-7.52 (2H, m), 7.68 (1H, s), 7.74-7.86 (3H, m); $^{13}$C NMR (100 MHz, CDCl$_3$) δ37.2, 64.8, 72.8, 114.5, 121.7, 125.9, 126.2, 127.2, 127.7, 128.1, 128.3, 129.5, 132.5, 132.7, 133.4, 157.5, 168.5, 174.3; HRESIMS calcd for C$_{21}$H$_{18}$O$_5$Na [M+Na]$^+$ 373.1052, found 373.1054.

The chemical structure of H-176 found was as follows.
(H-176)

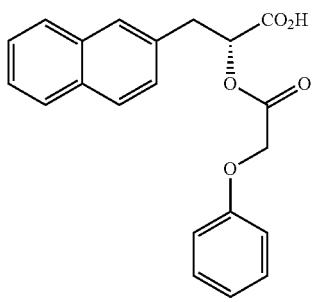 [SMILES: O=C(COc1ccccc1)O[C@H](Cc1ccc2ccccc2c1)C(=O)O]

(Example 2-33) Synthesis of H-168

To a solution of H-26 (200 mg, 0.654 mmol), 2-naphthyloxyacetic acid (172 mg, 0.85 mmol), and 4-dimethylaminopyridine (8.0 mg, 0.065 mmol) in dichloromethane (5 mL), 1-ethyl-3-(3-dimethylaminopropyl)carbodiimide hydrochloride (163 mg, 0.85 mmol) was added at room temperature, and the resulting mixture was stirred at the same temperature for 2 days. Water was added to the mixture, and extraction was carried out with ethyl acetate. The organic layer was washed with saturated brine, and then dried over anhydrous magnesium sulfate, followed by filtration, and concentration under reduced pressure. The resulting residue was purified by silica gel column chromatography (hexane:ethyl acetate, 6:1), to obtain H-168 as a colorless oily substance (318 mg, 0.649 mmol, 99%).

Regarding H-168, the NMR measurement spectrum and the result of mass spectrometry by HR-ESI-MS were as follows.

$^1$H NMR (400 MHz, CDCl$_3$) δ 3.32 (1H, dd, J=14.2, 8.7 Hz), 3.41 (1H, dd, J=14.2, 4.6 Hz), 4.75 (1H, d, J=16.5 Hz), 4.82 (1H, d, J=16.5 Hz), 5.17 (2H, s), 5.55 (1H, dd, J=8.7, 4.6 Hz), 6.98 (1H, d, J=2.3 Hz), 7.16 (1H, dd, J=9.1, 2.3 Hz), 7.20-7.41 (8H, m), 7.44-7.52 (3H, m), 7.63 (1H, s), 7.64-7.81 (5H, m); $^{13}$C NMR (100 MHz, CDCl$_3$) δ 37.3, 65.0, 67.4, 73.5, 107.2, 118.3, 124.0, 125.8, 126.1, 126.4, 126.9, 127.2, 127.5, 127.61, 127.63, 128.1, 128.2, 128.3, 128.5, 128.6, 129.3, 129.6, 132.5, 132.8, 133.3, 134.2, 134.9, 155.5, 168.4, 168.9; HRESIMS calcd for C$_{32}$H$_{26}$O$_5$Na [M+Na]$^+$ 513.1678, found 513.1682.

The chemical structure of H-168 found was as follows.
(H-168)

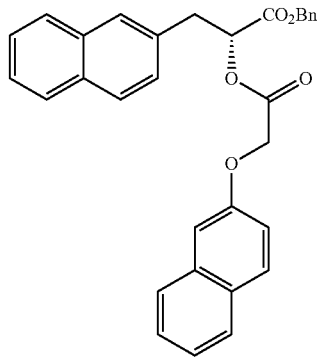 [SMILES: O=C(COc1ccc2ccccc2c1)O[C@H](Cc1ccc2ccccc2c1)C(=O)OCc1ccccc1]

(Example 2-34) Synthesis of H-177

To a solution of H-168 (274 mg, 0.559 mmol) in THF (6 mL), 5% Pd/C (100 mg) was added, and the resulting mixture was stirred under hydrogen atmosphere at room temperature for 8 hours. The reaction mixture was filtered using Celite, and the residue was washed with ethyl acetate, followed by concentration of the solution under reduced pressure, to obtain H-177 as white crystals (219 mg, 0.548 mmol, 98%).

Regarding H-177, the NMR measurement spectrum and the result of mass spectrometry by HR-ESI-MS were as follows.

$^1$H NMR (400 MHz, CDCl$_3$) δ 3.32 (1H, dd, J=14.2, 9.1 Hz), 3.41 (1H, dd, J=14.2, 3.5 Hz), 4.74 (1H, d, J=16.4 Hz), 4.81 (1H, d, J=16.4 Hz), 5.53 (1H, dd, J=9.1, 3.5 Hz), 6.95 (1H, d, J=2.3 Hz), 7.15 (1H, dd, J=9.2, 2.3 Hz), 7.29-7.42 (3H, m), 7.44-7.53 (3H, m), 7.64-7.82 (6H, m); $^{13}$C NMR (100 MHz, CDCl$_3$) δ 37.1, 64.9, 73.0, 107.1, 118.3, 124.1, 125.8, 126.2, 126.4, 126.9, 127.1, 127.58, 127.64, 127.67, 128.1, 128.3, 129.4, 129.7, 132.5, 132.8, 133.4, 134.1, 155.5, 168.5, 174.0; HRESIMS calcd for C$_{25}$H$_{20}$O$_5$Na [M+Na]$^+$ 423.1208, found 423.1209.

The chemical structure of H-177 found was as follows.
(H-177)

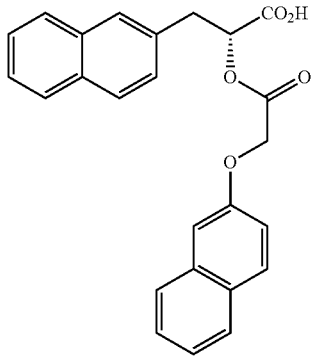 [SMILES: O=C(COc1ccc2ccccc2c1)O[C@H](Cc1ccc2ccccc2c1)C(=O)O]

(Example 2-35) Synthesis of H-169

To a solution of H-26 (200 mg, 0.654 mmol), 1-naphthyloxyacetic acid (172 mg, 0.85 mmol), and 4-dimethylaminopyridine (8.0 mg, 0.065 mmol) in dichloromethane (5 mL), 1-ethyl-3-(3-dimethylaminopropyl)carbodiimide hydrochloride (163 mg, 0.85 mmol) was added at room temperature, and the resulting mixture was stirred at the same temperature for 2 days. Water was added to the mixture, and extraction was carried out with ethyl acetate. The organic layer was washed with saturated brine, and then dried over anhydrous magnesium sulfate, followed by filtration, and concentration under reduced pressure. The resulting residue was purified by silica gel column chromatography (hexane:ethyl acetate, 6:1), to obtain H-169 as a colorless oily substance (299 mg, 0.610 mmol, 93%).

Regarding H-169, the NMR measurement spectrum and the result of mass spectrometry by HR-ESI-MS were as follows.

$^1$H NMR (400 MHz, CDCl$_3$) δ 3.31 (1H, dd, J=14.2, 8.6 Hz), 3.41 (1H, dd, J=14.2, 4.3 Hz), 4.82 (1H, d, J=16.5 Hz), 4.88 (1H, d, J=16.5 Hz), 5.18 (2H, s), 5.56 (1H, dd, J=8.6, 4.3 Hz), 6.53 (1H, d, J=7.7 Hz), 7.10 (1H, t, J=7.8 Hz), 7.22-7.34 (6H, m), 7.38-7.54 (5H, m), 7.60 (1H, s), 7.63-7.69 (2H, m), 7.78-7.83 (2H, m), 8.31 (1H, d, J=8.2 Hz); $^{13}$C NMR (100 MHz, CDCl$_3$) δ 37.3, 65.3, 67.4, 73.4, 104.9, 121.3, 122.1, 125.4, 125.8, 126.1, 126.5, 127.3, 127.4, 127.61, 127.65, 128.1, 128.2, 128.3, 128.5, 128.6, 132.5, 132.8, 133.3, 134.5, 134.9, 153.4, 168.4, 168.9; HRESIMS calcd for C$_{32}$H$_{26}$O$_5$Na [M+Na]$^+$ 513.1678, found 513.1672.

The chemical structure of H-169 found was as follows.
(H-169)

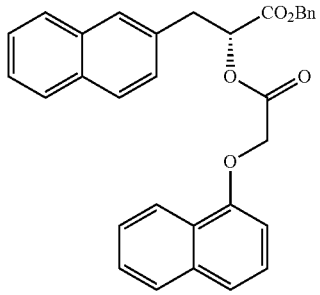 [SMILES: O=C(COc1cccc2ccccc12)O[C@H](Cc1ccc2ccccc2c1)C(=O)OCc1ccccc1]

(Example 2-36) Synthesis of H-179

To a solution of H-169 (262 mg, 0.535 mmol) in THF (6 mL), 5% Pd/C (100 mg) was added, and the resulting mixture was stirred under hydrogen atmosphere at room temperature for 8 hours. The reaction mixture was filtered using Celite, and the residue was washed with ethyl acetate, followed by concentration of the solution under reduced pressure, to obtain H-179 as a white solid (210 mg, 0.525 mmol, 98%).

Regarding H-179, the NMR measurement spectrum and the result of mass spectrometry by HR-ESI-MS were as follows.

$^1$H NMR (400 MHz, CDCl$_3$) δ 3.31 (1H, dd, J=14.6, 9.2 Hz), 3.41 (1H, dd, J=14.6, 3.7 Hz), 4.82 (1H, d, J=16.4 Hz), 4.88 (1H, d, J=16.4 Hz), 5.55 (1H, dd, J=9.2, 3.7 Hz), 6.52 (1H, d, J=7.3 Hz), 7.12 (1H, t, J=7.7 Hz), 7.31 (1H, d, J=8.7 Hz), 7.40 (1H, d, J=8.3 Hz), 7.43-7.54 (4H, m), 7.66 (1H, s), 7.67-7.74 (2H, m), 7.77-7.84 (2H, m), 8.31 (1H, d, J=7.3 Hz); $^{13}$C NMR (100 MHz, CDCl$_3$) δ 37.1, 65.2, 72.9, 104.9, 121.4, 122.1, 125.4, 125.5, 125.8, 126.0, 126.2, 126.6, 127.2, 127.4, 127.7, 128.1, 128.3, 132.5, 132.7, 133.3, 134.5, 153.3, 168.4, 174.2; HRESIMS calcd for C$_{25}$H$_{20}$O$_5$Na [M+Na]$^+$ 423.1208, found 423.1209.

The chemical structure of H-179 found was as follows.
(H-179)

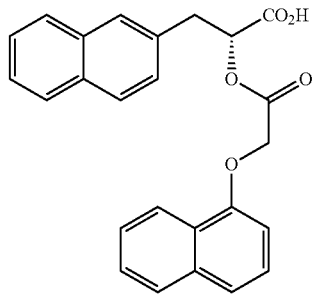 [SMILES: O=C(COc1cccc2ccccc12)O[C@H](Cc1ccc2ccccc2c1)C(=O)O]

(Example 2-37) Synthesis of H-170

To a solution of H-26 (200 mg, 0.654 mmol), 3-indoleacetic acid (149 mg, 0.85 mmol), and 4-dimethylaminopyridine (8.0 mg, 0.065 mmol) in dichloromethane (5 mL), 1-ethyl-3-(3-dimethylaminopropyl)carbodiimide hydrochloride (163 mg, 0.85 mmol) was added at room temperature, and the resulting mixture was stirred at the same temperature for 24 hours. Water was added to the mixture, and extraction was carried out with ethyl acetate. The organic layer was washed with saturated brine, and then dried over anhydrous magnesium sulfate, followed by filtration, and concentration under reduced pressure. The resulting residue was purified by silica gel column chromatography (hexane:ethyl acetate, 4:1), to obtain H-170 as a yellow oily substance (298 mg, 0.644 mmol, 98%).

Regarding H-170, the NMR measurement spectrum and the result of mass spectrometry by HR-ESI-MS were as follows.

$^1$H NMR (400 MHz, CDCl$_3$) δ 3.27 (1H, dd, J=14.2, 8.3 Hz), 3.36 (1H, dd, J=14.2, 4.5 Hz), 3.80 (2H, s), 5.13 (2H, s), 5.44 (1H, dd, J=8.3, 4.5 Hz), 6.89 (1H, s), 7.01 (1H, t, J=7.3 Hz), 7.11-7.38 (8H, m), 7.42-7.52 (3H, m), 7.55 (1H, s), 7.60-7.72 (2H, m), 7.78-7.92 (2H, m); $^{13}$C NMR (100 MHz, CDCl$_3$) δ 30.9, 37.4, 67.1, 73.2, 107.6, 111.1, 118.7, 119.6, 122.1, 123.1, 125.7, 126.0, 127.1, 127.4, 127.59, 127.66, 128.0, 128.1, 128.2, 128.3, 128.5, 132.4, 133.2, 133.3, 135.1, 135.9, 169.5, 171.3; HRESIMS calcd for $C_{30}H_{25}NO_4Na$ $[M+Na]^+$ 486.1681, found 486.1679. The chemical structure of H-170 found was as follows.

(H-170)

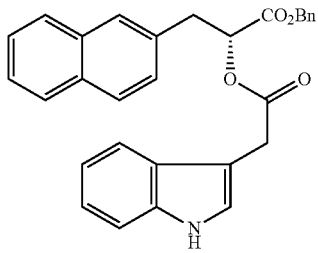 [SMILES: O=C(Cc1c[nH]c2ccccc12)O[C@H](Cc1ccc2ccccc2c1)C(=O)OCc1ccccc1]

(Example 2-38) Synthesis of H-180

To a solution of H-170 (264 mg, 0.570 mmol) in THF (6 mL), 5% Pd/C (100 mg) was added, and the resulting mixture was stirred under hydrogen atmosphere at room temperature for 8 hours. The reaction mixture was filtered using Celite, and the residue was washed with ethyl acetate, followed by concentration of the solution under reduced pressure, to obtain H-180 as a pink powder (204 mg, 0.547 mmol, 96%).

Regarding H-180, the NMR measurement spectrum and the result of mass spectrometry by HR-ESI-MS were as follows.

$^1$H NMR (400 MHz, CDCl$_3$) δ 3.26 (1H, dd, J=14.2, 9.1 Hz), 3.39 (1H, dd, J=14.2, 3.7 Hz), 3.80 (2H, s), 5.41 (1H, dd, J=9.1, 3.7 Hz), 6.86 (1H, s), 7.00 (1H, t, J=7.4 Hz), 7.16 (1H, t, J=7.3 Hz), 7.22-7.30 (2H, m), 7.40-7.51 (3H, m), 7.59 (1H, s), 7.67-7.74 (2H, m), 7.78-7.92 (2H, m); $^{13}$C NMR (100 MHz, CDCl$_3$) δ 30.7, 37.2, 72.7, 107.4, 111.1, 118.6, 119.6, 122.1, 123.2, 125.7, 126.0, 127.0, 127.3, 127.6, 127.7, 128.1, 132.4, 133.2, 133.3, 135.9, 171.6, 174.8; HRESIMS calcd for $C_{23}H_{19}NO_4Na$ $[M+Na]^+$ 396.1212, found 396.1212.

The chemical structure of H-180 found was as follows.
(H-180)

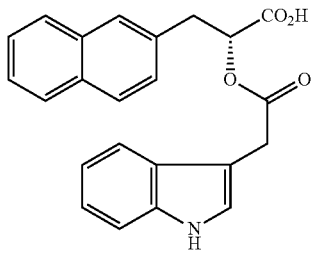 [SMILES: O=C(Cc1c[nH]c2ccccc12)O[C@H](Cc1ccc2ccccc2c1)C(=O)O]

(Example 2-39) Synthesis of H-191

To a solution of H-26 (200 mg, 0.654 mmol), 3,5-dimethoxybenzoic acid (143 mg, 0.785 mmol) and 4-dimethylaminopyridine (8.0 mg, 0.065 mmol) in dichloromethane (5 mL), 1-ethyl-3-(3-dimethylaminopropyl)carbodiimide hydrochloride (163 mg, 0.85 mmol) was added at room temperature, and the resulting mixture was stirred at the same temperature for 16 hours. Water was added to the mixture, and extraction was carried out with ethyl acetate. The organic layer was washed with saturated brine, and then dried over anhydrous magnesium sulfate, followed by filtration, and concentration under reduced pressure. The resulting residue was purified by silica gel column chromatography (hexane:ethyl acetate, 6:1), to obtain H-191 as a colorless oily substance (300 mg, 0.638 mmol, 98%).

Regarding H-191, the NMR measurement spectrum and the result of mass spectrometry by HR-ESI-MS were as follows.

$^1$H NMR (400 MHz, CDCl$_3$) δ 3.45 (1H, dd, J=14.2, 7.8 Hz), 3.49 (1H, dd, J=14.2, 5.5 Hz), 3.77 (6H, s), 5.18 (1H, d, J=12.4 Hz), 5.22 (1H, d, J=12.4 Hz), 5.59 (1H, dd, J=7.8, 5.5 Hz), 6.65 (1H, t, J=2.3 Hz), 7.17 (2H, d, J=2.3 Hz), 7.22-7.34 (5H, m), 7.41 (1H, dd, J=8.2, 1.8 Hz), 7.44-7.50 (2H, m), 7.71-7.84 (4H, m); $^{13}$C NMR (100 MHz, CDCl$_3$) δ 37.5, 55.4, 67.1, 73.5, 106.3, 107.2, 125.7, 126.1, 127.4, 127.53, 127.59, 128.1, 128.2, 128.3, 128.5, 131.1, 132.5, 133.2, 133.4, 135.1, 160.5, 165.7, 169.3; HRESIMS calcd for $C_{29}H_{26}O_6Na$ $[M+Na]^+$ 493.1627, found 493.1620.

The chemical structure of H-170 found was as follows.
(H-191)

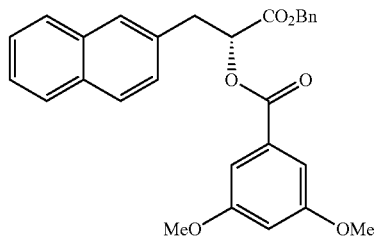 [SMILES: COc1cc(OC)cc(C(=O)O[C@H](Cc2ccc3ccccc3c2)C(=O)OCc2ccccc2)c1]

(Example 2-40) Synthesis of H-198

To a solution of H-191 (246 mg, 0.523 mmol) in THF (6 mL), 5% Pd/C (100 mg) was added, and the resulting mixture was stirred under hydrogen atmosphere at room temperature for 18 hours. The reaction mixture was filtered using Celite, and the residue was washed with ethyl acetate, followed by concentration of the solution under reduced pressure, to obtain H-198 as a white amorphous substance (191 mg, 0.502 mmol, 96%).

Regarding H-198, the NMR measurement spectrum and the result of mass spectrometry by HR-ESI-MS were as follows.

$^1$H NMR (400 MHz, CDCl$_3$) δ 3.45 (1H, dd, J=14.2, 8.3 Hz), 3.53 (1H, dd, J=14.2, 4.6 Hz), 3.76 (6H, s), 5.59 (1H, dd, J=8.3, 4.6 Hz), 6.63 (1H, t, J=2.3 Hz), 7.13 (2H, d, J=2.3 Hz), 7.43-7.49 (3H, m), 7.76-7.83 (4H, m); $^{13}$C NMR (100 MHz, CDCl$_3$) δ 37.4, 55.5, 73.0, 106.5, 107.3, 125.8, 126.2, 127.3, 127.57, 127.65, 128.19, 128.25, 130.8, 132.5, 133.2, 133.4, 160.6, 165.6, 174.9; HRESIMS calcd for $C_{22}H_{20}O_6Na$ $[M+Na]^+$ 403.1158, found 403.1156.

The chemical structure of H-198 found was as follows.
(H-198)

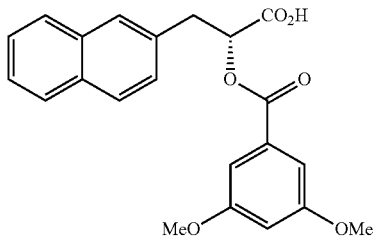 [SMILES: COc1cc(OC)cc(C(=O)O[C@H](Cc2ccc3ccccc3c2)C(=O)O)c1]

(Example 2-41) Synthesis of H-192

To a solution of H-26 (200 mg, 0.654 mmol), 3,5-dichlorobenzoic acid (150 mg, 0.785 mmol), and 4-dimethylaminopyridine (8.0 mg, 0.065 mmol) in dichloromethane (5 mL), 1-ethyl-3-(3-dimethylaminopropyl)carbodiimide hydrochloride (163 mg, 0.85 mmol) was added at room temperature, and the resulting mixture was stirred at the same temperature for 16 hours. Water was added to the mixture, and extraction was carried out with ethyl acetate. The organic layer was washed with saturated brine, and then dried over anhydrous magnesium sulfate, followed by filtration, and concentration under reduced pressure. The resulting residue was purified by silica gel column chromatography (hexane:ethyl acetate, 6:1), to obtain H-192 as white crystals (310 mg, 0.649 mmol, 99%).

Regarding H-192, the NMR measurement spectrum and the result of mass spectrometry by HR-ESI-MS were as follows.

$^1$H NMR (400 MHz, CDCl$_3$) δ3.44 (1H, dd, J=14.2, 7.8 Hz), 3.50 (1H, dd, J=14.2, 5.0 Hz), 5.17 (1H, d, J=12.4 Hz), 5.22 (1H, d, J=12.4 Hz), 5.59 (1H, dd, J=7.8, 5.0 Hz), 7.21-7.26 (2H, m), 7.28-7.34 (3H, m), 7.37 (1H, dd, J=8.7, 1.4 Hz), 7.45-7.51 (2H, m), 7.53 (1H, t, J=2.3 Hz), 7.71 (1H, s), 7.74-7.84 (3H, m), 7.87 (2H, d, J=2.3 Hz); $^{13}$C NMR (100 MHz, CDCl$_3$) δ37.3, 67.4, 73.9, 125.9, 126.2, 127.3, 127.60, 127.64, 128.2, 128.3, 128.5, 128.6, 132.1, 132.5, 132.8, 133.1, 133.4, 134.9, 135.3, 163.6, 168.9; HRESIMS calcd for C$_{27}$H$_{20}$C$_{12}$O$_4$Na [M+Na]$^+$ 501.0636, found 501.0640.

The chemical structure of H-192 found was as follows.
(H-192)

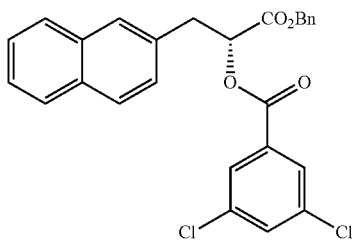 [SMILES: O=C(O[C@H](Cc1ccc2ccccc2c1)C(=O)OCc1ccccc1)c1cc(Cl)cc(Cl)c1]

(Example 2-42) Synthesis of H-200

To a solution of H-192 (268 mg, 0.561 mmol) in THF (5 mL), 5% Pd/C (100 mg) was added, and the resulting mixture was stirred under hydrogen atmosphere at room temperature for 16 hours. The reaction mixture was filtered using Celite, and the residue was washed with ethyl acetate, followed by concentration of the solution under reduced pressure, to obtain H-200 as a white powder (209 mg, 0.539 mmol, 96%).

Regarding H-200, the NMR measurement spectrum and the result of mass spectrometry by HR-ESI-MS were as follows.

$^1$H NMR (400 MHz, CDCl$_3$) δ3.45 (1H, dd, J=14.2, 8.6 Hz), 3.55 (1H, dd, J=14.2, 4.2 Hz), 5.58 (1H, dd, J=8.6, 4.2 Hz), 7.41-7.51 (3H, m), 7.53 (1H, t, J=1.9 Hz), 7.78 (1H, s), 7.80-7.85 (3H, m), 7.86 (2H, d, J=1.9 Hz); $^{13}$C NMR (100 MHz, CDCl$_3$) δ37.3, 73.4, 126.0, 126.3, 127.2, 127.61, 127.66, 128.18, 128.22, 128.4, 131.8, 132.6, 132.7, 133.2, 133.4, 135.3, 163.6, 174.6; HRESIMS calcd for C$_{20}$H$_{14}$C$_{12}$O$_4$Na [M+Na]$^+$ 411.0167, found 411.0163.

The chemical structure of H-200 found was as follows.
(H-200)

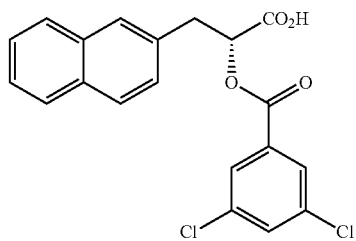 [SMILES: O=C(O[C@H](Cc1ccc2ccccc2c1)C(=O)O)c1cc(Cl)cc(Cl)c1]

(Example 2-43) Synthesis of H-193

To a solution of H-26 (200 mg, 0.654 mmol), 3,5-dimethylbenzoic acid (118 mg, 0.785 mmol), and 4-dimethylaminopyridine (8.0 mg, 0.065 mmol) in dichloromethane (5 mL), 1-ethyl-3-(3-dimethylaminopropyl)carbodiimide hydrochloride (163 mg, 0.85 mmol) was added at room temperature, and the resulting mixture was stirred at the same temperature for 16 hours. Water was added to the mixture, and extraction was carried out with ethyl acetate. The organic layer was washed with saturated brine, and then dried over anhydrous magnesium sulfate, followed by filtration, and concentration under reduced pressure. The resulting residue was purified by silica gel column chromatography (hexane:ethyl acetate, 6:1), to obtain H-193 as a white oily substance (283 mg, 0.646 mmol, 99%).

Regarding H-193, the NMR measurement spectrum and the result of mass spectrometry by HR-ESI-MS were as follows.

$^1$H NMR (400 MHz, CDCl$_3$) δ2.34 (6H, s), 3.42-3.52 (2H, m), 5.16 (1H, d, J=12.4 Hz), 5.21 (1H, d, J=12.4 Hz), 5.60 (1H, dd, J=6.8, 6.0 Hz), 7.17-7.32 (6H, m), 7.40 (1H, dd, J=8.7, 1.8 Hz), 7.43-7.50 (2H, m), 7.65 (2H, s), 7.72-7.84 (4H, m); $^{13}$C NMR (100 MHz, CDCl$_3$) δ21.1, 37.6, 67.1, 73.2, 125.7, 126.1, 127.48, 127.55, 127.62, 128.1, 128.2, 128.3, 128.5, 129.1, 132.5, 133.3, 133.4, 135.0, 135.1, 138.0, 166.2, 169.5; HRESIMS calcd for C$_{29}$H$_{26}$O$_4$Na [M+Na]$^+$ 461.1729, found 461.1724.

The chemical structure of H-193 found was as follows.
(H-193)

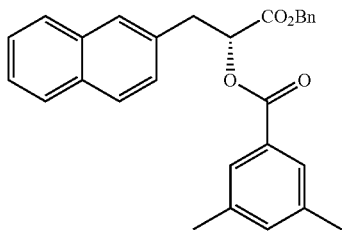

(Example 2-44) Synthesis of H-210

To a solution of H-193 (250 mg, 0.571 mmol) in THF (5 mL), 5% Pd/C (100 mg) was added, and the resulting mixture was stirred under hydrogen atmosphere at room temperature for 18 hours. The reaction mixture was filtered using Celite, and the residue was washed with ethyl acetate, followed by concentration of the solution under reduced pressure, to obtain H-210 as colorless crystals (193 mg, 0.554 mmol, 97%).

Regarding H-210, the NMR measurement spectrum and the result of mass spectrometry by HR-ESI-MS were as follows.

$^1$H NMR (400 MHz, CDCl$_3$) δ2.33 (6H, s), 3.46 (1H, dd, J=14.2, 8.2 Hz), 3.52 (1H, dd, J=14.2, 4.6 Hz), 5.57 (1H, dd, J=8.2, 4.6 Hz), 7.18 (1H, s), 7.42-7.50 (3H, m), 7.62 (2H, s), 7.78-7.85 (4H, m); $^{13}$C NMR (100 MHz, CDCl$_3$) δ21.1, 37.4, 72.7, 125.8, 126.1, 127.4, 127.56, 127.60, 127.65, 128.2, 128.3, 128.9, 132.5, 133.2, 133.4, 135.1, 138.1, 166.2, 175.0; HRESIMS calcd for C$_{22}$H$_{20}$O$_4$Na [M+Na]$^+$ 371.1259, found 371.1261.

The chemical structure of H-210 found was as follows.
(H-210)

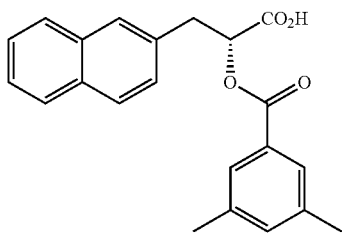 [SMILES: Cc1cc(C)cc(C(=O)O[C@H](Cc2ccc3ccccc3c2)C(=O)O)c1]

(Example 2-45) Synthesis of H-199

To a solution of H-26 (200 mg, 0.654 mmol), 4-dimethylaminobenzoic acid (130 mg, 0.785 mmol), and 4-dimethylaminopyridine (8.0 mg, 0.065 mmol) in dichloromethane (5 mL), 1-ethyl-3-(3-dimethylaminopropyl)carbodiimide hydrochloride (163 mg, 0.85 mmol) was added at room temperature, and the resulting mixture was stirred at the same temperature for 4 days. Water was added to the mixture, and extraction was carried out with ethyl acetate. The organic layer was washed with saturated brine, and then dried over anhydrous magnesium sulfate, followed by filtration, and concentration under reduced pressure. The resulting residue was purified by silica gel column chromatography (hexane:ethyl acetate, 6:1), to obtain H-199 as pale red crystals (283 mg, 0.625 mmol, 96%).

Regarding H-199, the NMR measurement spectrum and the result of mass spectrometry by HR-ESI-MS were as follows.

$^1$H NMR (400 MHz, CDCl$_3$) δ3.01 (6H, s), 3.44 (2H, d, J=6.4 Hz), 5.14 (1H, d, J=12.4 Hz), 5.18 (1H, d, J=12.4 Hz), 5.57 (1H, t, J=6.4 Hz), 6.65 (2H, d, J=9.1 Hz), 7.18-7.31 (5H, m), 7.38-7.48 (4H, m), 7.70 (1H, s), 7.72-7.82 (3H, m), 7.91 (2H, d, J=9.1 Hz); $^{13}$C NMR (100 MHz, CDCl$_3$) δ37.7, 40.0, 66.9, 72.8, 110.7, 116.0, 125.6, 126.0, 127.59, 127.64, 128.0, 128.1, 128.2, 128.4, 131.6, 132.4, 133.4, 133.6, 135.3, 153.5, 166.2, 170.0; HRESIMS calcd for C$_{29}$H$_{27}$NO$_4$Na [M+Na]$^+$ 476.1838, found 476.1841.

The chemical structure of H-199 found was as follows.
(H-199)

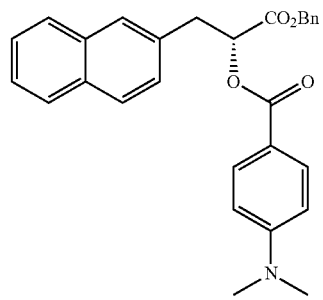 [SMILES: CN(C)c1ccc(C(=O)O[C@H](Cc2ccc3ccccc3c2)C(=O)OCc2ccccc2)cc1]

(Example 2-46) Synthesis of H-212

To a solution of H-199 (242 mg, 0.534 mmol) in THF (5 mL), 5% Pd/C (100 mg) was added, and the resulting mixture was stirred under hydrogen atmosphere at room temperature for 18 hours. The reaction mixture was filtered using Celite, and the residue was washed with ethyl acetate, followed by concentration of the solution under reduced pressure, to obtain H-212 as white crystals (188 mg, 0.518 mmol, 97%).

Regarding H-212, the NMR measurement spectrum and the result of mass spectrometry by HR-ESI-MS were as follows.

$^1$H NMR (400 MHz, CDCl$_3$) δ3.03 (6H, s), 3.43 (1H, dd, J=14.2, 8.3 Hz), 3.49 (1H, dd, J=14.2, 4.6 Hz), 5.55 (1H, dd, J=8.3, 4.6 Hz), 6.61 (2H, d, J=9.1 Hz), 7.40-7.49 (3H, m), 7.77-7.82 (4H, m), 7.89 (2H, d, J=9.1 Hz); $^{13}$C NMR (100 MHz, CDCl$_3$) δ37.5, 40.0, 72.4, 110.8, 115.6, 125.6, 126.0, 127.57, 127.61, 127.65, 128.09, 128.11, 131.6, 132.5, 133.4, 133.6, 153.6, 166.2, 175.2; HRESIMS calcd for C$_{22}$H$_{22}$NO$_4$Na [M+Na]$^+$ 364.1549, found 364.1548.

The chemical structure of H-212 found was as follows.
(H-212)

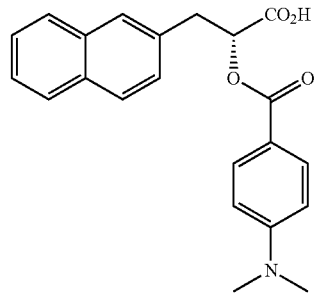 [SMILES: CN(C)c1ccc(C(=O)O[C@H](Cc2ccc3ccccc3c2)C(=O)O)cc1]

(Example 2-47) Synthesis of H-230

To a solution of H-26 (200 mg, 0.654 mmol), L-N-Boc-phenylalanine (208 mg, 0.785 mmol), and 4-dimethylaminopyridine (8.0 mg, 0.065 mmol) in dichloromethane (5 mL), 1-ethyl-3-(3-dimethylaminopropyl)carbodiimide hydrochloride (163 mg, 0.85 mmol) was added at room temperature, and the resulting mixture was stirred at the same temperature for 24 hours. Water was added to the mixture, and extraction was carried out with ethyl acetate. The organic layer was washed with saturated brine, and then dried over anhydrous magnesium sulfate, followed by filtration, and concentration under reduced pressure. The resulting residue was purified by silica gel column chromatography (hexane:ethyl acetate, 4:1), to obtain H-230 as a colorless oily substance (358 mg, 0.647 mmol, 99%).

Regarding H-230, the NMR measurement spectrum and the result of mass spectrometry by HR-ESI-MS were as follows.

$^1$H NMR (400 MHz, CDCl$_3$) δ1.41 (9H, s), 2.85 (1H, dd, J=14.2, 5.9 Hz), 3.03 (1H, dd, J=14.2, 5.4 Hz), 3.26 (1H, dd, J=14.2, 8.7 Hz), 3.36 (1H, dd, J=14.2, 4.6 Hz), 4.69 (1H, ddd, J=8.3, 5.9, 5.4 Hz), 4.92 (1H, d, J=8.3 Hz), 5.13 (1H, d, J=12.4 Hz), 5.17 (1H, d, J=12.4 Hz), 5.34 (1H, dd, J=8.7, 4.6 Hz), 6.67 (2H, d, J=7.3 Hz), 6.99 (2H, t, J=7.3 Hz), 7.08 (1H, t, J=7.3 Hz), 7.20-7.25 (2H, m), 7.28-7.36 (4H, m), 7.42-7.50 (2H, m), 7.67 (1H, s), 7.74-7.82 (3H, m); $^{13}$C NMR (100 MHz, CDCl$_3$) δ28.3, 37.4, 37.9, 54.2, 67.3, 73.9, 79.8, 125.9, 126.2, 126.8, 127.4, 127.59, 127.65, 128.18, 128.23, 128.27, 128.32, 128.4, 128.6, 129.2, 132.6, 133.0, 133.4, 134.9, 135.5, 154.8, 168.8, 171.1; HRESIMS calcd for C$_{34}$H$_{35}$NO$_6$Na [M+Na]$^+$ 576.2362, found 576.2357.

The chemical structure of H-230 found was as follows.
(H-230)

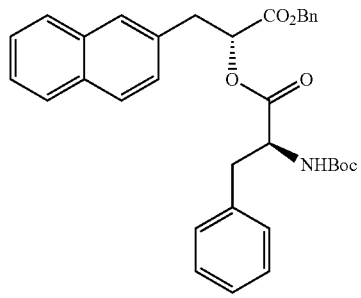

(Example 2-48) Synthesis of H-248

To a solution of H-230 (344 mg, 0.622 mmol) in THF (6 mL), 5% Pd/C (100 mg) was added, and the resulting mixture was stirred under hydrogen atmosphere at room temperature for 16 hours. The reaction mixture was filtered using Celite, and the residue was washed with ethyl acetate, followed by concentration of the solution under reduced pressure, to obtain H-248 as an amorphous substance (282 mg, 0.609 mmol, 98%).

Regarding H-248, the NMR measurement spectrum and the result of mass spectrometry by HR-ESI-MS were as follows.

$^1$H NMR (400 MHz, CDCl$_3$) δ1.30 (9H, s), 2.97 (1H, dd, J=14.2, 6.8 Hz), 3.11 (1H, dd, J=14.2, 5.5 Hz), 3.29 (1H, dd, J=14.2, 7.8 Hz), 3.36 (1H, dd, J=14.2, 4.1 Hz), 4.54 (1H, ddd, J=7.3, 6.8, 5.5 Hz), 4.89 (1H, d, J=7.3 Hz), 5.44 (1H, bs), 7.08-7.26 (6H, m), 7.42-7.50 (2H, m), 7.56 (1H, s), 7.72-7.82 (3H, m); $^{13}$C NMR (100 MHz, CDCl$_3$) δ28.1, 37.2, 37.7, 54.4, 73.4, 80.3, 125.7, 126.1, 126.9, 127.4, 127.59, 127.65, 128.1, 128.4, 129.3, 132.5, 133.0, 133.4, 135.8, 155.4, 171.2, 173.3; HRESIMS calcd for C$_{27}$H$_{29}$NO$_6$Na [M+Na]$^+$ 486.1893, found 486.1892.

The chemical structure of H-248 found was as follows.
(H-248)

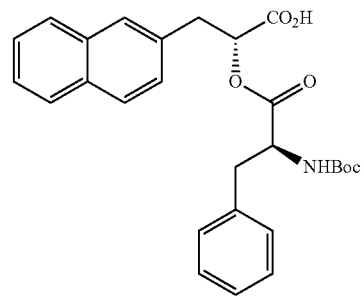

(Example 2-49) Synthesis of H-235

To a solution of H-26 (200 mg, 0.654 mmol), 3,4-dimethylbenzoic acid (117 mg, 0.785 mmol), and 4-dimethylaminopyridine (8.0 mg, 0.065 mmol) in dichloromethane (5 mL), 1-ethyl-3-(3-dimethylaminopropyl)carbodiimide hydrochloride (163 mg, 0.85 mmol) was added at room temperature, and the resulting mixture was stirred at the same temperature for 16 hours. Water was added to the mixture, and extraction was carried out with ethyl acetate. The organic layer was washed with saturated brine, and then dried over anhydrous magnesium sulfate, followed by filtration, and concentration under reduced pressure. The resulting residue was purified by silica gel column chromatography (hexane:ethyl acetate, 6:1), to obtain H-235 as white crystals (292 mg, 0.633 mmol, 97%).

Regarding H-235, the NMR measurement spectrum and the result of mass spectrometry by HR-ESI-MS were as follows.

$^1$H NMR (400 MHz, CDCl$_3$) δ2.28 (3H, s), 2.30 (3H, s), 3.41-3.51 (2H, m), 5.15 (1H, d, J=12.4 Hz), 5.19 (1H, d, J=12.4 Hz), 5.59 (1H, dd, J=7.4, 6.0 Hz), 7.16-7.32 (6H, m), 7.40 (1H, dd, J=8.2, 1.8 Hz), 7.42-7.49 (2H, m), 7.72 (1H, s), 7.73-7.83 (5H, m); $^{13}$C NMR (100 MHz, CDCl$_3$) δ19.7, 20.0, 37.6, 67.0, 73.2, 125.7, 126.0, 126.8, 127.4, 127.5, 127.6, 128.1, 128.2, 128.3, 128.5, 130.0, 130.9, 132.5, 133.3, 133.4, 135.2, 136.7, 142.8, 166.1, 169.6; HRESIMS calcd for C$_{29}$H$_{26}$O$_4$Na [M+Na]$^+$ 461.1729, found 461.1724.

The chemical structure of H-235 found was as follows.
(H-235)

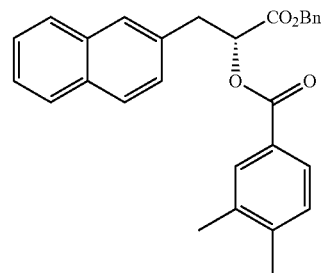 [SMILES: Cc1ccc(C(=O)O[C@H](Cc2ccc3ccccc3c2)C(=O)OCc2ccccc2)cc1C]

(Example 2-50) Synthesis of H-265

To a solution of H-235 (237 mg, 0.542 mmol) in THF (6 mL), 5% Pd/C (100 mg) was added, and the resulting mixture was stirred under hydrogen atmosphere at room temperature for 16 hours. The reaction mixture was filtered using Celite, and the residue was washed with ethyl acetate, followed by concentration of the solution under reduced pressure, to obtain H-265 as white crystals (183 mg, 0.525 mmol, 97%).

Regarding H-265, the NMR measurement spectrum and the result of mass spectrometry by HR-ESI-MS were as follows.

$^1$H NMR (400 MHz, CDCl$_3$) δ2.26 (3H, s), 2.28 (3H, s), 3.44 (1H, dd, J=14.2, 7.8 Hz), 3.50 (1H, dd, J=14.2, 4.6 Hz), 5.55 (1H, dd, J=7.8, 4.6 Hz), 7.16 (1H, d, J=7.4 Hz), 7.42-7.49 (3H, m), 7.72-7.83 (6H, m); $^{13}$C NMR (100 MHz, CDCl$_3$) δ19.6, 20.0, 37.4, 72.7, 125.7, 126.1, 126.6, 127.42, 127.44, 127.6, 128.16, 128.20, 129.7, 130.9, 132.5, 133.37, 133.4, 136.8, 142.9, 166.1; HRESIMS calcd for C$_{22}$H$_{20}$O$_4$Na [M+Na]$^+$ 371.1259, found 371.1263.

The chemical structure of H-265 found was as follows.
(H-265)

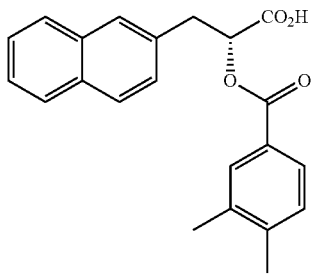 [SMILES: Cc1ccc(C(=O)O[C@H](Cc2ccc3ccccc3c2)C(=O)O)cc1C]

(Example 2-51) Synthesis of H-236

To a solution of H-26 (200 mg, 0.654 mmol), 3,4-dimethoxybenzoic acid (142 mg, 0.785 mmol), and 4-dimethylaminopyridine (8.0 mg, 0.065 mmol) in dichloromethane (5 mL), 1-ethyl-3-(3-dimethylaminopropyl)carbodiimide hydrochloride (163 mg, 0.85 mmol) was added at room temperature, and the resulting mixture was stirred at the same temperature for 16 hours. Water was added to the mixture, and extraction was carried out with ethyl acetate. The organic layer was washed with saturated brine, and then dried over anhydrous magnesium sulfate, followed by filtration, and concentration under reduced pressure. The resulting residue was purified by silica gel column chromatography (hexane:ethyl acetate, 4:1), to obtain H-236 as a colorless oily substance (307 mg, 0.654 mmol, 100%).

Regarding H-236, the NMR measurement spectrum and the result of mass spectrometry by HR-ESI-MS were as follows.

$^1$H NMR (400 MHz, CDCl$_3$) δ3.41-3.51 (2H, m), 3.84 (3H, s), 3.92 (3H, s), 5.16 (1H, d, J=12.4 Hz), 5.21 (1H, d, J=12.4 Hz), 5.58 (1H, dd, J=7.3, 5.9 Hz), 6.87 (1H, d, J=8.7 Hz), 7.20-7.32 (5H, m), 7.40 (1H, dd, J=8.2, 1.8 Hz), 7.42-7.49 (3H, m), 7.67-7.83 (5H, m); $^{13}$C NMR (100 MHz, CDCl$_3$) δ37.6, 55.8, 56.0, 67.1, 73.2, 110.2, 112.0, 121.7, 124.0, 125.7, 126.1, 127.46, 127.53, 127.61, 128.08, 128.15, 128.20, 128.3, 128.5, 132.4, 133.3, 133.4, 135.1, 148.5, 153.2, 165.6, 169.6; HRESIMS calcd for C$_{29}$H$_{26}$O$_6$Na [M+Na]$^+$ 493.1627, found 493.1630.

The chemical structure of H-236 found was as follows.
(H-236)

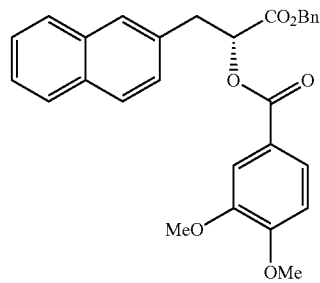 [SMILES: COc1ccc(C(=O)O[C@H](Cc2ccc3ccccc3c2)C(=O)OCc2ccccc2)cc1OC]

(Example 2-52) Synthesis of H-266

To a solution of H-236 (247 mg, 0.526 mmol) in THF (6 mL), 5% Pd/C (100 mg) was added, and the resulting mixture was stirred under hydrogen atmosphere at room temperature for 16 hours. The reaction mixture was filtered using Celite, and the residue was washed with ethyl acetate, followed by concentration of the solution under reduced pressure, to obtain H-266 as a colorless oily substance (196 mg, 0.515 mmol, 98%).

Regarding H-266, the NMR measurement spectrum and the result of mass spectrometry by HR-ESI-MS were as follows.

$^1$H NMR (400 MHz, CDCl$_3$) δ3.45 (1H, dd, J=14.2, 8.3 Hz), 3.52 (1H, dd, J=14.2, 4.6 Hz), 3.83 (3H, s), 3.91 (3H, s), 5.55 (1H, dd, J=8.3, 4.6 Hz), 6.85 (1H, d, J=8.3 Hz), 7.41-7.50 (4H, m), 7.67 (1H, dd, J=8.2, 1.8 Hz), 7.76-7.83 (4H, m); $^{13}$C NMR (100 MHz, CDCl$_3$) δ37.4, 55.8, 56.0, 72.7, 110.3, 112.0, 121.4, 124.0, 125.8, 126.2, 127.4, 127.54, 127.64, 128.2, 132.5, 133.3, 133.4, 148.6, 153.4, 165.6; HRESIMS calcd for C$_{22}$H$_{20}$O$_6$Na [M+Na]$^+$ 403.1158, found 403.1160.

The chemical structure of H-266 found was as follows.
(H-266)

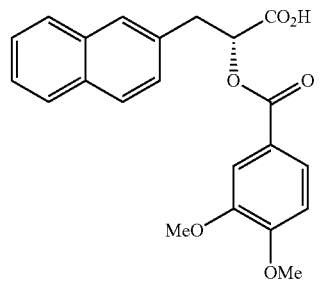 [SMILES: COc1ccc(C(=O)O[C@H](Cc2ccc3ccccc3c2)C(=O)O)cc1OC]

(Example 2-53) Synthesis of H-259

To a solution of H-26 (200 mg, 0.654 mmol), 3,4-dichlorobenzoic acid (162 mg, 0.85 mmol), and 4-dimethylaminopyridine (8.0 mg, 0.065 mmol) in dichloromethane (6 mL), 1-ethyl-3-(3-dimethylaminopropyl)carbodiimide hydrochloride (163 mg, 0.85 mmol) was added at room temperature, and the resulting mixture was stirred at the same temperature for 16 hours. Water was added to the mixture, and extraction was carried out with ethyl acetate. The organic layer was washed with saturated brine, and then dried over anhydrous magnesium sulfate, followed by filtration, and concentration under reduced pressure. The resulting residue was purified by silica gel column chromatography (hexane:ethyl acetate, 6:1), to obtain H-259 as white crystals (305 mg, 0.638 mmol, 98%).

Regarding H-259, the NMR measurement spectrum and the result of mass spectrometry by HR-ESI-MS were as follows.

$^1$H NMR (400 MHz, CDCl$_3$) δ3.43 (1H, dd, J=14.2, 7.7 Hz), 3.48 (1H, dd, J=14.2, 5.1 Hz), 5.16 (1H, d, J=12.4 Hz), 5.21 (1H, d, J=12.4 Hz), 5.58 (1H, dd, J=7.7, 5.1 Hz), 7.21-7.33 (5H, m), 7.36 (1H, dd, J=10.5, 1.8 Hz), 7.43-7.51 (3H, m), 7.69 (1H, s), 7.73-7.85 (4H, m), 8.09 (1H, d, J=1.6 Hz); $^{13}$C NMR (100 MHz, CDCl$_3$) δ37.5, 67.3, 73.8, 125.9, 126.2, 127.3, 127.58, 127.64, 128.2, 128.3, 128.5, 128.6, 128.8, 129.1, 130.6, 131.7, 132.5, 132.9, 133.0, 133.4, 134.9, 138.0, 164.0, 169.0; HRESIMS calcd for C$_{27}$H$_{20}$C$_{12}$O$_4$Na [M+Na]$^+$ 501.0636, found 501.0632. The chemical structure of H-259 found was as follows.

(H-259)

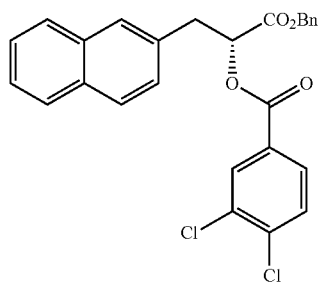

(Example 2-54) Synthesis of H-269

To a solution of H-259 (290 mg, 0.607 mmol) in THF (6 mL), 5% Pd/C (100 mg) was added, and the resulting mixture was stirred under hydrogen atmosphere at room temperature for 16 hours. The reaction mixture was filtered using Celite, and the residue was washed with ethyl acetate, followed by concentration of the solution under reduced pressure, to obtain H-269 as white crystals (230 mg, 0.593 mmol, 98%).

Regarding H-269, the NMR measurement spectrum and the result of mass spectrometry by HR-ESI-MS were as follows.

$^1$H NMR (400 MHz, CDCl$_3$) δ3.45 (1H, dd, J=14.2, 8.7 Hz), 3.53 (1H, dd, J=14.2, 4.2 Hz), 5.57 (1H, dd, J=8.7, 4.2 Hz), 7.40-7.52 (4H, m), 7.77 (1H, s), 7.77-7.85 (4H, m), 8.07 (1H, d, J=1.8 Hz); $^{13}$C NMR (100 MHz, CDCl$_3$) δ37.3, 73.2, 126.0, 126.3, 127.2, 127.6, 127.7, 128.2, 128.4, 128.80, 128.83, 130.6, 131.7, 132.5, 132.8, 133.1, 133.4, 138.2, 164.0, 174.6; HRESIMS calcd for C$_{20}$H$_{14}$Cl$_2$O$_4$Na [M+Na]$^+$ 411.0167, found 411.0170.

The chemical structure of H-269 found was as follows.
(H-269)

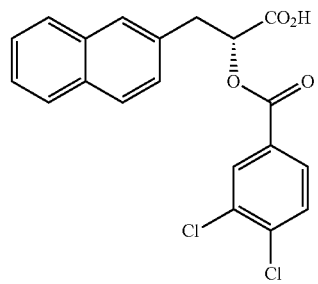

(Example 2-55) Synthesis of H-260

To a solution of H-26 (200 mg, 0.654 mmol), 3,4-difluorobenzoic acid (134 mg, 0.85 mmol), and 4-dimethylaminopyridine (8.0 mg, 0.065 mmol) in dichloromethane (6 mL), 1-ethyl-3-(3-dimethylaminopropyl)carbodiimide hydrochloride (163 mg, 0.85 mmol) was added at room temperature, and the resulting mixture was stirred at the same temperature for 16 hours. Water was added to the mixture, and extraction was carried out with ethyl acetate. The organic layer was washed with saturated brine, and then dried over anhydrous magnesium sulfate, followed by filtration, and concentration under reduced pressure. The resulting residue was purified by silica gel column chromatography (hexane:ethyl acetate, 6:1), to obtain H-260 as white crystals (263 mg, 0.590 mmol, 90%).

Regarding H-260, the NMR measurement spectrum and the result of mass spectrometry by HR-ESI-MS were as follows.

$^1$H NMR (400 MHz, CDCl$_3$) δ3.43 (1H, dd, J=14.2, 7.7 Hz), 3.49 (1H, dd, J=14.2, 5.0 Hz), 5.16 (1H, d, J=12.4 Hz), 5.21 (1H, d, J=12.4 Hz), 5.59 (1H, dd, J=7.7, 5.0 Hz), 7.16-7.35 (5H, m), 7.37 (1H, dd, J=8.2, 1.8 Hz), 7.44-7.51 (2H, m), 7.69 (1H, s), 7.73-7.87 (5H, m); $^{13}$C NMR (100 MHz, CDCl$_3$) δ37.5, 67.3, 73.7, 117.5 (d, J=18.3 Hz), 119.1 (d, J=19.2 Hz), 125.8, 126.2, 126.8, 127.3, 127.56, 127.64, 128.1, 128.3, 128.4, 128.5, 132.5, 132.9, 133.4, 134.9, 150.0 (d, J=249.5, 13.5 Hz), 153.8 (d, J=257.3, 12.5 Hz), 164.0, 169.1; HRESIMS calcd for C$_{27}$H$_{20}$F$_2$O$_5$Na [M+Na]$^+$ 469.1227, found 469.1229.

The chemical structure of H-260 found was as follows.
(H-260)

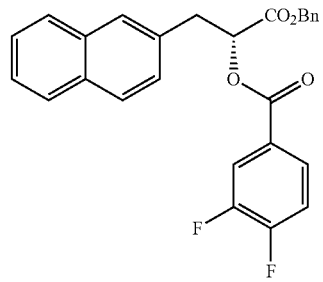 [SMILES: O=C(O[C@H](Cc1ccc2ccccc2c1)C(=O)OCc1ccccc1)c1ccc(F)c(F)c1]

(Example 2-56) Synthesis of H-270

To a solution of H-260 (230 mg, 0.516 mmol) in THF (6 mL), 5% Pd/C (100 mg) was added, and the resulting mixture was stirred under hydrogen atmosphere at room temperature for 16 hours. The reaction mixture was filtered using Celite, and the residue was washed with ethyl acetate, followed by concentration of the solution under reduced pressure, to obtain H-270 as a colorless oily substance (179 mg, 0.502 mmol, 97%).

Regarding H-270, the NMR measurement spectrum and the result of mass spectrometry by HR-ESI-MS were as follows.

$^1$H NMR (400 MHz, CDCl$_3$) δ3.36-3.56 (2H, m), 5.54 (1H, bs), 7.12-7.22 (1H, m), 7.38-7.50 (3H, m), 7.72-7.86 (6H, m); $^{13}$C NMR (100 MHz, CDCl$_3$) δ37.3, 73.6, 117.4 (d, J=17.1 Hz), 119.1 (d, J=18.3 Hz), 125.9, 126.0, 126.3, 126.8, 127.2, 127.5, 127.6, 128.1, 128.3, 132.5, 133.0, 133.4, 150.1 (d, J=250.5, 12.6 Hz), 153.9 (d, J=257.2, 12.5 Hz), 164.1, 175.0; HRESIMS calcd for C$_{20}$H$_{14}$F$_2$O$_4$Na [M+Na]$^+$ 379.0758, found 379.0760.

The chemical structure of H-270 found was as follows.
(H-270)

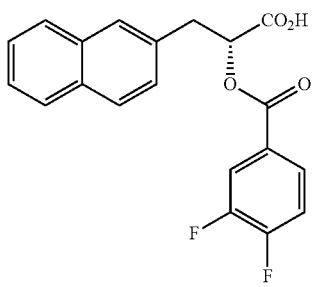 [SMILES: O=C(O[C@H](Cc1ccc2ccccc2c1)C(=O)O)c1ccc(F)c(F)c1]

(Example 2-57) Synthesis of H-250

To a solution of H-26 (200 mg, 0.654 mmol), 2-methoxyfluorene-9-carboxylic acid (H-224) (201 mg, 0.785 mmol), and 4-dimethylaminopyridine (8.0 mg, 0.065 mmol) in dichloromethane (6 mL), 1-ethyl-3-(3-dimethylaminopropyl)carbodiimide hydrochloride (163 mg, 0.85 mmol) was added at room temperature, and the resulting mixture was stirred at the same temperature for 18 hours. Water was added to the mixture, and extraction was carried out with ethyl acetate. The organic layer was washed with saturated brine, and then dried over anhydrous magnesium sulfate, followed by filtration, and concentration under reduced pressure. The resulting residue was purified by silica gel column chromatography (hexane:ethyl acetate, 4:1), to obtain H-250 as white crystals of a 1.7:1.3 diastereomeric mixture (277 mg, 0.525 mmol, 80%).

Regarding H-250, the NMR measurement spectrum and the result of mass spectrometry by HR-ESI-MS were as follows.

$^1$H NMR (400 MHz, CDCl$_3$) δ3.21-3.29 (1H, m), 3.31-3.39 (1H, m), 3.52 (1.3H, s), 3.65 (1.7H, s), 4.81 (0.55H, s), 4.82 (0.45H, s), 5.09-5.18 (2H, m), 5.41-5.47 (1H, m), 6.84-6.94 (2H, m), 7.04-7.37 (9H, m), 7.42-7.72 (7H, m), 7.77-7.84 (1H, m); HRESIMS calcd for C$_{35}$H$_{28}$O$_5$Na [M+Na]$^+$ 551.1834, found 551.1833.

The chemical structure of H-250 found was as follows.
(H-250)

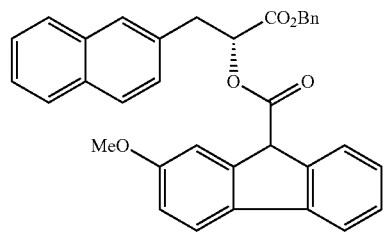 [SMILES: COc1ccc2c(c1)C(C(=O)O[C@H](Cc1ccc3ccccc3c1)C(=O)O)c1ccccc1-2]

(Example 2-58) Synthesis of H-254

To a solution of H-250 (242 mg, 0.458 mmol) in THF (6 mL), 5% Pd/C (100 mg) was added, and the resulting mixture was stirred under hydrogen atmosphere at room temperature for 16 hours. The reaction mixture was filtered using Celite, and the residue was washed with ethyl acetate, followed by concentration of the solution under reduced pressure, to obtain H-254 as colorless crystals of a 1.7:1.3 diastereomeric mixture (191 mg, 0.436 mmol, 95%).

Regarding H-254, the NMR measurement spectrum and the result of mass spectrometry by HR-ESI-MS were as follows.

$^1$H NMR (400 MHz, CDCl$_3$) δ3.21-3.29 (1H, m), 3.34-3.45 (1H, m), 3.55 (1.4H, s), 3.66 (1.7H, s), 4.83 (1H, bs), 5.09-5.18 (2H, m), 5.39-5.45 (1H, m), 6.86-6.95 (2H, m), 7.04-7.21 (2H, m), 7.26-7.37 (1H, m), 7.42-7.52 (3H, m), 7.53-7.76 (5H, m), 7.77-7.85 (1H, m); HRESIMS calcd for C$_{28}$H$_{22}$O$_5$Na [MNa]$^+$ 461.1365, found 461.1366.

The chemical structure of H-254 found was as follows.
(H-254)

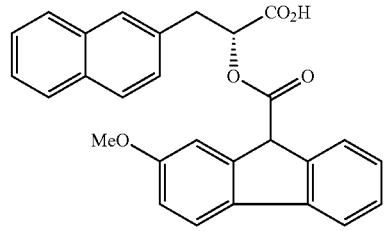

(Example 2-59) Synthesis of H-251

To a solution of H-26 (200 mg, 0.654 mmol), 2-fluoro-fluorene-9-carboxylic acid (H-246) (194 mg, 0.785 mmol), and 4-dimethylaminopyridine (8.0 mg, 0.065 mmol) in dichloromethane (6 mL), 1-ethyl-3-(3-dimethylaminopropyl)carbodiimide hydrochloride (163 mg, 0.85 mmol) was added at room temperature, and the resulting mixture was stirred at the same temperature for 18 hours. Water was added to the mixture, and extraction was carried out with ethyl acetate. The organic layer was washed with saturated brine, and then dried over anhydrous magnesium sulfate, followed by filtration, and concentration under reduced pressure. The resulting residue was purified by silica gel column chromatography (hexane:ethyl acetate, 9:1), to obtain H-251 as white crystals of a 1:1 diastereomeric mixture (276 mg, 0.535 mmol, 82%).

Regarding H-251, the NMR measurement spectrum and the result of mass spectrometry by HR-ESI-MS were as follows.

¹H NMR (400 MHz, CDCl₃) δ3.26 (1H, dd, J=14.2, 8.7 Hz), 3.33-3.43 (1H, m), 4.81 (0.5H, s), 4.82 (0.5H, s), 5.08-5.20 (2H, m), 5.41-5.47 (1H, m), 6.88 (0.5H, td, J=7.8, 1.4 Hz), 6.98-7.38 (10.5H, m), 7.44-7.75 (7H, m), 7.79-7.86 (1H, m); HRESIMS calcd for C₃₄H₂₅FO₄Na [M+Na]⁺ 539.1635, found 539.1631.

The chemical structure of H-251 found was as follows. (H-251)

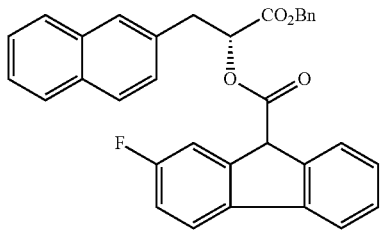 [SMILES: O=C(O[C@H](Cc1ccc2ccccc2c1)C(=O)OCc1ccccc1)C1c2ccccc2-c2ccc(F)cc21]

(Example 2-60) Synthesis of H-262

To a solution of H-251 (242 mg, 0.469 mmol) in THF (6 mL), 5% Pd/C (100 mg) was added, and the resulting mixture was stirred under hydrogen atmosphere at room temperature for 16 hours. The reaction mixture was filtered using Celite, and the residue was washed with ethyl acetate, followed by concentration of the solution under reduced pressure, to obtain H-262 as a white amorphous substance of a 1:1 diastereomeric mixture (182 mg, 0.427 mmol, 91%).

Regarding H-262, the NMR measurement spectrum and the result of mass spectrometry by HR-ESI-MS were as follows.

¹H NMR (400 MHz, CDCl₃) δ3.22-3.31 (1H, m), 3.38-3.48 (1H, m), 4.83 (0.5H, s), 4.84 (0.5H, s), 5.39-5.45 (1H, m), 6.89 (0.5H, td, J=7.8, 1.4 Hz), 7.02-7.40 (5.5H, m), 7.45-7.78 (7H, m), 7.80-7.86 (1H, m); HRESIMS calcd for C₂₇H₁₉FO₄Na [M+Na]⁺ 449.1165, found 449.1168.

The chemical structure of H-262 found was as follows. (H-262)

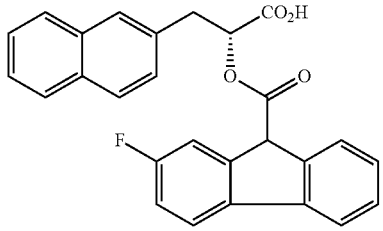

(Example 2-61) Synthesis of H-255

To a solution of H-26 (200 mg, 0.654 mmol), 2-chlorofluorene-9-carboxylic acid (H-237) (192 mg, 0.785 mmol), and 4-dimethylaminopyridine (8.0 mg, 0.065 mmol) in dichloromethane (6 mL), 1-ethyl-3-(3-dimethylaminopropyl)carbodiimide hydrochloride (163 mg, 0.85 mmol) was added at room temperature, and the resulting mixture was stirred at the same temperature for 16 hours. Water was added to the mixture, and extraction was carried out with ethyl acetate. The organic layer was washed with saturated brine, and then dried over anhydrous magnesium sulfate, followed by filtration, and concentration under reduced pressure. The resulting residue was purified by silica gel column chromatography (hexane:ethyl acetate, 9:1), to obtain H-255 as colorless crystals of a 1:1 diastereomeric mixture (340 mg, 0.639 mmol, 98%).

Regarding H-255, the NMR measurement spectrum and the result of mass spectrometry by HR-ESI-MS were as follows.

¹H NMR (400 MHz, CDCl₃) δ3.22-3.31 (1H, m), 3.34-3.43 (1H, m), 4.82 (0.5H, s), 4.83 (0.5H, s), 5.10-5.22 (2H, m), 5.41-5.48 (1H, m), 6.90 (0.5H, td, J=7.3, 0.9 Hz), 7.10-7.40 (9.5H, m), 7.44-7.75 (8H, m), 7.79-7.86 (1H, m); HRESIMS calcd for C₃₄H₂₅ClO₄Na [M+Na]⁺ 555.1339, found 555.1331.

The chemical structure of H-255 found was as follows. (H-255)

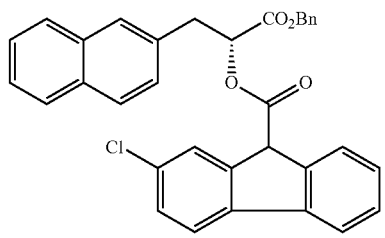 [SMILES: O=C(O[C@H](Cc1ccc2ccccc2c1)C(=O)OCc1ccccc1)C1c2ccccc2-c2ccc(Cl)cc21]

(Example 2-62) Synthesis of H-263

To a solution of H-255 (299 mg, 0.562 mmol) in THF (6 mL), 5% Pd/C (100 mg) was added, and the resulting mixture was stirred under hydrogen atmosphere at room temperature for 16 hours. The reaction mixture was filtered using Celite, and the residue was washed with ethyl acetate, followed by concentration of the solution under reduced pressure, to obtain H-263 as a white amorphous substance of a 1:1 diastereomeric mixture (244 mg, 0.552 mmol, 98%).

Regarding H-263, the NMR measurement spectrum and the result of mass spectrometry by HR-ESI-MS were as follows.

¹H NMR (400 MHz, CDCl₃) δ3.22-3.32 (1H, m), 3.38-3.48 (1H, m), 4.82-4.86 (1H, m), 5.39-5.45 (1H, m), 6.91 (0.5H, td, J=7.3, 0.9 Hz), 7.12-7.41 (4.5H, m), 7.44-7.78 (8H, m), 7.80-7.87 (1H, m); HRESIMS calcd for C₂₇H₁₉ClO₄Na [M+Na]⁺ 465.0870, found 465.0874.

The chemical structure of H-263 found was as follows. (H-263)

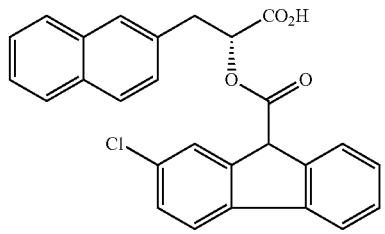 [SMILES: O=C(O[C@H](Cc1ccc2ccccc2c1)C(=O)O)C1c2ccccc2-c2ccc(Cl)cc21]

(Example 2-63) Synthesis of H-419

To a suspension of D-1-naphthylalanine hydrochloride (5.3 g, 21.1 mmol) in water (20 mL), 1 M sulfuric acid (30 mL) and acetone (160 mL) were added at room temperature, and the resulting mixture was cooled to −5° C., followed by slowly adding a solution of sodium nitrite (4.4 g, 63.3 mmol) in water (20 mL) thereto. The resulting mixture was stirred at −5° C. for 30 minutes, and then further stirred at room temperature for 16 hours. After removing acetone under reduced pressure, the mixture was extracted with ethyl acetate. The organic layer was washed with saturated brine, and then dried over anhydrous magnesium sulfate, followed by filtration, and concentration under reduced pressure, to obtain the compound represented by the following structural formula (H-401). This was used for the subsequent step without purification. The purity was about 50%.

(H-401)

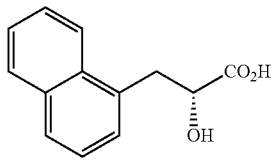 [SMILES: O=C(O)[C@H](O)Cc1cccc2ccccc12]

A solution of a crude product of H-401 (purity, about 50%), benzylalcohol (2.51 g, 2.4 mL, 23.2 mmol), and p-toluenesulfonic acid monohydrate (400 mg, 2.1 mmol) in benzene (70 mL) was refluxed, and stirred for 13 hours while performing azeotropic dehydration. After cooling the mixture to room temperature, a saturated sodium hydrogen carbonate solution was added thereto, followed by extraction with ethyl acetate. The organic layer was washed with saturated brine, and then dried over anhydrous magnesium sulfate, followed by filtration, and concentration under reduced pressure. The resulting residue was purified by silica gel column chromatography (hexane:ethyl acetate, 4:1), to obtain H-414 as a brown oily substance (3.0 g, 9.8 mmol, two steps, 46%).

Regarding H-414, the NMR measurement spectrum and the result of mass spectrometry by HR-ESI-MS were as follows.

$^1$H NMR (400 MHz, CDCl$_3$) δ3.37 (1H, dd, J=14.2, 7.3 Hz), 3.68 (1H, dd, J=14.2, 4.6 Hz), 4.64 (1H, dd, J=7.3, 4.6 Hz), 5.12 (1H, d, J=12.4 Hz), 5.18 (1H, d, J=12.4 Hz), 7.26-7.40 (7H, m), 7.41-7.56 (2H, m), 7.76 (1H, d, J=7.8 Hz), 7.84-7.88 (1H, m), 8.08 (1H, d, J=7.8 Hz); HRESIMS calcd for C$_{20}$H$_{18}$O$_3$Na [M+Na]$^+$ 329.1154, found 329.1151.

The chemical structure of H-414 found was as follows.

(H-414)

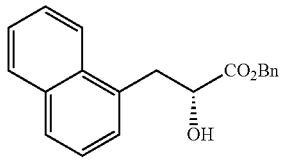 [SMILES: O=C(OCc1ccccc1)[C@H](O)Cc1cccc2ccccc12]

To a solution of H-414 (200 mg, 0.654 mmol), naphthalene-2-carboxylic acid (135 mg, 0.785 mmol), and 4-dimethylaminopyridine (8 mg, 0.065 mmol) in dichloromethane (5 mL), 1-ethyl-3-(3-dimethylaminopropyl)carbodiimide hydrochloride (163 mg, 0.85 mmol) was added at room temperature, and the resulting mixture was stirred at room temperature for 17 hours. Water was added to the mixture, and extraction was carried out with ethyl acetate. The organic layer was washed with saturated brine, and then dried over anhydrous magnesium sulfate, followed by filtration, and concentration under reduced pressure. The resulting residue was purified by silica gel column chromatography (hexane:ethyl acetate, 5:1), to obtain H-419 as a pale yellow oily substance (214 mg, 0.465 mmol, 71%).

Regarding H-419, the NMR measurement spectrum and the result of mass spectrometry by HR-ESI-MS were as follows.

$^1$H NMR (400 MHz, CDCl$_3$) δ3.76 (1H, dd, J=14.2, 8.7 Hz), 3.86 (1H, dd, J=14.2, 5.1 Hz), 5.21 (2H, s), 5.66 (1H, dd, J=8.7, 5.1 Hz), 7.25-7.46 (7H, m), 7.50-7.62 (4H, m), 7.77 (1H, d, J=7.8 Hz), 7.80-7.92 (4H, m), 7.94 (1H, dd, J=8.7, 1.3 Hz), 8.24 (1H, d, J=8.2 Hz), 8.44 (1H, bs); HRESIMS calcd for C$_{31}$H$_{24}$O$_4$Na [M+Na]$^+$ 483.1572, found 483.1572.

The chemical structure of H-419 found was as follows.

(H-419)

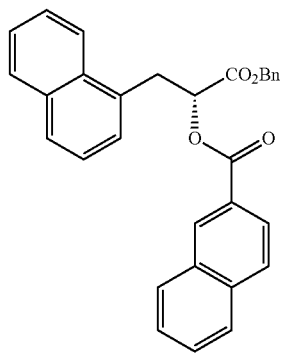 [SMILES: O=C(O[C@H](Cc1cccc2ccccc12)C(=O)OCc1ccccc1)c1ccc2ccccc2c1]

(Example 2-64) Synthesis of H-438

To a solution of H-419 (194 mg, 0.422 mmol) in THF (5 mL), 5% Pd/C (100 mg) was added, and the resulting mixture was stirred under hydrogen atmosphere at room temperature for 16 hours. The reaction mixture was filtered using Celite, and the residue was washed with ethyl acetate, followed by concentration of the solution under reduced pressure. The resulting residue was purified by silica gel column chromatography (chloroform:methanol, 9:1), to obtain H-438 as a white powder (133 mg, 0.359 mmol, 85%).

Regarding H-438, the NMR measurement spectrum and the result of mass spectrometry by HR-ESI-MS were as follows.

$^1$H NMR (400 MHz, CDCl$_3$) δ3.77 (1H, dd, J=14.2, 9.6 Hz), 3.94 (1H, dd, J=14.2, 3.8 Hz), 5.65 (1H, dd, J=9.6, 3.8 Hz), 7.35-7.65 (4H, m), 7.74-7.96 (4H, m), 8.27 (1H, d, J=8.2 Hz), 8.40 (1H, bs); HRESIMS calcd for C$_{24}$H$_{18}$O$_4$Na [M+Na]$^+$ 393.1103, found 393.1099.

The chemical structure of H-438 found was as follows.
(H-438)

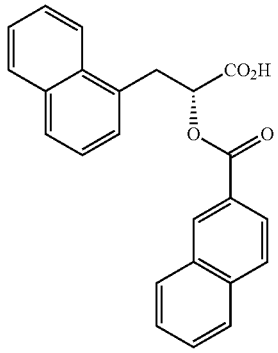 [SMILES: O=C(O[C@H](Cc1cccc2ccccc12)C(=O)O)c1ccc2ccccc2c1]

(Example 2-65) Synthesis of H-420

To a solution of H-414 (200 mg, 0.654 mmol), fluorene-9-carboxylic acid (165 mg, 0.785 mmol), and 4-dimethylaminopyridine (8 mg, 0.065 mmol) in dichloromethane (5 mL), 1-ethyl-3-(3-dimethylaminopropyl)carbodiimide hydrochloride (163 mg, 0.85 mmol) was added at room temperature, and the resulting mixture was stirred at room temperature for 17 hours. Water was added to the mixture, and extraction was carried out with ethyl acetate. The organic layer was washed with saturated brine, and then dried over anhydrous magnesium sulfate, followed by filtration, and concentration under reduced pressure. The resulting residue was purified by silica gel column chromatography (hexane:ethyl acetate, 9:1), to obtain H-420 as a pale yellow oily substance (128 mg, 0.257 mmol, 39%).

Regarding H-420, the NMR measurement spectrum and the result of mass spectrometry by HR-ESI-MS were as follows.
$^1$H NMR (400 MHz, CDCl$_3$) δ3.52 (1H, dd, J=14.6, 9.6 Hz), 3.74 (1H, dd, J=14.6, 4.1 Hz), 4.79 (1H, s), 5.14 (2H, s), 5.46 (1H, dd, J=9.6, 4.1 Hz), 7.10-7.15 (2H, m), 7.19-7.25 (4H, m), 7.29-7.52 (9H, m), 7.68-7.72 (2H, m), 7.77 (1H, d, J=8.2 Hz), 7.85-7.89 (1H, m), 8.02-8.09 (1H, m); HRESIMS calcd for C$_{34}$H$_{26}$O$_4$Na [M+Na]$^+$ 521.1729, found 521.1730.

The chemical structure of H-420 found was as follows.
(H-420)

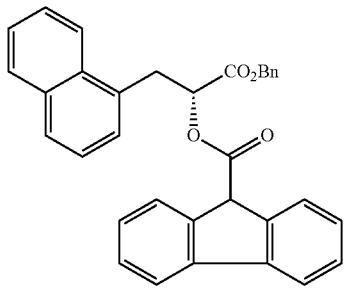

(Example 2-66) Synthesis of H-441

To a solution of H-420 (101 mg, 0.203 mmol) in THF (5 mL), 5% Pd/C (100 mg) was added, and the resulting mixture was stirred under hydrogen atmosphere at room temperature for 16 hours. The reaction mixture was filtered using Celite, and the residue was washed with ethyl acetate, followed by concentration of the solution under reduced pressure. The resulting residue was purified by silica gel column chromatography (chloroform:methanol, 9:1), to obtain H-441 as a yellow oily substance (81 mg, 0.199 mmol, 98%).

Regarding H-441, the NMR measurement spectrum and the result of mass spectrometry by HR-ESI-MS were as follows.
$^1$H NMR (400 MHz, CDCl$_3$) δ3.51 (1H, dd, J=14.2, 10.1 Hz), 3.81 (1H, dd, J=14.2, 3.2 Hz), 4.81 (1H, s), 5.44 (1H, dd, J=10.1, 3.2 Hz), 7.10-7.18 (2H, m), 7.22-7.43 (5H, m), 7.46-7.53 (3H, m), 7.68-7.73 (2H, m), 7.79 (1H, d, J=8.2 Hz), 7.85-7.90 (1H, m), 8.03-8.10 (1H, m); HRESIMS calcd for C$_{27}$H$_{20}$O$_4$Na [M+Na]$^+$ 431.1259, found 431.1255.

The chemical structure of H-441 found was as follows.
(H-441)

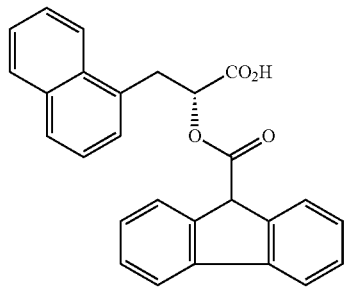 [SMILES: O=C(O[C@H](Cc1cccc2ccccc12)C(=O)O)C1c2ccccc2-c2ccccc21]

(Example 2-67) Synthesis of H-506

To a suspension of tert-butyldimethyl(3-(oxiran-2-yl)propoxy)silane (1.66 g, 7.68 mmol) synthesized by a method described in a document and copper(I) iodide (2.19 g, 11.5 mmol) in THF (50 mL), Grignard reagent generated by heating 2-bromonaphthalene (4.77 g, 23 mmol) and magnesium (560 mg, 23 mmol) to reflux in THF (30 mL) was added dropwise at −20° C., followed by stirring the resulting mixture at the same temperature for 1 hour. Saturated aqueous ammonium chloride solution was added to the mixture, and extraction was carried out with ethyl acetate. The organic layer was washed with saturated brine, and then dried over anhydrous magnesium sulfate, followed by filtration, and concentration under reduced pressure. The resulting residue was purified by silica gel column chromatography (hexane:ethyl acetate, 10:1), to obtain H-469 as a brown oily substance (2.61 g, 7.57 mmol, 52%).

Regarding H-469, the result of NMR measurement spectrum analysis was as follows.
$^1$H NMR (400 MHz, CDCl$_3$) δ0.06 (6H, s), 0.89 (9H, s), 1.49-1.58 (1H, m), 1.62-1.76 (3H, m), 2.88-2.99 (2H, m), 3.62-3.72 (2H, m), 3.90-3.98 (1H, m), 7.37 (1H, dd, J=8.2, 1.4 Hz), 7.40-7.50 (2H, m), 7.67 (1H, s), 7.76-7.83 (3H, m).

The chemical structure of H-469 found was as follows.
(H-469)

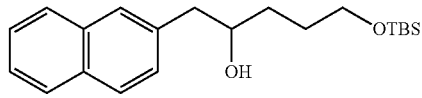 [SMILES: CC(C)(C)[Si](C)(C)OCCCC(O)Cc1ccc2ccccc2c1]

To a solution of H-469 (300 mg, 0.87 mmol), naphthalene-2-carboxylic acid (279 mg, 1.62 mmol), and 4-dimethylaminopyridine (11 mg, 0.087 mmol) in dichloromethane (10 mL), 1-ethyl-3-(3-dimethylaminopropyl)carbodiimide hydrochloride (251 mg, 0.64 mmol) was added at room temperature, and the resulting mixture was heated to reflux for 2 days. The mixture was cooled to room temperature, and water was added thereto, followed by extraction with ethyl acetate. The organic layer was washed with saturated brine, and then dried over anhydrous magnesium sulfate, followed by filtration, and concentration under reduced pressure. The resulting residue was purified by silica gel column chromatography (hexane:ethyl acetate, 10:1), to obtain H-506 as a brown oily substance (257 mg, 0.50 mmol, 57%).

Regarding H-506, the NMR measurement spectrum and the result of mass spectrometry by HR-ESI-MS were as follows.

$^2$H NMR (400 MHz, CDCl$_3$) δ0.00 (6H, s), 0.83 (9H, s), 1.58-1.90 (4H, m), 3.15 (1H, dd, J=13.7, 6.4 Hz), 3.28 (1H, dd, J=13.7, 5.9 Hz), 3.61 (2H, t, J=6.3 Hz), 5.46-5.54 (1H, m), 7.39-7.46 (3H, m), 7.52-7.62 (2H, m), 7.71-7.81 (4H, m), 7.86-7.97 (3H, m), 8.05 (1H, dd, J=8.5, 1.9 Hz), 8.58 (1H, s); HRESIMS calcd for C$_{32}$H$_{39}$O$_3$Si [M+H]$^+$ 499.2668, found 499.2669.

The chemical structure of H-506 found was as follows.
(H-506)

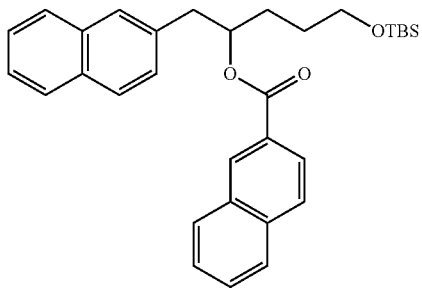 [SMILES: CC(C)(C)[Si](C)(C)OCCCC(Cc1ccc2ccccc2c1)OC(=O)c1ccc2ccccc2c1]

(Example 2-68) Synthesis of H-507

To a solution of H-506 (216 mg, 0.42 mmol) in acetone (2 mL), Jones reagent (2.5 M, 0.67 mL, 1.68 mmol) was added at room temperature, and the resulting mixture was stirred for 2 hours. Isopropanol was added to the mixture to reduce excessive Jones reagent, and 1 M hydrochloric acid was added thereto, followed by extraction with ethyl acetate. The organic layer was washed with saturated brine, and then dried over anhydrous magnesium sulfate, followed by filtration, and concentration under reduced pressure. The resulting residue was purified by silica gel column chromatography (hexane:ethyl acetate, 1:1), to obtain H-507 as a pale yellow powder (48 mg, 0.116 mmol, 28%).

Regarding H-507, the result of NMR measurement spectrum analysis was as follows.

$^1$H NMR (400 MHz, CDCl$_3$) δ2.04-2.12 (2H, m), 2.36-2.51 (2H, m), 3.13 (1H, dd, J=13.7, 6.9 Hz), 3.31 (1H, dd, J=13.7, 5.9 Hz), 5.47-5.55 (1H, m), 7.40-7.47 (3H, m), 7.51-7.60 (2H, m), 7.71 (1H, s), 7.74-7.82 (3H, m), 7.84-7.89 (2H, m), 7.94 (1H, d, J=7.8 Hz), 8.03 (1H, dd, J=8.5, 1.8 Hz), 8.56 (1H, s).

The chemical structure of H-507 found was as follows.
(H-507)

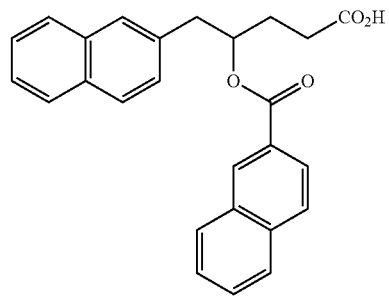 [SMILES: O=C(O)CCC(Cc1ccc2ccccc2c1)OC(=O)c1ccc2ccccc2c1]

(Example 2-69) Synthesis of H-511

To a suspension of tert-butyldimethyl(oxiran-2-ylmethoxy)silane (2.0 g, 10.6 mmol) and copper(I) iodide (506 mg, 2.66 mmol) in THF (50 mL), Grignard reagent generated by heating 2-bromo-6-methoxynaphthalene (7.55 g, 32 mmol) and magnesium (774 mg, 32 mmol) to reflux in THF (40 mL) was added dropwise at −15° C., followed by stirring the resulting mixture at the same temperature for 7 hour. Saturated aqueous ammonium chloride solution was added to the mixture, and extraction was carried out with ethyl acetate. The organic layer was washed with saturated brine, and then dried over anhydrous magnesium sulfate, followed by filtration, and concentration under reduced pressure. The resulting residue was purified by silica gel column chromatography (hexane:ethyl acetate, 10:1 to 5:1), to obtain H-510 as pale yellow crystals (2.33 g, 6.75 mmol, 64%).

Regarding H-510, the NMR measurement spectrum and the result of mass spectrometry by HR-ESI-MS were as follows.

$^1$H NMR (400 MHz, CDCl$_3$) δ0.06 (3H, s), 0.07 (3H, s), 0.92 (9H, s), 2.44 (1H, d, J=3.5 Hz), 2.86-2.96 (2H, m), 3.51 (1H, dd, J=10.0, 6.4 Hz), 3.63 (1H, dd, J=10.0, 4.1 Hz), 3.92 (3H, s), 3.92-4.00 (1H, m), 7.10-7.15 (2H, m), 7.33 (1H, dd, J=8.5, 1.8 Hz), 7.59 (1H, s), 7.66-7.70 (2H, m); HRESIMS calcd for C$_{20}$H$_{30}$O$_3$NaSi [M+Na]$^+$ 369.1862, found 369.1856.

The chemical structure of H-510 found was as follows.
(H-510)

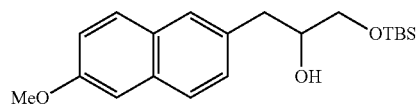 [SMILES: COc1ccc2cc(CC(O)CO[Si](C)(C)C(C)(C)C)ccc2c1]

To a solution of H-510 (500 mg, 1.45 mmol), naphthalene-2-carboxylic acid (498 mg, 2.89 mmol), and 4-dimethylaminopyridine (35 mg, 0.289 mmol) in dichloromethane (15 mL), 1-ethyl-3-(3-dimethylaminopropyl)carbodiimide hydrochloride (555 mg, 2.89 mmol) was added at room temperature, and the resulting mixture was heated to reflux for 1 day. The mixture was cooled to room temperature, and water was added thereto, followed by extraction with ethyl acetate. The organic layer was washed with saturated brine, and then dried over anhydrous magnesium sulfate, followed by filtration, and concentration under reduced pressure. The resulting residue was purified by silica gel column chromatography (hexane:ethyl acetate, 15:1), to obtain H-511 as white crystals (510 mg, 1.02 mmol, 71%).

Regarding H-511, the NMR measurement spectrum and the result of mass spectrometry by HR-ESI-MS were as follows.

$^1$H NMR (400 MHz, CDCl$_3$) δ0.05 (3H, s), 0.06 (3H, s), 0.93 (9H, s), 3.22 (1H, dd, J=13.8, 6.4 Hz), 3.29 (1H, dd, J=13.8, 6.4 Hz), 3.76-3.85 (2H, m), 3.90 (3H, s), 5.41-5.47 (1H, m), 7.09-7.13 (2H, m), 7.43 (1H, dd, J=8.2, 1.8 Hz), 7.51-7.62 (2H, m), 7.64-7.70 (3H, m), 7.85-7.90 (2H, m), 7.93 (1H, d, J=7.8 Hz), 8.05 (1H, dd, J=8.3, 1.4 Hz), 8.58 (1H, s); HRESIMS calcd for C$_{31}$H$_{36}$O$_4$NaSi [M+Na]$^+$ 523.2281, found 523.2280.

The chemical structure of H-511 found was as follows.

(H-511)

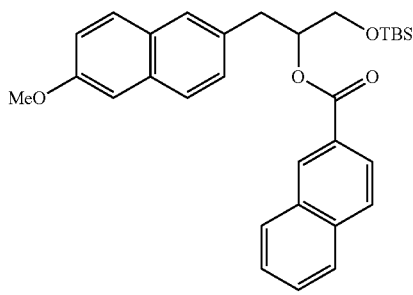 [SMILES: COc1ccc2cc(CC(CO[Si](C)(C)C(C)(C)C)OC(=O)c3ccc4ccccc4c3)ccc2c1]

(Example 2-70) Synthesis of H-512

To a solution of H-511 (490 mg, 0.98 mmol) in acetone (5 mL), Jones reagent (2.5 M, 1.18 mL, 2.94 mmol) was added at room temperature, and the resulting mixture was stirred for 13 hours. Isopropanol was added to the mixture to reduce excessive Jones reagent, and 1 M hydrochloric acid was added thereto, followed by extraction with ethyl acetate. The organic layer was washed with saturated brine, and then dried over anhydrous magnesium sulfate, followed by filtration, and concentration under reduced pressure. The resulting residue was purified by silica gel column chromatography (hexane:ethyl acetate, 1:1 to ethyl acetate), to obtain H-512 as a brown powder (48 mg, 0.12 mmol, 12%).

Regarding H-512, the NMR measurement spectrum and the result of mass spectrometry by HR-ESI-MS were as follows.

$^1$H NMR (400 MHz, CDCl$_3$) δ3.45-3.56 (2H, m), 3.90 (3H, s), 5.63 (1H, dd, J=8.2, 4.5 Hz), 7.09-7.15 (2H, m), 7.46 (1H, dd, J=8.2, 1.8 Hz), 7.51-7.62 (2H, m), 7.68-7.73 (2H, m), 7.75 (1H, s), 7.83-7.93 (3H, m), 8.02 (1H, dd, J=8.2, 1.1 Hz), 8.57 (1H, s); HRESIMS calcd for C$_{25}$H$_{19}$O$_5$ [M−H]$^+$ 399.1232, found 399.1232.

The chemical structure of H-512 found was as follows.

(H-512)

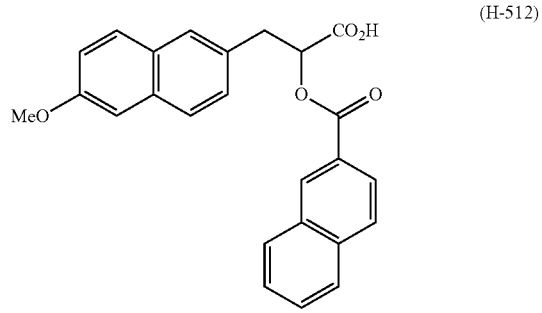 [SMILES: COc1ccc2cc(CC(OC(=O)c3ccc4ccccc4c3)C(=O)O)ccc2c1]

(Example 2-71) Synthesis of H-513

To a suspension of tert-butyldimethyl(2-(oxiran-2-yl)ethoxy)silane (1.40 g, 6.93 mmol) synthesized by a method described in a document and copper(I) iodide (330 mg, 1.73 mmol) in THF (15 mL), Grignard reagent generated by heating 2-bromonaphthalene (4.30 g, 20.8 mmol) and magnesium (657 mg, 27 mmol) to reflux in THF (40 mL) was added dropwise at −15° C., followed by stirring the resulting mixture at the same temperature for 5 hour. Saturated aqueous ammonium chloride solution was added to the mixture, and extraction was carried out with ethyl acetate. The organic layer was washed with saturated brine, and then dried over anhydrous magnesium sulfate, followed by filtration, and concentration under reduced pressure. The resulting residue was purified by silica gel column chromatography (hexane:ethyl acetate, 6:1), to obtain H-457 as a yellow oily substance (1.20 g, 3.64 mmol, 53%).

Regarding H-457, the result of NMR measurement spectrum analysis was as follows.

$^1$H NMR (400 MHz, CDCl$_3$) δ0.10 (6H, s), 0.93 (9H, s), 1.70-1.78 (2H, m), 2.92 (1H, dd, J=13.7, 6.4 Hz), 3.04 (1H, dd, J=13.7, 6.8 Hz), 3.77-3.84 (1H, m), 3.88-3.94 (1H, m), 4.16-4.23 (1H, m), 7.40 (1H, dd, J=8.2, 1.8 Hz), 7.42-7.53 (3H, m), 7.69 (1H, s), 7.79-7.89 (2H, m).

The chemical structure of H-457 found was as follows.

(H-457)

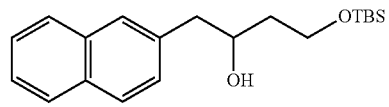 [SMILES: CC(C)(C)[Si](C)(C)OCCC(O)Cc1ccc2ccccc2c1]

To a solution of H-457 (300 mg, 0.91 mmol), naphthalene-2-carboxylic acid (172 mg, 1.0 mmol), and 4-dimethylaminopyridine (11 mg, 0.09 mmol) in dichloromethane (6 mL), 1-ethyl-3-(3-dimethylaminopropyl)carbodiimide hydrochloride (261 mg, 1.36 mmol) was added at room temperature, and the resulting mixture was heated to reflux for 2 days. The mixture was cooled to room temperature, and water was added thereto, followed by extraction with ethyl acetate. The organic layer was washed with saturated brine, and then dried over anhydrous magnesium sulfate, followed by filtration, and concentration under reduced pressure. The resulting residue was purified by silica gel column chromatography (hexane:ethyl acetate, 15:1), to obtain H-513 as a yellow oily substance (537 mg, 1.11 mmol, 82%).

Regarding H-513, the result of NMR measurement spectrum analysis was as follows.

¹H NMR (400 MHz, CDCl₃) δ−0.02 (3H, s), −0.01 (3H, s), 0.85 (9H, s), 1.95-2.02 (2H, m), 3.21 (1H, dd, J=13.7, 6.8 Hz), 3.30 (1H, dd, J=13.7, 5.4 Hz), 3.70-3.80 (2H, m), 5.56-5.64 (1H, m), 7.39-7.46 (3H, m), 7.52-7.62 (2H, m), 7.72 (1H, s), 7.72-7.82 (3H, m), 7.86-7.90 (2H, m), 7.94 (1H, d, J=7.3 Hz), 8.04 (1H, dd, J=8.7, 1.8 Hz), 8.57 (1H, s).

The chemical structure of H-513 found was as follows.
(H-513)

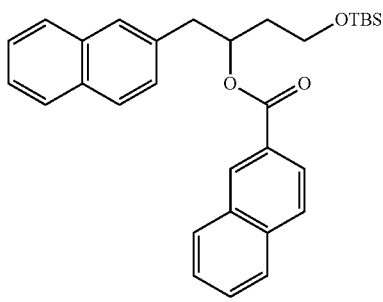 [SMILES: CC(C)(C)[Si](C)(C)OCCC(Cc1ccc2ccccc2c1)OC(=O)c1ccc2ccccc2c1]

(Example 2-72) Synthesis of H-514

To a solution of H-513 (450 mg, 0.93 mmol) in acetone (5 mL), Jones reagent (2.5 M, 1.12 mL, 2.79 mmol) was added at room temperature, and the resulting mixture was stirred for 13 hours. Isopropanol was added to the mixture to reduce excessive Jones reagent, and 1 M hydrochloric acid was added thereto, followed by extraction with ethyl acetate. The organic layer was washed with saturated brine, and then dried over anhydrous magnesium sulfate, followed by filtration, and concentration under reduced pressure. The resulting residue was purified by silica gel column chromatography (hexane:ethyl acetate, 1:1 to ethyl acetate), to obtain H-514 as a white powder (215 mg, 0.56 mmol, 60%).

Regarding H-514, the NMR measurement spectrum and the result of mass spectrometry by HR-ESI-MS were as follows.

¹H NMR (400 MHz, CDCl₃) δ2.76 (1H, dd, J=16.0, 5.1 Hz), 2.85 (1H, dd, J=16.0, 7.8 Hz), 3.24 (1H, dd, J=13.7, 6.8 Hz), 3.38 (1H, dd, J=13.7, 5.9 Hz), 5.78-5.85 (1H, m), 7.41-7.48 (3H, m), 7.51-7.62 (2H, m), 7.74 (1H, s), 7.75-7.83 (3H, m), 7.84-7.89 (2H, m), 7.93 (1H, d, J=8.3 Hz), 8.02 (1H, dd, J=8.3, 1.8 Hz), 8.56 (1H, s); HRESIMS calcd for C₂₅H₁₉O₄ [M−H]⁺ 383.1283, found 383.1282.

The chemical structure of H-514 found was as follows.
(H-514)

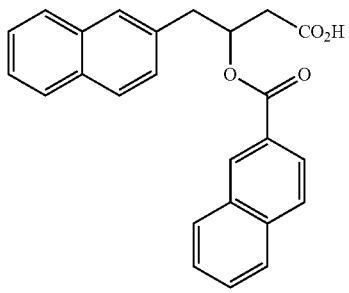 [SMILES: O=C(O)CC(Cc1ccc2ccccc2c1)OC(=O)c1ccc2ccccc2c1]

(Example 2-73) Synthesis of H-515

To a solution of 2-(but-3-en-1-yl)naphthalene (1.32 g, 7.25 mmol) in acetone (40 mL) and water (10 mL), an aqueous osmium tetroxide solution (4%, 0.76 mL, 0.12 mmol) and N-methylmorpholine oxide (1.0 g, 8.7 mmol) were added at room temperature, and the resulting mixture was stirred for 16 hours. Aqueous 5% Na₂SO₃ solution was added to the mixture, and extraction was carried out with ethyl acetate. The organic layer was washed with saturated brine, and then dried over anhydrous magnesium sulfate, followed by filtration, and concentration under reduced pressure. The resulting residue was purified by silica gel column chromatography (hexane:ethyl acetate, 1:1), to obtain H-433 as a pale yellow oily substance (1.34 g, 6.2 mmol, 86%).

Regarding H-433, the result of NMR measurement spectrum analysis was as follows.

¹H NMR (400 MHz, CDCl₃) δ1.80-1.92 (2H, m), 2.87 (1H, dt, J=13.7, 8.2 Hz), 2.98 (1H, ddd, J=13.7, 8.7, 6.4 Hz), 3.50 (1H, dd, J=11.0, 7.8 Hz), 3.66-3.81 (3H, m), 7.35 (1H, dd, J=8.7, 1.8 Hz), 7.38-7.48 (2H, m), 7.65 (1H, s), 7.72-7.83 (3H, m).

The chemical structure of H-433 found was as follows.
(H-433)

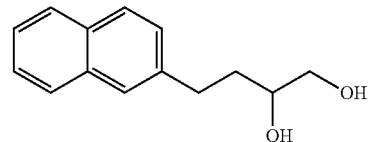 [SMILES: OCC(O)CCc1ccc2ccccc2c1]

To a solution of H-433 (400 mg, 1.85 mmol) in DMF (5 mL), imidazole (280 mg, 4.1 mmol) and TBSCl (307 mg, 2.04 mmol) were added at room temperature, and the resulting mixture was stirred at the same temperature for 15 hours. Water was added to the mixture, and extraction was carried out with ethyl acetate. The organic layer was washed with saturated brine, and then dried over anhydrous magnesium sulfate, followed by filtration, and concentration under reduced pressure. The resulting residue was purified by silica gel column chromatography (hexane:ethyl acetate, 3:1), to obtain H-460 as a pale yellow oily substance (606 mg, 1.84 mmol, 99%).

Regarding H-460, the NMR measurement spectrum and the result of mass spectrometry by HR-ESI-MS were as follows.

¹H NMR (400 MHz, CDCl₃) δ0.06 (3H, m), 0.07 (3H, m), 0.90 (9H, s), 1.75-1.92 (2H, m), 2.49 (1H, d, J=3.6 Hz), 2.86 (1H, ddd, J=13.7, 9.1, 7.3 Hz), 2.99 (1H, ddd, J=13.7, 9.6, 5.9 Hz), 3.44 (1H, dd, J=9.6, 7.3 Hz), 3.64 (1H, dd, J=9.6, 3.2 Hz), 3.66-3.74 (1H, m), 7.36 (1H, dd, J=8.7, 1.8 Hz), 7.39-7.48 (2H, m), 7.65 (1H, s), 7.75-7.82 (3H, m); HRESIMS calcd for C₂₀H₃₁O₂Si [M+H]⁺ 331.2093, found 331.2085.

The chemical structure of H-460 found was as follows.
(H-460)

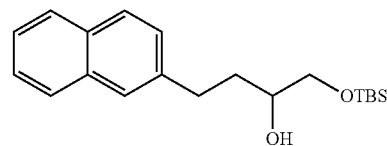 [SMILES: CC(C)(C)[Si](C)(C)OCC(O)CCc1ccc2ccccc2c1]

To a solution of H-460 (550 mg, 1.67 mmol), naphthalene-2-carboxylic acid (575 mg, 3.34 mmol), and 4-dimethylaminopyridine (40 mg, 0.33 mmol) in dichloromethane (10 mL), 1-ethyl-3-(3-dimethylaminopropyl)carbodiimide hydrochloride (640 mg, 3.34 mmol) was added at room temperature, and the resulting mixture was heated to reflux for 15 hours. The mixture was cooled to room temperature, and water was added thereto, followed by extraction with ethyl acetate. The organic layer was washed with saturated brine, and then dried over anhydrous magnesium sulfate, followed by filtration, and concentration under reduced pressure. The resulting residue was purified by silica gel column chromatography (hexane:ethyl acetate, 10:1), to obtain H-515 as a pale yellow oily substance (605 mg, 1.25 mmol, 75%).

Regarding H-515, the NMR measurement spectrum and the result of mass spectrometry by HR-ESI-MS were as follows.

$^1$H NMR (400 MHz, CDCl$_3$) δ0.04 (3H, m), 0.05 (3H, m), 0.88 (9H, s), 2.20-2.28 (2H, m), 2.88-3.02 (2H, m), 3.85 (1H, dd, J=11.0, 4.6 Hz), 3.89 (1H, dd, J=11.0, 5.0 Hz), 5.27-5.33 (1H, m), 7.33-7.45 (3H, m), 7.51-7.62 (2H, m), 7.64 (1H, s), 7.72-7.78 (3H, m), 7.84-7.94 (3H, m), 8.05 (1H, d, J=8.7 Hz), 8.57 (1H, s); HRESIMS calcd for C$_{31}$H$_{37}$O$_3$Si [M+H]$^+$ 485.2512, found 485.2509.

The chemical structure of H-515 found was as follows.
(H-515)

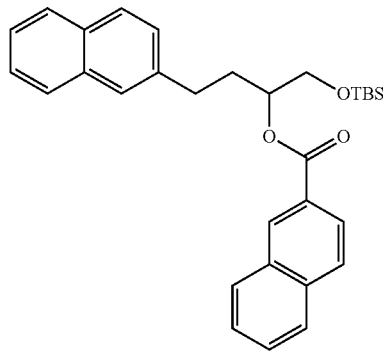 [SMILES: CC(C)(C)[Si](C)(C)OCC(CCc1ccc2ccccc2c1)OC(=O)c1ccc2ccccc2c1]

(Example 2-74) Synthesis of H-516

To a solution of H-515 (100 mg, 0.207 mmol) in acetone (3 mL), Jones reagent (2.5 M, 0.25 mL, 0.62 mmol) was added at room temperature, and the resulting mixture was stirred for 5 hours. Isopropanol was added to the mixture to reduce excessive Jones reagent, and 1 M hydrochloric acid was added thereto, followed by extraction with ethyl acetate. The organic layer was washed with saturated brine, and then dried over anhydrous magnesium sulfate, followed by filtration, and concentration under reduced pressure. The resulting residue was purified by silica gel column chromatography (hexane:ethyl acetate, 1:1 to ethyl acetate), to obtain H-516 as a pale yellow powder (9.7 mg, 0.025 mmol, 12%).

Regarding H-516, the NMR measurement spectrum and the result of mass spectrometry by HR-ESI-MS were as follows.

$^1$H NMR (400 MHz, CDCl$_3$) δ2.48-2.55 (2H, m), 3.09 (2H, t, J=8.0 Hz), 5.39 (1H, t, J=6.9 Hz), 7.38 (1H, dd, J=8.7, 1.8 Hz), 7.39-7.47 (2H, m), 7.54 (1H, t, J=7.4 Hz), 7.61 (1H, t, J=8.2 Hz), 7.68 (1H, s), 7.73-7.81 (3H, m), 7.83-7.90 (3H, m), 8.03 (1H, dd, J=8.7, 1.9 Hz), 8.57 (1H, s); HRESIMS calcd for C$_{25}$H$_{19}$O$_4$ [M−H]$^+$ 383.1283, found 383.1287.

The chemical structure of H-516 found was as follows.
(H-516)

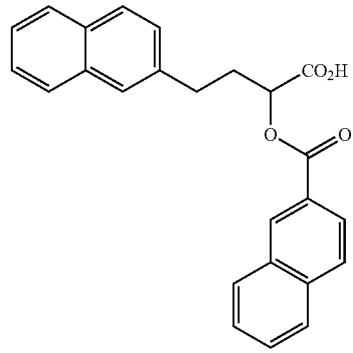 [SMILES: O=C(OC(CCc1ccc2ccccc2c1)C(=O)O)c1ccc2ccccc2c1]

Example 3

(Evaluation of Inhibitory Activity on Function of Pin1)

In order to evaluate the inhibitory activities of the compounds of the present invention synthesized in Example 2 on the function of Pin1, an assay using cells was carried out according to a method previously developed by the present inventors (Yusuke Nakatsu et al., Journal of Biological Chemistry, 2015, Vol. 290, No. 40, pp. 24255-24266), using as an index the degree of phosphorylation of AMPK (AMP-activated protein kinase), whose phosphorylation is known to be suppressed by Pin1.

Briefly, 293T cells were plated on a 24-well plate coated with collagen. Forty-eight hours later, each compound (100 μM) synthesized in the Example was added to the plate, and the plate was left to stand in an incubator for 30 minutes. Thereafter, 10 mM 2-DG was added to the plate, and, 1 hour later, each sample was collected using a buffer containing mercaptoethanol and SDS.

According to conventional methods, SDS-PAGE and blotting were carried out, and then blocking was carried out with 3% BSA for 1 hour. Thereafter, reaction was carried out at normal temperature for 1 hour with each of a pAMPK antibody (Cell signaling 1:2000, Can get signal solution 1: diluted by Toyobo) as a primary antibody, and an HRP-linked anti rabbit IgG (GE healthcare 1:4000, Can get signal solution 2: diluted by Toyobo) as a secondary antibody, to perform detection.

As a compound to be compared, C1: (R)-2-(5-(4-methoxyphenyl)-2-methylfuran-3-carboxamido)-3-(naphthalene-6-yl)propanoic acid, which is an already reported Pin1 inhibitor, was used.

Figure 3:
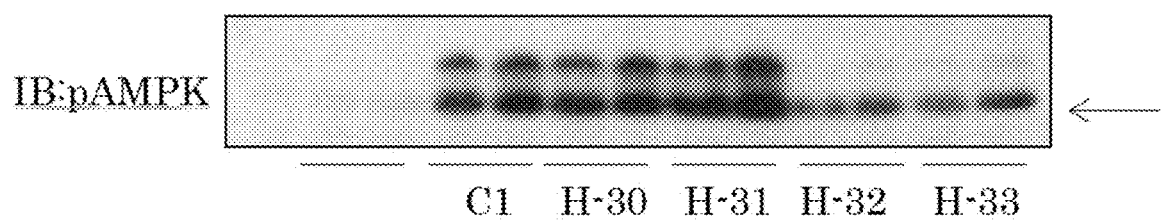
FIG. 3 shows a photograph presented instead of a drawing showing an example of immunostaining for detection of phosphorylation of AMPK. "-" indicates the degree of phosphorylation of AMPK in a case where no Pin1 inhibitor was added, and "C1", "H-30", "H-31", "H-32", and "H-33" indicate the degrees of phosphorylation of AMPK in cases where the respective Pin1 inhibitors were added.

As examples of the results of the immunostaining, FIG. 3 shows the results of detection of phosphorylation of AMPK in cases where H-30 (Example 2-5), H-31 (Example 2-7), H-32 (Example 2-10), or H-33 (Example 2-12) was added. In FIG. 3, "−" indicates the degree of phosphorylation of AMPK in a case where no Pin1 inhibitor was added, and "C1", "H-30", "H-31", "H-32", and "H-33" indicate the degrees of phosphorylation of AMPK in cases where the respective Pin1 inhibitors were added. The immunostaining results show that, as the degree of phosphorylation of AMPK increases, the function of Pin1 is more strongly inhibited. The inhibitory activity on the function of Pin1 was rated as follows based on comparison with the degree of inhibition by C1.

(−): Promotion of AMPK phosphorylation was not (or hardly) found.
(+): Phosphorylation of AMPK was promoted, but the promotion was weaker than that by C1.
(++): Phosphorylation of AMPK was promoted to the same degree as in the case of C1.
(+++): Phosphorylation of AMPK was promoted more strongly than in the case of C1.

The results were as follows.
(−): H-21 (Example 2-4)
(+): H-32 (Example 2-10), H-33 (Example 2-12), H-132 (Example 2-20), H-149 (Example 2-24), H-198 (Example 2-40), H-200 (Example 2-42), H-210 (Example 2-44), H-212 (Example 2-46), H-248 (Example 2-48), H-265 (Example 2-50), H-266 (Example 2-52), H-269 (Example 2-54), H-270 (Example 2-56)
(++): H-23 (Example 2-3), H-30 (Example 2-5), H-106 (Example 2-14), H-123 (Example 2-16), H-130 (Example 2-18), H-134 (Example 2-22), H-151 (Example 2-26), H-157 (Example 2-28), H-176 (Example 2-32), H-177 (Example 2-34), H-180 (Example 2-38)
(+++): H-31 (Example 2-7), H-141 (Example 2-8), H-175 (Example 2-30), H-179 (Example 2-36)

The result for H-21 indicates that it has no inhibitory activity on Pin1 in a cell-based experiment, and it is therefore thought that a carboxyl group is required for having an inhibitory activity on Pin1. However, H-21 is an ester compound in which a benzyl group is bound to the carboxyl group of H-30, and therefore a carboxyl group can be formed by hydrolysis after administration into the body, resulting in conversion into an active compound.

The activities of H-13, H-22, H-28, H-29, H-92, H-112, H-117, H-118, H-119, H-137, H-139, H-147, H-148, H-167, H-168, H-169, H-170, H-191, H-192, H-193, H-199, H-230, H-235, H-236, H-259, and H-260 were not measured, but, since these are ester compounds in which a benzyl group is bound to the carboxyl group of H-23, H-31, H-32, H-33, H-106, H-123, H-130, H-132, H-134, H-149, H-151, H-157, H-175, H-176, H-177, H-179, H-180, H-198, H-200, H-210, H-212, H-248, H-265, H-266, H-269, and H-270, respectively, a carboxyl group can be formed by hydrolysis after administration into the body, resulting in conversion into active compounds.

H-31 is an R-compound, and H-141 is an S-compound. Since both have inhibitory activities on Pin1, it became clear that both the R-compound and the S-compound have activities.

The results can be summarized as shown in the following tables.

TABLE 1

| Example No. | Compound No. | Structural Formula | Pin1 inhibitory activity |
|---|---|---|---|
| Example 2-2 | H-13 | [structure with CO$_2$Bn] | Not measured (Hydrolysis causes conversion to H-23, which is active.) |

TABLE 1-continued

| Example No. | Compound No. | Structural Formula | Pin1 inhibitory activity |
|---|---|---|---|
| Example 2-3 | H-23 | [structure with CO$_2$H] | ++ |
| Example 2-4 | H-21 | [structure with CO$_2$Bn] | − |
| Example 2-5 | H-30 | [structure with CO$_2$H] | ++ |

TABLE 2

| Example No. | Compound No. | Structural Formula | Pin1 inhibitory activity |
|---|---|---|---|
| Example 2-6 | H-22 | [structure with CO$_2$Bn] | Not measured (Hydrolysis causes conversion to H-31, which is active.) |

TABLE 2-continued

| Example No. | Compound No. | Structural Formula | Pin1 inhibitory activity |
|---|---|---|---|
| Example 2-7 | H-31 | | +++ |
| Example 2-8 | H-141 | | +++ |
| Example 2-9 | H-28 | | Not measured (Hydrolysis causes conversion to H-32, which is active.) |
| Example 2-10 | H-32 | | + |

TABLE 3

| Example No. | Compound No. | Structural Formula | Pin1 inhibitory activity |
|---|---|---|---|
| Example 2-11 | H-29 | | Not measured (Hydrolysis causes conversion to H-33, which is active.) |
| Example 2-12 | H-33 | | + |
| Example 2-13 | H-92 | | Not measured (Hydrolysis causes conversion to H-106, which is active.) |
| Example 2-14 | H-106 | | ++ |

TABLE 4

| Example No. | Compound No. | Structural Formula | Pin1 inhibitory activity |
|---|---|---|---|
| Example 2-15 | H-112 | | Not measured (Hydrolysis causes conversion to H-123, which is active.) |
| Example 2-16 | H-123 | | ++ |
| Example 2-17 | H-117 | | Not measured (Hydrolysis causes conversion to H-130, which is active.) |
| Example 2-18 | H-130 | | ++ |

TABLE 5

| Example No. | Compound No. | Structural Formula | Pin1 inhibitory activity |
|---|---|---|---|
| Example 2-19 | H-118 | | Not measured (Hydrolysis causes conversion to H-132, which is active.) |
| Example 2-20 | H-132 | | + |
| Example 2-21 | H-119 | | Not measured (Hydrolysis causes conversion to H-134, which is active.) |
| Example 2-22 | H-134 | | ++ |
| Example 2-23 | H-137 | | Not measured (Hydrolysis causes conversion to H-149, which is active.) |
| Example 2-24 | H-149 | | + |

TABLE 6

| Example No. | Compound No. | Structural Formula | Pin1 inhibitory activity |
|---|---|---|---|
| Example 2-25 | H-139 | | Not measured (Hydrolysis causes conversion to H-151, which is active.) |
| Example 2-26 | H-151 | | ++ |
| Example 2-27 | H-147 | | Not measured (Hydrolysis causes conversion to H-157, which is active.) |
| Example 2-28 | H-157 | | ++ |
| Example 2-29 | H-148 | | Not measured (Hydrolysis causes conversion to H-175, which is active.) |
| Example 2-30 | H-175 | | +++ |

TABLE 7

| Example No. | Compound No. | Structural Formula | Pin1 inhibitory activity |
|---|---|---|---|
| Example 2-31 | H-167 | | Not measured (Hydrolysis causes conversion to H-176, which is active.) |
| Example 2-32 | H-176 | | ++ |
| Example 2-33 | H-168 | | Not measured (Hydrolysis causes conversion to H-177, which is active.) |
| Example 2-34 | H-177 | | ++ |

TABLE 8

| Example No. | Compound No. | Structural Formula | Pin1 inhibitory activity |
|---|---|---|---|
| Example 2-35 | H-169 | (structure) | Not measured (Hydrolysis causes conversion to H-179, which is active.) |
| Example 2-36 | H-179 | (structure) | +++ |
| Example 2-37 | H-170 | (structure) | Not measured (Hydrolysis causes conversion to H-180, which is active.) |
| Example 2-38 | H-180 | (structure) | ++ |

TABLE 9

| Example No. | Compound No. | Structural Formula | Pin1 inhibitory activity |
|---|---|---|---|
| Example 2-39 | H-191 | (structure) | Not measured (Hydrolysis causes conversion to H-198, which is active.) |
| Example 2-40 | H-198 | (structure) | + |
| Example 2-41 | H-192 | (structure) | Not measured (Hydrolysis causes conversion to H-200, which is active.) |
| Example 2-42 | H-200 | (structure) | + |
| Example 2-43 | H-193 | (structure) | Not measured (Hydrolysis causes conversion to H-210, which is active.) |
| Example 2-44 | H-210 | (structure) | + |

TABLE 10

| Example No. | Compound No. | Structural Formula | Pin1 inhibitory activity |
|---|---|---|---|
| Example 2-45 | H-199 | (structure) | Not measured (Hydrolysis causes conversion to H-212, which is active.) |

TABLE 10-continued

| Example No. | Compound No. | Structural Formula | Pin1 inhibitory activity |
|---|---|---|---|
| Example 2-46 | H-212 | (naphthalen-2-yl)-CH2-C*H(CO2H)-O-C(=O)-(4-NMe2-C6H4) | + |
| Example 2-47 | H-230 | (naphthalen-2-yl)-CH2-C*H(CO2Bn)-O-C(=O)-C*H(NHBoc)-CH2-Ph | Not measured (Hydrolysis causes conversion to H-248, which is active.) |
| Example 2-48 | H-248 | (naphthalen-2-yl)-CH2-C*H(CO2H)-O-C(=O)-C*H(NHBoc)-CH2-Ph | + |

TABLE 11

| Example No. | Compound No. | Structural Formula | Pin1 inhibitory activity |
|---|---|---|---|
| Example 2-49 | H-235 | (naphthalen-2-yl)-CH2-C*H(CO2Bn)-O-C(=O)-(3,4-diMe-C6H3) | Not measured (Hydrolysis causes conversion to H-265, which is active.) |
| Example 2-50 | H-265 | (naphthalen-2-yl)-CH2-C*H(CO2H)-O-C(=O)-(3,4-diMe-C6H3) | + |
| Example 2-51 | H-236 | (naphthalen-2-yl)-CH2-C*H(CO2Bn)-O-C(=O)-(3,4-diMeO-C6H3) | Not measured (Hydrolysis causes conversion to H-266, which is active.) |
| Example 2-52 | H-266 | (naphthalen-2-yl)-CH2-C*H(CO2H)-O-C(=O)-(3,4-diMeO-C6H3) | + |
| Example 2-53 | H-259 | (naphthalen-2-yl)-CH2-C*H(CO2Bn)-O-C(=O)-(3,4-diCl-C6H3) | Not measured (Hydrolysis causes conversion to H-269, which is active.) |
| Example 2-54 | H-269 | (naphthalen-2-yl)-CH2-C*H(CO2H)-O-C(=O)-(3,4-diCl-C6H3) | + |

TABLE 12

| Example No. | Compound No. | Structural Formula | Pin1 inhibitory activity |
|---|---|---|---|
| Example 2-55 | H-260 | | Not measured (Hydrolysis causes conversion to H-270, which is active.) |
| Example 2-56 | H-270 | | + |
| Example 2-57 | H-250 | | Not measured |
| Example 2-58 | H-254 | | Not measured |
| Example 2-59 | H-251 | | Not measured |
| Example 2-60 | H-262 | | Not measured |

TABLE 13

| Example No. | Compound No. | Structural Formula | Pin1 inhibitory activity |
|---|---|---|---|
| Example 2-61 | H-255 | | Not measured |
| Example 2-62 | H-263 | | Not measured |
| Example 2-63 | H-419 | | Not measured |
| Example 2-64 | H-438 | | Not measured |
| Example 2-65 | H-420 | | Not measured |

TABLE 14

| Example No. | Compound No. | Structural Formula | Pin1 inhibitory activity |
|---|---|---|---|
| Example 2-66 | H-441 | (structure: naphthalen-1-ylmethyl, stereocenter with CO₂H and O-C(=O)-fluoren-9-yl ester) | Not measured |
| Example 2-67 | H-506 | (structure: naphthalen-2-ylmethyl-CH(O-C(=O)-naphthalen-2-yl)-CH₂CH₂-OTBS) | Not measured |
| Example 2-68 | H-507 | (structure: naphthalen-2-ylmethyl-CH(O-C(=O)-naphthalen-2-yl)-CH₂CH₂-CO₂H) | Not measured |
| Example 2-69 | H-511 | (structure: 6-MeO-naphthalen-2-ylmethyl-CH(O-C(=O)-naphthalen-2-yl)-CH₂-OTBS) | Not measured |
| Example 2-70 | H-512 | (structure: 6-MeO-naphthalen-2-ylmethyl, stereocenter with CO₂H and O-C(=O)-naphthalen-2-yl ester) | Not measured |

TABLE 15

| Example No. | Compound No. | Structural Formula | Pin1 inhibitory activity |
|---|---|---|---|
| Example 2-71 | H-513 | (naphthalene-CH2-CH(O-C(=O)-2-naphthyl)-CH2-OTBS) | Not measured |
| Example 2-72 | H-514 | (naphthalene-CH2-CH(O-C(=O)-2-naphthyl)-CH2-CO2H) | Not measured |
| Example 2-73 | H-515 | (naphthalene-CH2-CH2-CH(OTBS)-O-C(=O)-2-naphthyl) | Not measured |
| Example 2-74 | H-516 | (naphthalene-CH2-CH2-CH(CO2H)-O-C(=O)-2-naphthyl) | Not measured |

Example 4

(Therapeutic Experiment Using Model Animals of Ulcerative Colitis)

To C57BL6 mice of 8 weeks old, 3% DSS (dextran sulfate sodium)-containing water or water (control) was administered by allowing the mice to drink it for 7 days. For the mice to which DSS was administered, groups in which 5-ASA (compound name: 5-aminosalicylic acid; generic name: Mesalazine), which is a therapeutic agent for inflammatory bowel diseases, the compound synthesized in Example 2-7 (H-31), or the compound synthesized in Example 2-36 (H-179) was administered, and a group in which no compound was administered were provided. On Day 7 after the beginning of the administration, the body weight of each mouse was measured, and the large intestine was removed from the mouse, followed by carrying out histological study.

Figure 4:
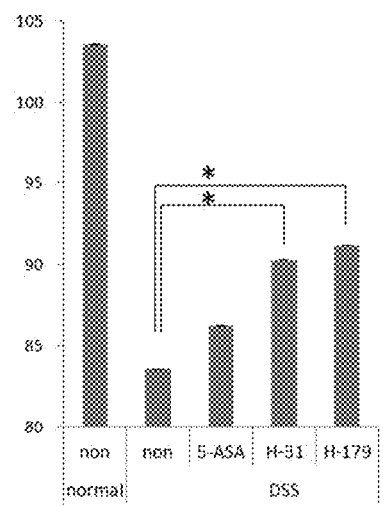
FIG. 4 shows a graph and photographs presented instead of drawings, showing results of body weight measurement and results of histological study of mice in a therapeutic experiment using model animals of ulcerative colitis.
Figure 4:
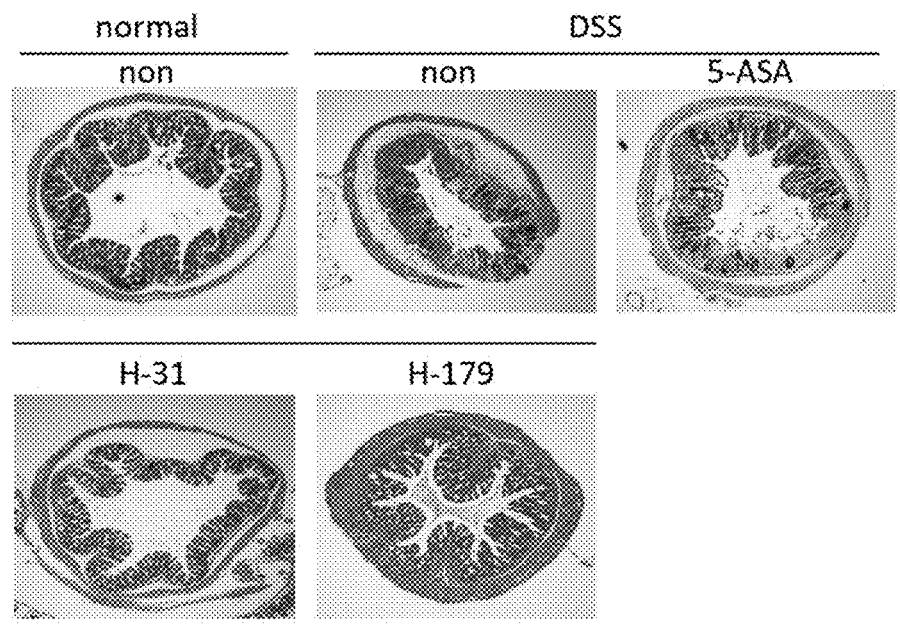

The results of the body weight measurement and the histological study are shown in FIG. 4. FIG. 4(A) shows a graph showing the result of the body weight measurement of each mouse in terms of the ratio (percentage) to the body weight before the beginning of the administration. FIG. 4(B) shows photographs showing the result of staining of a section of the large intestine of each mouse. In FIGS. 4(A) and (B), "normal" indicates a case where water was administered, and "DSS" indicates cases where DSS-containing water was administered. "non" indicates a case where no compound was administered, and "5-ASA", "H-31", and "H-179" indicate cases where the respective compounds were administered. The dose was as follows: 5-ASA, 300 mg/kg/day; H-31, 1 mg/kg/day; H-179, 1 mg/kg/day. As shown in FIG. 4(A), weight loss due to inflammation of the intestine was found in the cases where DSS was administered. However, in the cases where the compound synthesized in Example 2-7 (H-31) or the compound synthesized in Example 2-36 (H-179) was administered, the weight loss was significantly smaller compared to the case where no compound was administered.

As shown in FIG. 4(B), tissue damage in the large intestine due to DSS was found in the case where no compound was administered and the case where 5-ASA (Mesalazine) was administered. In contrast, tissue damage in the large intestine was hardly found in the cases where the compound synthesized in Example 2-7 (H-31) or the compound synthesized in Example 2-36 (H-179) was administered.

Example 5

(Comparison Between Oral Administration and Intraperitoneal Administration)

Figure 5:
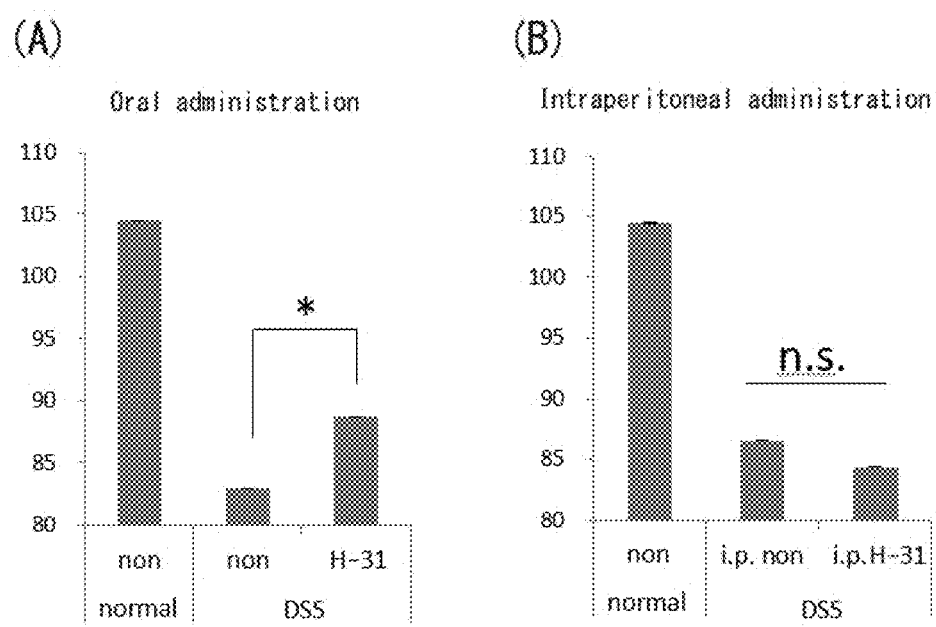
FIG. 5 shows graphs presented instead of drawings, showing results of study on differences in the effect depending on the administration method.

A compound whose therapeutic effect on ulcerative colitis could be confirmed in Example 4 (H-31) was studied on the difference in its effect depending on the administration method. The results are shown in FIG. 5.

FIG. 5(A) shows a graph showing the body weight change in mice subjected to oral administration of H-31 at 1 mg/kg/day. FIG. 5(B) shows a graph showing the body weight change in mice subjected to intraperitoneal administration of H-31 at 1 mg/kg/day. In FIGS. 5(A) and (B), "normal" indicates a case where water was administered, and "DSS" indicates cases where DSS-containing water was administered. "non" indicates a case where no compound was administered, and "H-31" indicates a case where the compound synthesized in Example 2-7 was administered.

As shown in FIG. 5(A), the oral administration of the compound synthesized in Example 2-7 (H-31) resulted in a significant decrease in the body weight change. In contrast, as shown in FIG. 5(B), no significant difference was found in the case of intraperitoneal administration.

Example 6

(Therapeutic Experiment Using Model Animals of Ulcerative Colitis 2)

Figure 6:
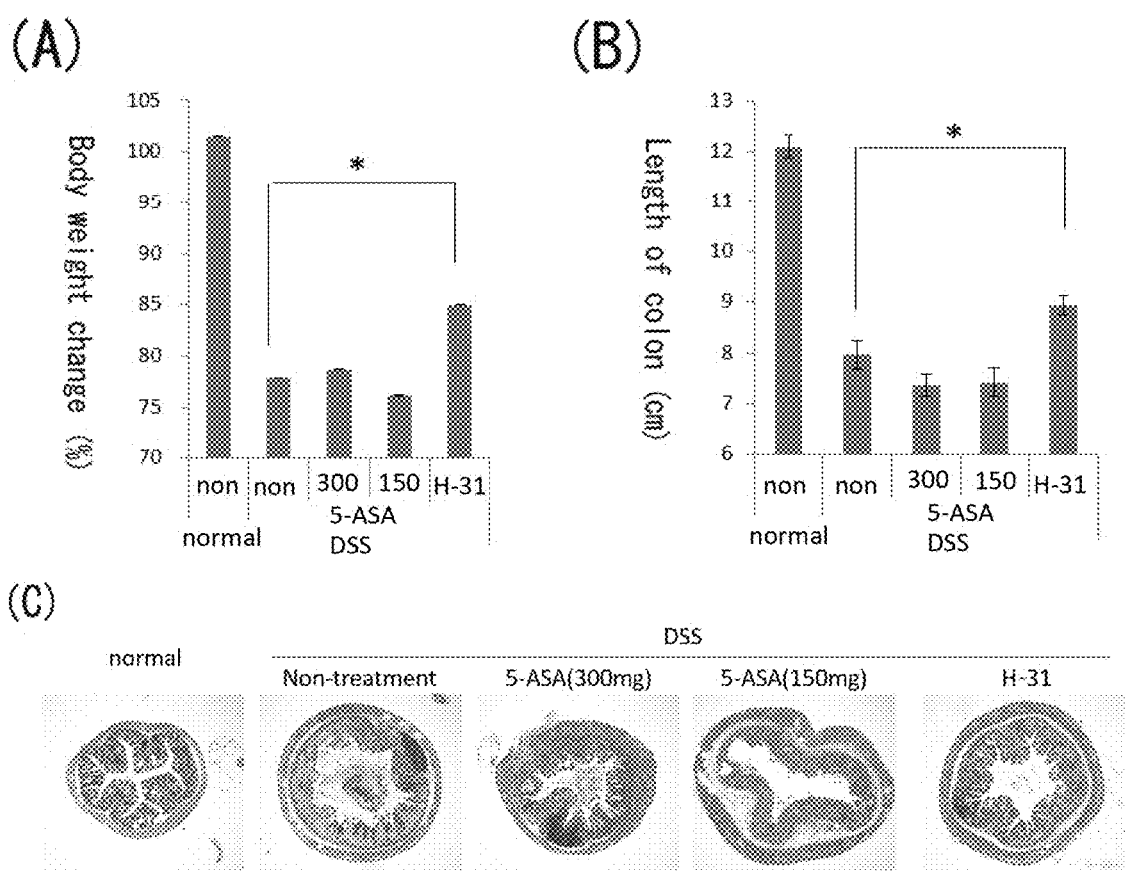
FIG. 6 shows graphs and photographs presented instead of drawings, showing results of a therapeutic experiment that was carried out again using model animals of ulcerative colitis.

A therapeutic experiment using model Animals of ulcerative colitis was carried out again similarly to Example 4. The same experiment as in Example 4 was carried out except that 5-ASA was administered at a dose of 300 mg/kg/day or 150 mg/kg/day, and that the compound synthesized in Example 2-7 (H-31, 1 mg/kg/day) was used as a compound of the present invention. In addition, an experiment for measuring the colon length was carried out. The results are shown in FIG. 6.

As shown in FIG. 6(A), weight loss due to inflammation of the intestine was found in the cases where DSS was administered. However, in the case where the compound synthesized in Example 2-7 (H-31) was administered, the weight loss was significantly smaller compared to the case where no compound was administered. No significant effect was found for 5-ASA. As shown in FIG. 6(B), a decrease in the colon length due to damage of the large intestine was found in the cases where DSS was administered. However, in the case where the compound synthesized in Example 2-7 (H-31) was administered, the change in the colon length was significantly smaller compared to the case where no compound was administered. As shown in FIG. 6(C), tissue damage in the large intestine due to DSS was found in the case where no compound was administered and the cases where 5-ASA (300 mg/kg/day or 150 mg/kg/day) was administered. In contrast, tissue damage in the large intestine was hardly found in the case where the compound synthesized in Example 2-7 (H-31) was administered.

Example 7

(Confirmation of Pin1 Expression Level)

Figure 7:
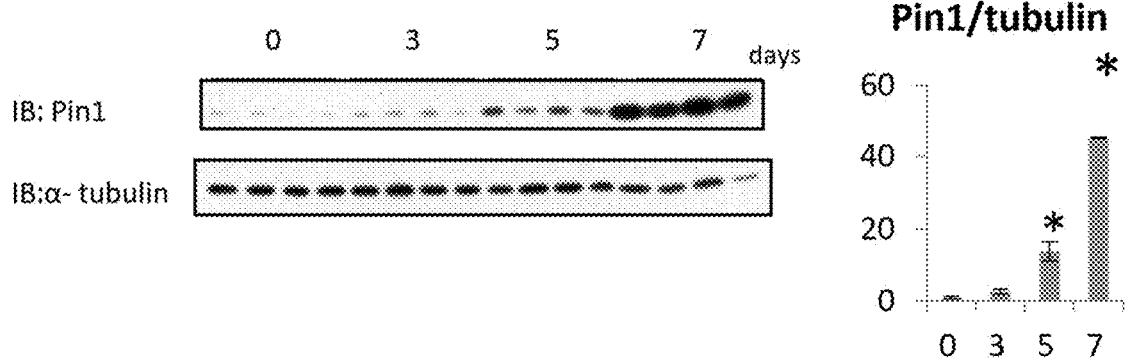
FIG. 7 shows photographs presented instead of drawings, showing results of measurement of the expression level of Pin1 in the intestinal tract of each mouse subjected to a therapeutic experiment.
Figure 7:
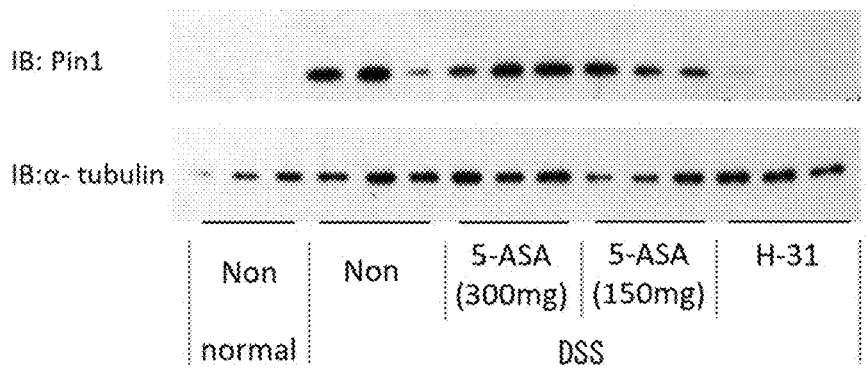

The expression level of Pin1 in the intestinal tract was measured for each mouse subjected to the therapeutic experiment in Example 5. The results are shown in FIG. 7.

FIG. 7(A) shows results of detection of changes in the Pin1 expression level over time in a mouse to which DSS was administered, but to which no compound was administered. As shown in FIG. 7(A), a remarkable increase in the Pin1 protein expression level was found, and the Pin1 protein expression level after 7 days of administration of DSS was 40 to 50 times higher than that in a normal mouse. It was found that cells showing increased Pin1 are infiltrating blood cells and stromal cells. These results suggest involvement of Pin1 in development of ulcerative colitis.

FIG. 7(B) shows results of measurement of the Pin1 protein level in the intestinal tract after 7 days of the administration experiment for each mouse subjected to the therapeutic experiment in Example 5. It was found that the increase in the Pin1 protein level found in the intestinal tract of the mice that developed ulcerative colitis due to the DSS treatment could not be ameliorated with 5-ASA, and that the increase could be significantly ameliorated with the compound synthesized in Example 2-7 (H-31). The present results also support that the compound synthesized in Example 2-7 (H-31) prevents development of ulcerative colitis.

Example 8

(Therapeutic Experiment for NASH)

Example 8-1

In order to test the therapeutic effect of a compound of the present invention on non-alcoholic steatohepatitis (NASH), an animal experiment using NASH model mice was carried out.

The NASH model mice (hereinafter referred to as "NASH mice") were prepared by feeding male individuals of laboratory mice (C57BL/6J) with methionine-choline-deficient diet (MCDD) for 8 weeks to allow accumulation of fat in the liver. The animal experiment was carried out for a group in which a compound of the present invention (H-31) was intraperitoneally administered 3 times a week at 2.5 mg/kg/day during the 8 weeks of the MCDD feeding period, and a group in which no administration was carried out. In addition, in order to provide control mice, male individuals of laboratory mice (C57BL/6J) were fed with normal diet for 8 weeks.

Figure 8:
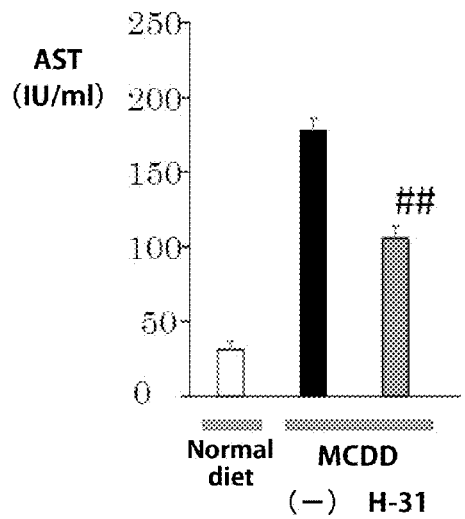
FIG. 8 shows graphs showing results of measurement of the blood AST (GOT) level and the blood ALT (GPT) level in each mouse in a NASH therapeutic experiment.
Figure 8:
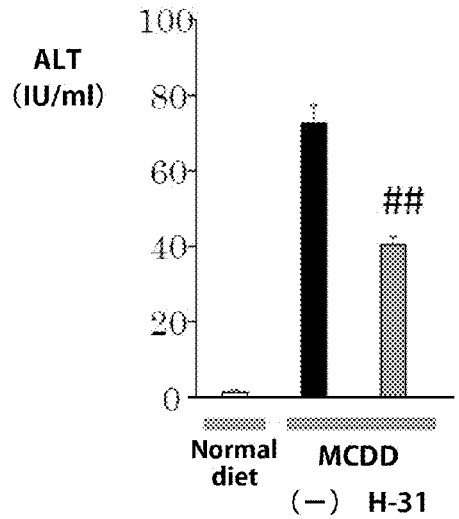

The results of measurement of the blood AST (GOT) level and the blood ALT (GPT) level in these mice are shown in FIGS. 8(A) and (B), respectively.

FIG. 8(A) shows a graph showing the results of measurement of the blood AST (GOT) level (IU/ml), wherein the bars show, from left to right, the measurement results on the blood AST (GOT) levels in the control mice, the NASH mice fed with MCDD, and the NASH mice fed with MCDD to which H-31 was intraperitoneally administered, respectively.

As shown in FIG. 8(A), an increase in the AST value, which indicates inflammation of the liver, was found in the NASH mice to which the Pin1 inhibitor was not administered. In contrast, in the case where the compound of the present invention (H-31) was administered, the AST value decreased, indicating suppression of inflammation of the liver.

FIG. 8(B) shows a graph showing the results of measurement of the blood ALT (GPT) level (IU/ml), wherein the bars show, from left to right, the measurement results on the blood ALT (GPT) levels in the control mice, the NASH mice, and the NASH mice to which H-31 was intraperitoneally administered, respectively.

As shown in FIG. 8(B), an increase in the ALT value, which indicates inflammation of the liver, was found in the NASH mice to which the Pin1 inhibitor was not administered. In contrast, in the case where the compound of the present invention (H-31) was administered, the ALT value decreased, indicating suppression of inflammation of the liver.

Example 8-2

Figure 9:
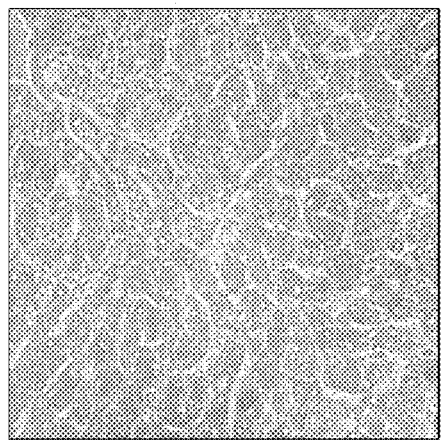
FIG. 9 shows photographs presented instead of drawings, showing results of microscopic observation of the degree of fibrosis, which observation was carried out after Azan staining of sections of liver tissue of mice in a NASH therapeutic experiment.
Figure 9:
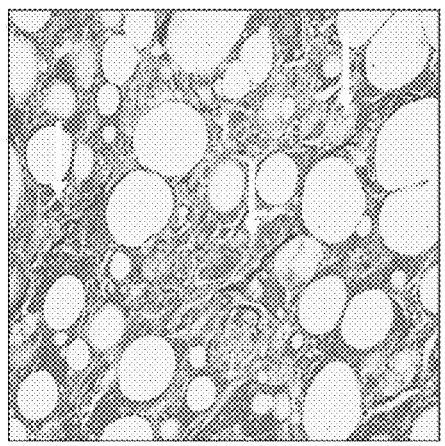
Figure 9:
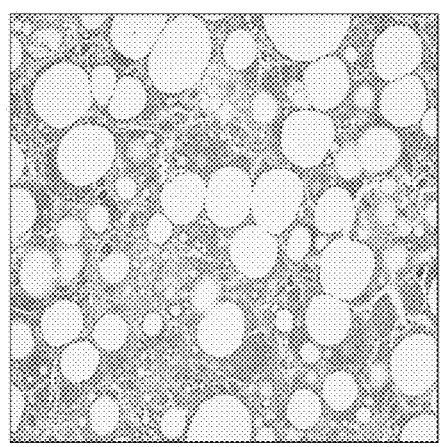

FIG. 9 shows results of microscopic observation of the degree of fibrosis, which observation was carried out after Azan staining of sections of liver tissue of these mice.

FIG. 9(A) shows a photograph showing a result of observation of liver tissue of a control mouse. FIG. 9(B) shows a photograph showing a result of observation of liver tissue of a NASH mouse fed with MCDD. FIG. 9(C) shows a photograph showing a result of observation of liver tissue of a NASH mouse fed with MCDD to which H-31 was intraperitoneally administered.

As shown in FIG. 9(A), the control mice showed no accumulation of fat in liver tissue. In contrast, as shown in FIGS. 9(B) and (C), the NASH mice fed with MCDD showed accumulation of fat in liver tissue. As shown in FIG. 9(B), in the case where H-31 was not administered, fibrosis of liver tissue was found with the Azan staining (the colored area pointed by the arrow). In contrast, as shown in FIG. 9(C), in the case where H-31 was administered, fibrosis of liver tissue was remarkably suppressed.

Example 9

(Therapeutic Experiment for Colon Cancer)

On Day 1, azoxymethane (AOM) was intraperitoneally administered at 12 mg/kg to laboratory mice. Thereafter, from Day 6, a course of 5 days of oral administration of 3% dextran sulfate sodium (DSS) and a period of 16 days without administration of DSS was repeated 4 times to prepare colon cancer model mice having cancer caused by inflammation of the large intestine. A group in which a compound of the present invention (H-31) was administered and a group without administration of the compound of the present invention (control) were provided. In the group in which the compound of the present invention (H-31) was administered, oral administration was carried out 3 times a week at 1.25 mg/kg/day from Day 6.

On Day 89, the colon cancer model mice were dissected, and the number of colon cancer developed and the tumor area per colon cancer (total tumor area/number of tumors) were measured.

Figure 10:
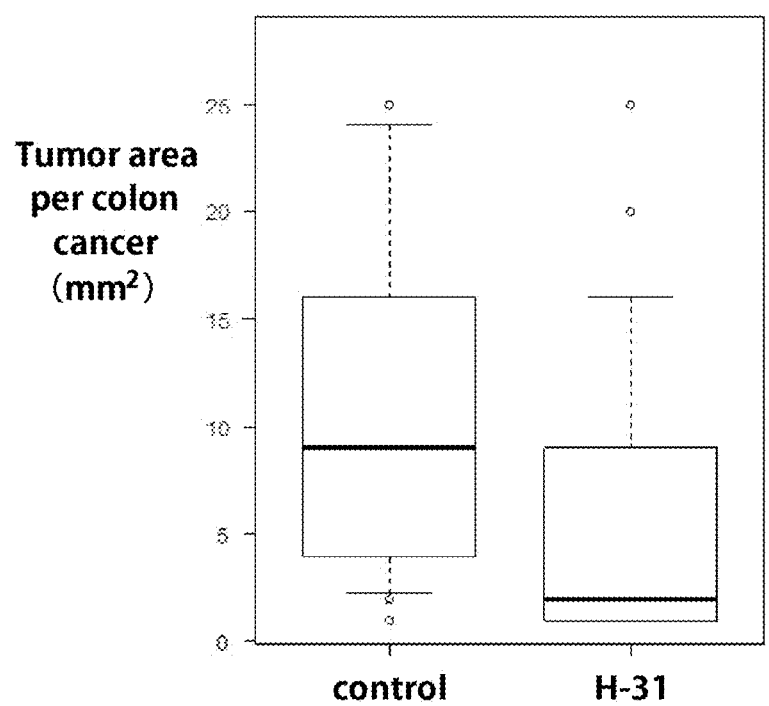
FIG. 10 shows a graph showing results of measurement of the distribution of the tumor area per colon cancer in each individual in a colon cancer therapeutic experiment. The graph shows, from left to right, box plots showing the tumor area distributions in colon cancer model mice to which the compound of the present invention was not administered (control) and colon cancer model mice to which H-31 was administered.

FIG. 10 shows a graph showing the distribution of the tumor area per colon cancer in each individual. The graph shows, from left to right, box plots showing the tumor area distributions in the colon cancer model mice without administration of the compound of the present invention (control) and the colon cancer model mice to which H-31 was administered.

Colon cancer developed in both groups, and there was no significant difference in the number of colon cancer. However, as shown in FIG. 10, reduction of the tumor area could be found in the colon cancer model mice to which H-31 was administered, compared to the control colon cancer model mice. In particular, a large difference in the median was found.

INDUSTRIAL APPLICABILITY

All of the compound or the salt thereof, the Pin1 inhibitor, the pharmaceutical composition, the therapeutic agent or the prophylactic agent for an inflammatory disease, and the therapeutic agent or the prophylactic agent for colon cancer, of the present invention are useful in the pharmaceutical industry.

The invention claimed is:

1. A compound represented by Formula (I):

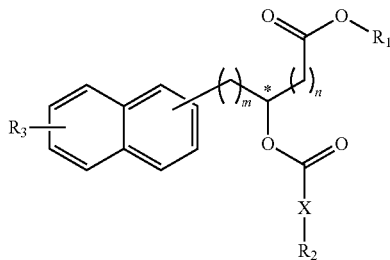
(I)

wherein
- m represents an integer of 1 to 3, and n represents an integer of 0 to 2, with the proviso that 1≤m+n≤3;
- $R_1$ represents a hydrogen atom, a hydrocarbon group optionally having a substituent(s), a heterocyclic group optionally having a substituent(s), or an amino group optionally having a substituent(s);
- $R_2$ represents a polycyclic aryl group optionally having a substituent(s), a heterocyclic group optionally having a substituent(s), an aryloxy group optionally having a substituent(s), a phenyl group having a substituent(s), an aralkyl group having a substituent(s), or a group represented by the following Formula (II):

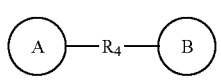
(II)

wherein Ring A and Ring B each represent a monocyclic or polycyclic aryl group or heterocyclic group optionally having a substituent(s); $R_4$ represents a single bond, a $C_{1-3}$ alkylene group optionally having a substituent(s), a $C_{2-3}$ alkenylene group optionally having a substituent(s), or a divalent oxy group; and the Ring A, Ring B, or $R_4$ moiety is linked to X;

- $R_3$ represents 0 to 7 substituent(s) linked to the naphthyl group, each of which substituent(s) is the same or different and has 1 to 10 atoms; and
- X represents:
  (i) a single bond;
  (ii) a $C_{1-6}$ alkylene group optionally having a substituent(s);
  (iii) a $C_{2-6}$ alkenylene group optionally having a substituent(s);
  (iv) an —$R_5$—NH— group or an —NH—$R_5$— group, wherein $R_5$ represents a $C_{1-5}$ alkylene group optionally having a substituent(s), or a $C_{2-5}$ alkenylene group optionally having a substituent(s); or
  (v) a secondary or tertiary amino group;

or a salt thereof.

2. The compound or the salt thereof according to claim 1, wherein the $R_1$ represents a hydrogen atom.

3. The compound or the salt thereof according to claim 1, wherein the $R_2$ represents a polycyclic aryl group optionally having a substituent(s), a polycyclic heterocyclic group optionally having a substituent(s), a polycyclic aryloxy group optionally having a substituent(s), or a group represented by the following Formula (II):

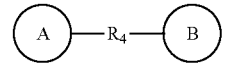
(II)

wherein Ring A and Ring B each represent a monocyclic or polycyclic aryl group optionally having a substituent(s); $R_4$ represents a $C_{1-3}$ alkylene group optionally having a substituent(s), a $C_{2-3}$ alkenylene group optionally having a substituent(s), or a divalent oxy group; and the Ring A, Ring B, or $R_4$ moiety is linked to X.

4. The compound or the salt thereof according to claim 3, wherein the $R_2$ represents a polycyclic aryl group optionally having a substituent(s), a heterocyclic group containing two or more benzene rings and optionally having a substituent(s), or a polycyclic aryloxy group optionally having a substituent(s).

5. The compound or the salt thereof according to claim 1, wherein the configuration at the asymmetric carbon atom indicated by the symbol "*" is the R configuration.

6. A Pin1 inhibitor comprising the compound or the salt thereof according to claim 1.

7. A pharmaceutical composition comprising: the compound according to claim 1 or a pharmaceutically acceptable salt thereof; and a pharmaceutically acceptable carrier.

8. A therapeutic agent for the treatment of an inflammatory disease accompanied by fibrosis, comprising the compound according to claim 1 or a pharmaceutically acceptable salt thereof as an effective component.

9. The therapeutic agent according to claim 8, wherein the inflammatory disease accompanied by fibrosis is an inflammatory bowel disease, non-alcoholic steatohepatitis, or pulmonary fibrosis.

10. The therapeutic agent according to claim 8, wherein the inflammatory disease accompanied by fibrosis is an inflammatory bowel disease.

11. The therapeutic agent according to claim 10, wherein the inflammatory bowel disease is Crohn's disease or ulcerative colitis.

12. A therapeutic agent for the treatment of colon cancer, comprising the compound according to claim 1 or a pharmaceutically acceptable salt thereof as an effective component.

13. A method of treating an inflammatory disease accompanied by fibrosis, comprising administering the compound according to claim 1 to a patient.

14. A method of treating colon cancer, comprising administering the compound according to claim 1 to a patient.

15. A method for treating an inflammatory disease accompanied by fibrosis, wherein said method comprises administering to a subject in need thereof a therapeutic amount of a compound represented by Formula (I) or a pharmaceutically acceptable salt thereof:

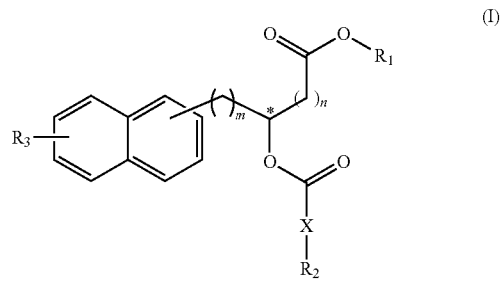
(I)

wherein
- m represents an integer of 0 to 3, and n represents an integer of 0 to 2, with the proviso that 1<m+n<3;
- $R_1$ represents a hydrogen atom, a hydrocarbon group optionally having a substituent(s), a heterocyclic group optionally having a substituent(s), or an amino group optionally having a substituent(s);
- $R_2$ represents a polycyclic aryl group optionally having a substituent(s), a heterocyclic group optionally having a substituent(s), an aryloxy group optionally having a substituent(s), a phenyl group having a substituent(s), an aralkyl group having a substituent(s), or a group represented by the following Formula (II):

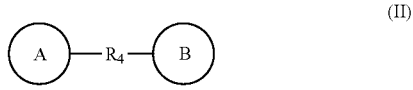

wherein Ring A and Ring B each represent a monocyclic or polycyclic aryl group or heterocyclic group optionally having a substituent(s); $R_4$ represents a single bond, a $C_{1-3}$ alkylene group optionally having a substituent(s), a $C_{2-3}$ alkenylene group optionally having a substituent(s), or a divalent oxy group; and the Ring A, Ring B, or $R_4$ moiety is linked to X;
- $R_3$ represents 0 to 7 substituent(s) linked to the naphthyl group, each of which substituent(s) is the same or different and has 1 to 10 atoms; and
- X represents:
  - (i) a single bond;
  - (ii) a $C_{1-6}$ alkylene group optionally having a substituent(s);
  - (iii) a $C_{2-6}$ alkenylene group optionally having a substituent(s);
  - (iv) an —$R_5$—NH— group or an —NH—$R_5$— group, wherein $R_5$ represents a $C_{1-5}$ alkylene group optionally having a substituent(s), or a $C_{2-5}$ alkenylene group optionally having a substituent(s); or
  - (v) a secondary or tertiary amino group.

16. A method for treating colon cancer, wherein said method comprises administering to a subject in need thereof a therapeutic amount of a compound represented by Formula (I) or a pharmaceutically acceptable salt thereof:

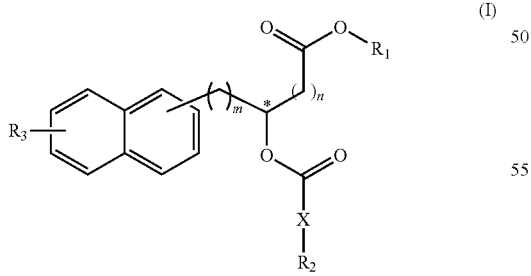

wherein
- m represents an integer of 0 to 3, and n represents an integer of 0 to 2, with the proviso that 1<m+n<3;
- $R_1$ represents a hydrogen atom, a hydrocarbon group optionally having a substituent(s), a heterocyclic group optionally having a substituent(s), or an amino group optionally having a substituent(s);
- $R_2$ represents a polycyclic aryl group optionally having a substituent(s), a heterocyclic group optionally having a substituent(s), an aryloxy group optionally having a substituent(s), a phenyl group having a substituent(s), an aralkyl group having a substituent(s), or a group represented by the following Formula (II):

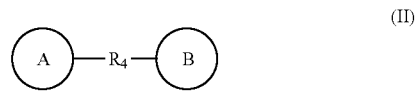

wherein Ring A and Ring B each represent a monocyclic or polycyclic aryl group or heterocyclic group optionally having a substituent(s); $R_4$ represents a single bond, a $C_{1-3}$ alkylene group optionally having a substituent(s), a $C_{2-3}$ alkenylene group optionally having a substituent(s), or a divalent oxy group; and the Ring A, Ring B, or $R_4$ moiety is linked to X;
- $R_3$ represents 0 to 7 substituent(s) linked to the naphthyl group, each of which substituent(s) is the same or different and has 1 to 10 atoms; and
- X represents:
  - (i) a single bond;
  - (ii) a $C_{1-6}$ alkylene group optionally having a substituent(s);
  - (iii) a $C_{2-6}$ alkenylene group optionally having a substituent(s);
  - (iv) an —$R_5$—NH— group or an —NH—$R_5$— group, wherein $R_5$ represents a $C_{1-5}$ alkylene group optionally having a substituent(s), or a $C_{2-5}$ alkenylene group optionally having a substituent(s); or
  - (v) a secondary or tertiary amino group.

17. A method for preparing a pharmaceutical for the treatment of an inflammatory disease accompanied by fibrosis, wherein said method comprises combining a pharmaceutically acceptable carrier and a therapeutic amount of a compound represented by Formula (I) or a pharmaceutically acceptable salt thereof:

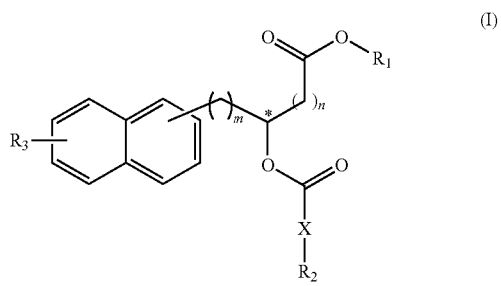

wherein
- m represents an integer of 0 to 3, and n represents an integer of 0 to 2, with the proviso that 1<m+n<3;
- $R_1$ represents a hydrogen atom, a hydrocarbon group optionally having a substituent(s), a heterocyclic group optionally having a substituent(s), or an amino group optionally having a substituent(s);
- $R_2$ represents a polycyclic aryl group optionally having a substituent(s), a heterocyclic group optionally having a substituent(s), an aryloxy group optionally having a substituent(s), a phenyl group having a substituent(s), an aralkyl group having a substituent(s), or a group represented by the following Formula (II):

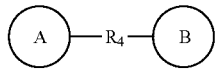
(II)

wherein Ring A and Ring B each represent a monocyclic or polycyclic aryl group or heterocyclic group optionally having a substituent(s); $R_4$ represents a single bond, a $C_{1-3}$ alkylene group optionally having a substituent(s), a $C_{2-3}$ alkenylene group optionally having a substituent(s), or a divalent oxy group; and the Ring A, Ring B, or $R_4$ moiety is linked to X;

$R_3$ represents 0 to 7 substituent(s) linked to the naphthyl group, each of which substituent(s) is the same or different and has 1 to 10 atoms; and X represents:
(i) a single bond;
(ii) a $C_{1-6}$ alkylene group optionally having a substituent(s);
(iii) a $C_{2-6}$ alkenylene group optionally having a substituent(s);
(iv) an —$R_5$—NH— group or an —NH—$R_5$— group, wherein $R_5$ represents a $C_{1-5}$ alkylene group optionally having a substituent(s), or a $C_{2-5}$ alkenylene group optionally having a substituent(s); or
(v) a secondary or tertiary amino group.

18. A method for preparing a pharmaceutical for the treatment of colon cancer, wherein said method comprises combining a pharmaceutically acceptable carrier and a therapeutic amount of a compound represented by Formula (I) or a pharmaceutically acceptable salt thereof:

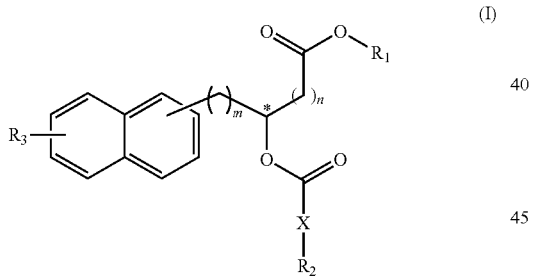
(I)

wherein m represents an integer of 0 to 3, and n represents an integer of 0 to 2, with the proviso that 1<m+n<3;

$R_1$ represents a hydrogen atom, a hydrocarbon group optionally having a substituent(s), a heterocyclic group optionally having a substituent(s), or an amino group optionally having a substituent(s);

$R_2$ represents a polycyclic aryl group optionally having a substituent(s), a heterocyclic group optionally having a substituent(s), an aryloxy group optionally having a substituent(s), a phenyl group having a substituent(s), an aralkyl group having a substituent(s), or a group represented by the following Formula (II):

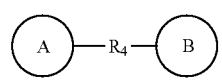
(II)

wherein Ring A and Ring B each represent a monocyclic or polycyclic aryl group or heterocyclic group optionally having a substituent(s); $R_4$ represents a single bond, a $C_{1-3}$ alkylene group optionally having a substituent(s), a $C_{2-3}$ alkenylene group optionally having a substituent(s), or a divalent oxy group; and the Ring A, Ring B, or $R_4$ moiety is linked to X;

$R_3$ represents 0 to 7 substituent(s) linked to the naphthyl group, each of which substituent(s) is the same or different and has 1 to 10 atoms; and X represents:
(i) a single bond;
(ii) a $C_{1-6}$ alkylene group optionally having a substituent(s);
(iii) a $C_{2-6}$ alkenylene group optionally having a substituent(s);
(iv) an —$R_5$—NH— group or an —NH—$R_5$— group, wherein $R_5$ represents a $C_{1-5}$ alkylene group optionally having a substituent(s), or a $C_{2-5}$ alkenylene group optionally having a substituent(s); or
(v) a secondary or tertiary amino group.

* * * * *